United States Patent
Pelrine et al.

(10) Patent No.: US 6,858,184 B2
(45) Date of Patent: Feb. 22, 2005

(54) MICROLABORATORY DEVICES AND METHODS

(75) Inventors: Ronald E. Pelrine, Boulder, CO (US); Subramanian Venkat Shastri, Palo Alto, CA (US); Jose P. Joseph, Palo Alto, CA (US)

(73) Assignee: SRI International, Menlo Park, CA (US)

(*) Notice: Subject to any disclaimer, the term of this patent is extended or adjusted under 35 U.S.C. 154(b) by 94 days.

(21) Appl. No.: 09/810,919

(22) Filed: Mar. 16, 2001

(65) Prior Publication Data

US 2002/0106314 A1 Aug. 8, 2002

(Under 37 CFR 1.47)

Related U.S. Application Data

(60) Provisional application No. 60/189,835, filed on Mar. 16, 2000.

(51) Int. Cl.[7] .................. G01N 33/48; B32B 27/04; B32B 27/12; B32B 5/02; B01L 3/02
(52) U.S. Cl. .................. 422/68.1; 422/63; 422/65; 422/99; 422/100; 422/101; 422/102; 422/103; 422/104; 436/518; 436/525; 436/526; 204/193; 204/194
(58) Field of Search .................. 422/99, 100, 63, 422/65, 68.1, 101, 102, 103, 104, 186; 436/518, 525, 526; 204/193, 194, 451, 643; 104/281

(56) References Cited

U.S. PATENT DOCUMENTS

| | | | |
|---|---|---|---|
| 3,597,022 A | | 8/1971 | Walron |
| 4,390,403 A | * | 6/1983 | Batchelder .................. 204/547 |
| 4,805,761 A | | 2/1989 | Totsch |
| 5,015,906 A | | 5/1991 | Cho et al. |
| 5,099,216 A | | 3/1992 | Pelrine |
| 5,187,399 A | | 2/1993 | Carr et al. |
| 5,298,875 A | | 3/1994 | Laibowitz et al. |
| 5,319,336 A | | 6/1994 | Alcon |
| 5,396,136 A | | 3/1995 | Pelrine |
| 5,454,472 A | * | 10/1995 | Benecke et al. .......... 209/127.1 |
| 5,645,702 A | * | 7/1997 | Witt et al. .................. 204/501 |
| 5,795,457 A | * | 8/1998 | Pethig et al. ................ 204/547 |
| 5,993,632 A | * | 11/1999 | Becker et al. ............... 204/547 |
| 6,075,924 A | | 6/2000 | Will |
| 6,296,752 B1 | * | 10/2001 | McBride et al. ............. 204/547 |
| 6,355,491 B1 | * | 3/2002 | Zhou et al. .................. 436/518 |

FOREIGN PATENT DOCUMENTS

| | | |
|---|---|---|
| JP | WO 98/14541 | 6/1999 |
| WO | WO 97/34689 | 9/1997 |
| WO | WO 14641 | 4/1998 |
| WO | WO 00/54882 | 9/2000 |
| WO | WO 0054882 | 9/2000 |

* cited by examiner

Primary Examiner—Jill Warden
Assistant Examiner—Brian Sines
(74) Attorney, Agent, or Firm—Perkins Coie LLP

(57) ABSTRACT

Disclosed herein are apparatuses and devices, and methods for using and making the same, for use in performing desired activities in an automated, microscale format. Microparticles are ushered about within a microscale apparatus, to selectively move between various stations in a selected order and manner. Some embodiments include reaction, micro-weighing, micro-analysis, reagent acquisition and deposition, and incubation stations. Microparticles can individually move, or move as trains. Samples, including particulate and solid tissue samples may be manipulated and analyzed within the device. Some embodiments may engage in micro-fabrication activities or micro-deconstruction activities. Systems for controlling such apparatuses are included as well as methods of operation.

12 Claims, 35 Drawing Sheets

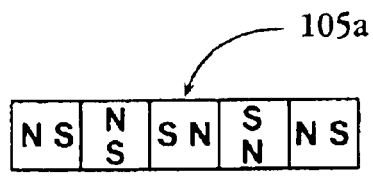
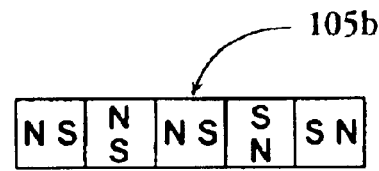
Fig. 2A  Fig. 2B
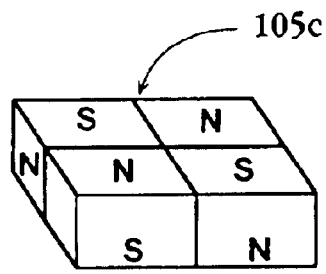
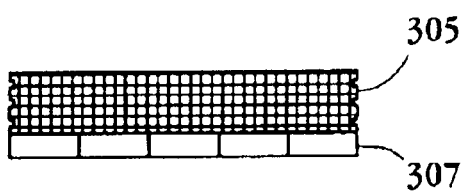
Fig. 3A  Fig. 3B
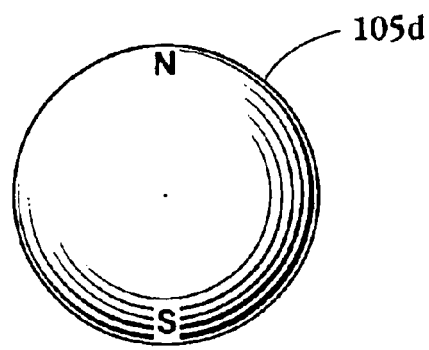
Fig. 4

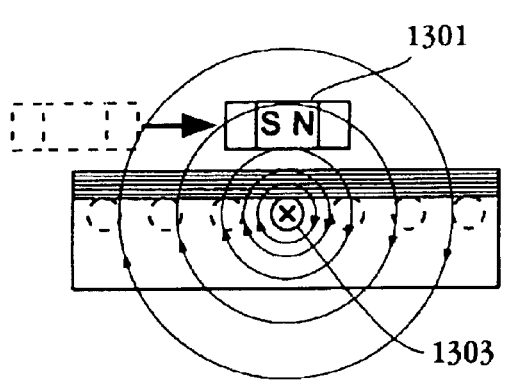
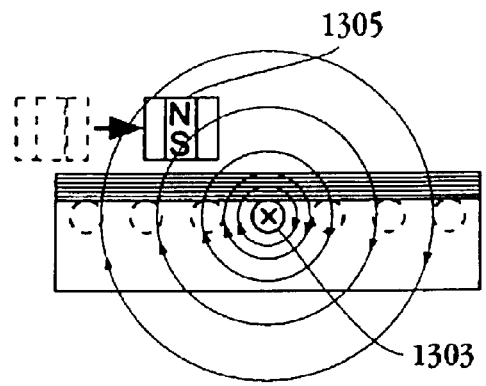
Fig. 13A            Fig. 13B
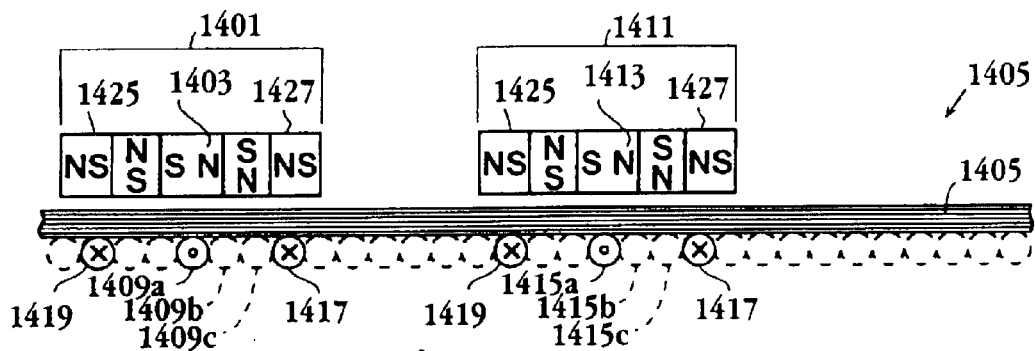
Fig. 14A
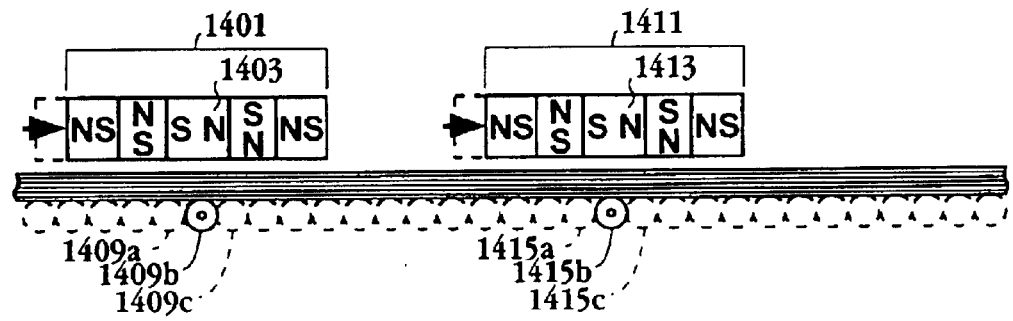
Fig. 14B
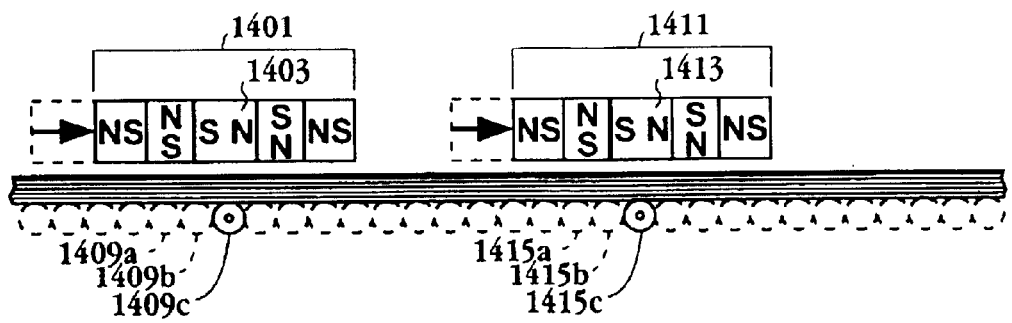
Fig. 14C

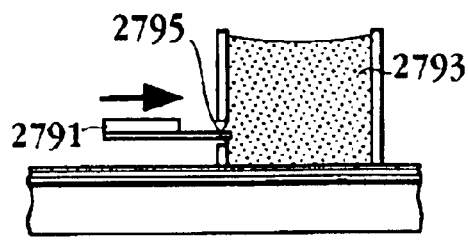
Fig. 27F(1)
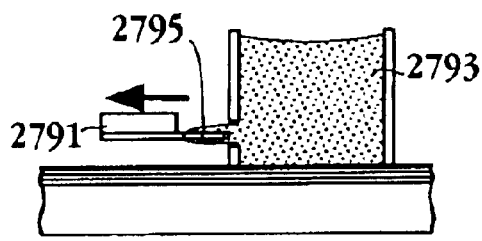
Fig. 27F(2)
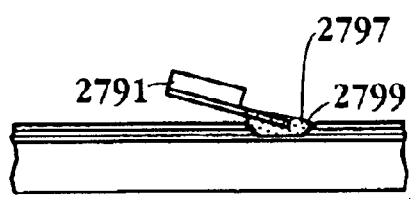
Fig. 27F(3)
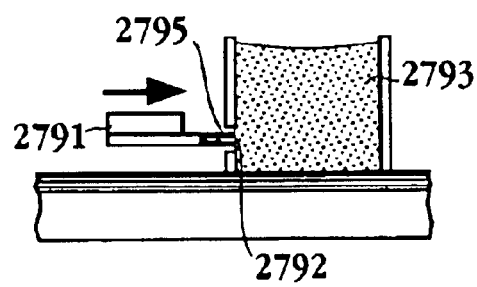
Fig. 27G(1)
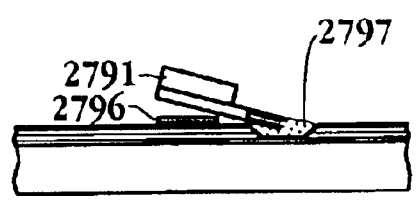
Fig. 27G(2)

MICROLABORATORY DEVICES AND METHODS

This application claims priority under 35 U.S.C. §119(e) to U.S. Provisional Patent Application No. 60/189,835, filed Mar. 16, 2000, which is herein incorporated by reference in its entirety for all purposes, including those described therein and herein.

FIELD OF THE INVENTION

This invention relates to the fields of micro-fluidics, micro-scale machinery, chemical synthesis and analysis devices, medical and diagnostic devices, micro-machines, and lab-on-a-chip technology.

BACKGROUND

Existing microfluidic systems typically rely on micro-scale pumps, channels, and/or electro-kinetic materials handling. These components have several potential drawbacks including clogging, inefficient pumping, viscous energy losses in the channels, inability to manipulate or tolerate particulates, and difficulty with high viscosity liquids. They also have system-level drawbacks. Each channel can generally carry only one high purity chemical without flushing. With only one chemical per channel, complex systems have routing and space difficulties. Further, at the reaction sites either valves or a constant positive outward flow are needed, to prevent back contamination.

The present invention radically departs from pump-channel systems and addresses the drawbacks noted above. Microparticles (beads and/or micromanipulators) carrying for example, chemicals, biological moieties or molecules, powders, samples, are moved about one or more micro-scale lab workplace through interactions between microparticles and drive or biasing elements. A motivating force is generated and controlled by conventional microcircuits, for example, printed circuit boards, silicon circuits, and flex circuits, above and/or below the workplace.

SUMMARY OF THE INVENTION

The invention includes, in one aspect, a levitating-particle device in which magnetic microparticles and/or effectors are levitated adjacent a diamagnetic surface, with controlled movement laterally to different stations on a planar substrate, through activation of circuit traces formed on the substrate, or moved through gas by electrostatics.

In various embodiments the device includes (i) a first substrate with first driving circuitry, and a second substrate with biasing circuitry, to stabilize and control the movement of microparticles in a vertical direction; (ii) controlling circuitry such that a plurality of microparticles/effectors are moved simultaneously to different reaction zones on the substrate; (iii) structure allowing microparticle and/or effector movement in both lateral and vertical directions; and (iv) levitation storage shelves in which microparticles and/or effectors can be out of plane on the shelves.

In another aspect, the levitating-particle device provides reaction or storage chambers in the above device, and the microparticles and/or effectors are moved through a gas/liquid interfaces at the openings of the chambers.

In various embodiments, (i) the chambers are vertically offset from the plane of lateral microparticle travel, and microparticles are popped into and out of chambers across a gas/liquid interface; (ii) the substrate includes a first substrate with driving circuitry, and a second substrate with biasing circuitry, to stabilize and control the movement of microparticles in a vertical direction, and (iii) the chambers are in the plane of lateral microparticle travel, and microparticles are moved laterally into and out of chambers across a gas/liquid interface.

In particularly preferred embodiments, a plurality of chambers are consecutively situated such that the outlet port of a first chamber is adjacent or abutting an inlet port of a second chamber so that a microparticle moving between each chamber travels through little to no air gap between such ports.

In other embodiments, once a microparticle enters a chamber containing a liquid and a gas, entering the liquid portion first, the microparticle nears a surface created by the interface between a liquid and gas and travels along such surface, selectively either on the gas or the liquid side, or alternatively remaining in the liquid away from such interfacial surface.

In another aspect, the levitating-particle device is designed to allow groups of microparticles to be moved together in train or platoon fashion, either by coordinately controlling the positions of all microparticles in the train, through parallel traces, or by only controlling the movement of a single "locomotive" or active microparticle, where the such locomotive microparticles move other "rolling stock" or passive microparticles in the train through magnetic, electrical, repulsion or attraction or other frictional, or adhesive relations among and/or between the train microparticles. In other embodiments, two or more active microparticles are selectively motivated to control one or more passive microparticles.

In various embodiments, (i) the microparticles are moved on and out of the train, to alter the composition of the trains; and (ii) the microparticles of the train are moved as a unit in and out of chambers, for example, wash, reaction, chemical deposition, incubation, or weighing chambers.

In another aspect, the levitating-particle device has a substrate and a plurality of reaction stations formed thereon, and microparticles and/or effectors are moved from station to station to effect sequential exposure of microparticles to two or more chemicals.

In various embodiments, (i) the device can be programmed to carry out a plurality of different reactions in different order, with different chemicals, reagents, or exposure conditions; (ii) the microparticles are moved laterally to stations, and vertically into and out of vertically offset chambers; (iii) the stations have two or more connected reaction chambers, where microparticles can be moved into one chamber of the station, and between and among chambers of the station, e.g., in and out of a central wash chamber; (iv) the effectors act to carry reagents to or from the reaction chambers on the substrate; (v) the effectors carry reagents from the reaction chambers to the microparticles; (vi) for use in constructing a chemical library, the library microparticles are either labeled for identification, or their history is monitored so that each microparticle can be identified with a selected library compound; (vii) for carrying out multi-analyte diagnostics, each microparticle becomes associated with an analyte, and is carried from station to station as necessary for developing analyte-specific chemistry; and (viii) for carrying out high-throughput screening, by moving chemicals into contact with screening entities, for example, cells, and/or moving cells on effectors to different screening areas.

In another embodiment, microparticles may contain reagents for conducting polymerase chain reaction or PCR experiments, for example, a porous or gel-like material attached to or integral to a microparticle, where such a microparticle is selectively moved among different regions of the device, each region having a different thermal property, so that the microparticle's temperature raises and lowers according to a selected PCR temperature profile, for a selected number of cycles, to carry out PCR on a microparticle. In preferred embodiments, a plurality of microparticles are circulated among different temperature regions within the device to carry out PCR on different microparticles simultaneously. In yet other embodiments, different microparticles are exposed to different conditions or profiles to carry out PCR optimization protocols on a plurality of microparticles.

In another embodiment, the device has a reaction station with two or more chambers separated laterally or vertically from one another and a fluid-interface, and microparticles are moved between and among the chambers.

In various embodiments, (i) the microparticles are moved through gas space separating two liquid containing chambers; (ii) the microparticles are moved directly from chamber to chamber across a liquid—liquid interface; and (iii) the station has a central wash chamber surrounded by a plurality of reagent chambers.

In another embodiment, two or more devices are placed together, as interchangeable modules, to expand the capacity and operations of each module.

In another aspect, the device is designed for use in synthesizing polymers, for example, polynucleotide molecules with selected sequences, on microparticles, for use in, for example, assaying DNA analytes that may bind to such microparticles.

In still another embodiment, the levitating-particle device is designed for carrying out nanofabrication methods, for example, where the microparticles, or optionally, just their effectors if present, are selectively moved in and out of contact with one of more workpieces, to selectively add or remove molecules or layers to the workpiece in a selected manner.

In another aspect, the invention provides for an apparatus for use in performing a desired laboratory or manufacturing activities with microparticles, in an automated, microscale format, preferably while the microparticles are levitated. Here, the apparatus includes a first substrate having a workplace defining x-y coordinates; one or more microparticles adapted for controlled movement adjacent the workplace, the microparticles each adapted for having one or more magnetic or electrostatic dipoles and one or more effectors for use in the laboratory or manufacturing activities; a plurality of laboratory and/or manufacturing stations located at different known workplace x-y coordinates, each laboratory station being adapted to carry out or participate in one or more selected laboratory operations with the microparticle effectors; a driving structure positioned adjacent the workplace, the driving structure having a plurality of drive elements selectively energizable to move one or more of the microparticles between selected workplace x-y coordinates, through interactions of the drive elements with the microparticles' dipoles; and, a controller operatively linked to the drive elements for energizing the drive elements to move the one or more selected microparticles between or among selected laboratory or manufacturing stations to accomplish the desired laboratory or manufacturing activity or activities.

In certain embodiments, a second substrate is adapted to be placed adjacent the first-mentioned substrate to form a continuous workplace with expanded x-y coordinates with additional laboratory stations carried on the second substrate. A second driving structure may be positioned adjacent the second workplace which has a plurality of drive elements selectively energizable to move one or more of the microparticles between selected second-substrate workplace x-y coordinates, through interaction of the drive elements with the microparticles' dipoles. The controller may be operatively linked to the drive elements of the second driving structure for energizing the second-structure drive elements to move one or more selected microparticles between or among selected laboratory stations on the second substrate, and the drive elements of the two drive structures are energizable to move microparticles from one substrate to another.

In still other embodiments, the controller is operatively linked to the second structure drive elements for energizing the second-structure drive elements to move one or more selected microparticles between or among selected laboratory stations, and the second structure drive elements of the second drive structure are energizable to move microparticles between the first substrate and the second substrate. In yet other embodiments, different controllers may be used to control, for example, different substrates of the apparatus, or different sections within a substrate. In yet other embodiments, a second controller could be designed for a single function, for example, to carry out wash or other chemical operations with a microparticle, and may optionally have an optical sensor to detect when the first substrate sends a microparticle into the second substrate's workspace, where then the second substrate may optionally perform another operation after which, the microparticle may be sent to an output path such as back to the first substrate, or to a third substrate, where the apparatus optionally may have modular building blocks of substrates, each independently operating, so that the whole apparatus employs a decentralized approach for design and operational simplicity and versatility.

In other embodiments, the driving structures may farther include one or more biasing elements effective to impart vertical, z-dimension forces to microparticles positioned or moving on the substrate, to move one or more selected microparticles to different selected z-axis positions, or to control movement of the microparticles in a z direction.

In certain embodiments, at least some of the laboratory stations include a chamber for holding a selected liquid, and a chamber opening which defines a gas/liquid interface, when the chamber contains such liquid, the driving structure includes work-station drive elements which are effective, when energized, to move microparticles across the interface into and out of the chamber, and the controller is effective to activate such work-station drive elements to accelerate microparticles crossing the interface in a gas-to-liquid direction, and to accelerate, then brake microparticles crossing the interface in a liquid-togas direction.

Other embodiments may be used for synthesizing one or more chemical compounds on one or more of the microparticles, wherein the microparticles having surface-attached chemical groups on which the compounds can be synthesized, and the laboratory stations are adapted to hold chemical-synthesis and wash reagents for accomplishing chemical reactions on the microparticles. Other embodiments may be used for a method that relies on a binding reaction between first and second compounds or a first compound and a biological cell, wherein at least one of the microparticles has surface attached first compound, and at least one of the laboratory stations contains the second compound or biological cells, or for transferring material from one laboratory station to another, wherein at least one of the microparticles includes an effector for picking up and carrying such material from one station and for depositing the material at a second station.

Another aspect of the invention provides for an apparatus for use in performing one or more desired laboratory activities in an automated, microscale format, comprising a substrate forming a workplace expanse having an upper surface, one or more laboratory stations formed within the substrate, one or more trenches formed within the substrate, the trenches interconnecting the laboratory stations in a selected format, the trenches being capable of holding one or more liquids, one or more microparticles adapted to movably fit within the trenches, the microparticles each having one or more magnetic or electrostatic dipoles and one or more laboratory effectors, a driving structure positioned adjacent the workplace, the driving structure having a plurality of drive elements selectively energizable to move one or more of the microparticles through the trenches, through interactions of the drive elements with the microparticles' dipoles, and a controller operatively linked to the drive elements for energizing the drive elements to move the one or more selected microparticles between or among selected laboratory stations interconnected by the trenches to accomplish the desired laboratory-activity.

Various embodiments may include, one or more cover structures adapted to fit against the substrate's upper surface to form therein one or more channels from the trenches, two or more electrodes for selectively passing one or more electrical currents through the trenches when such are filled with one or more conductive media, wherein the electrical currents are capable of electrokinetically causing or controlling movement of one or more reagents or analytes within the trenches and between the laboratory stations so that one or more selected reagents or analytes can selectively contact selected microparticles, a wash reservoir connected by a first trench to a first drain reservoir, a reagent reservoir connected by a second trench to a second drain reservoir, wherein the first and second trenches intersect to form an intersection for transiently exposing a microparticle to a reagent, the reservoirs each having disposed therein an electrode adapted to electrically communicate with a liquid contained within the reservoirs so that when a first electrical current is passed between the reagent reservoir electrode and the second drain reservoir electrode, reagent is electrokinetically introduced into the intersection for contacting with a selected microparticle passing along the first trench through the intersection. The intersection may form an offset double-tee intersection. Other embodiments may include one or more biasing elements positioned adjacent the intersection(s) for selectively holding the selected microparticles within the intersections. The microparticle may be adapted for moving within the device in a levitated state. Other embodiments may include one or more diamagnetic layers defining a levitation surface wherein the microparticles are adapted to stably levitate by diamagnetic levitation. In other embodiments, the levitated state results wholly or in-part from electrostatic levitation, and/or the levitated state results wholly or in-part from buoyant levitation, and or, the levitated state results wholly or in-part from surface tension levitation, and./or the levitated state occurs transiently.

The devices of the invention may include one or more biasing elements for causing the microparticles to move toward or away from the biasing elements.

Another aspect of the invention provides for a method for carrying out desired laboratory activities in an automated, microscale format comprising the steps of providing a microfluidic device having formed therein one or more trenches or channels containing one or more microparticles, the microparticles having one or more magnetic or electrostatic dipoles, the device having a driving substrate with one or more drive elements disposed therein, the drive elements being capable of acting upon the microparticles' dipoles to cause the microparticles to selectively move about the trenches or channels, controlling the position of the microparticles within the microfluidic device by activating selected drive elements to cause the microparticles to move between selected laboratory stations so that each of the selected microparticles is acted upon by each selected laboratory station in a desired sequence and manner.

In another aspect, the invention provides for an apparatus for use in performing a desired laboratory activity in an automated, microscale format. The apparatus may include a first substrate having a workplace defining x-y coordinates; one or more microparticles adapted to levitate adjacent the workplace, wherein the microparticles each having a magnetic or electrostatic dipole and one or more laboratory effectors; a plurality of laboratory stations located at different known workplace x-y coordinates, each laboratory station being adapted to carry out or participate in one or more selected laboratory operations with the microparticle effectors; a driving structure positioned adjacent the workplace, the driving structure having a plurality of drive elements selectively energizable to move one or more of the microparticles between selected workplace x-y coordinates, with the microparticles in a levitated state, through interactions of the drive elements with the microparticles' dipoles, and a controller operatively linked to the drive elements for energizing the drive elements to move the one or more selected microparticles between or among selected laboratory stations to accomplish the desired laboratory-activity.

Various embodiments may include; the first substrate having a diamagnetic layer, the one or more microparticles being magnetic microparticles where the microparticles levitate adjacent the workplace by diamagnetic levitation, the substrate being adapted to support a layer of fluid in which the microparticles are buoyant, and the microparticles levitate adjacent the workplace by buoyancy, the substrate being adapted to support a layer of fluid having a surface displaying surface tension upon which the microparticles are supported against, the microparticles having a density greater than that of the fluid, and the surface tension being sufficient to support the microparticle above the surface, the microparticles having a density greater than that of the fluid, and the surface tension being sufficient to retain the microparticles below the surface when upwardly biased.

In other embodiments, the apparatus may further include a second substrate adapted to be placed adjacent the first-mentioned substrate to form a continuous workplace with expanded x-y coordinates, additional laboratory stations carried on the second substrate, a second driving structure positioned adjacent the second workplace, and having a plurality of drive elements selectively energizable to move one or more of the microparticles between selected second-substrate workplace x-y coordinates, with the microparticles in a levitated state, through interaction of the drive elements with the microparticles' dipoles, and the controller being operatively linked to the drive elements of the second driving structure for energizing the second-structure drive elements to move one or more selected microparticles between or among selected laboratory stations on the second substrate, and the drive elements of the two drive structures are energizable to move microparticles from one substrate to another.

Other embodiments may include a second substrate adapted to be placed adjacent the first substrate to augment microparticle levitation within the workplace having x-y coordinates, a second driving structure positioned adjacent the second substrate, and having a plurality of second structure drive elements selectively energizable to move one or more of the microparticles between selected workplace x-y coordinates, with the microparticles in a levitated state, through interaction of the second structure drive elements with the microparticles' dipoles, and the controller being operatively linked to the second structure drive elements for energizing the second-structure drive elements to move one or more selected microparticles between or among selected laboratory stations, and the second structure drive elements of the second drive structure are energizable to move microparticles between the first substrate and the second substrate.

Yet other embodiments may include having the driving structure further include one or more biasing elements effective to impart vertical, z-dimension forces to microparticles levitating on the substrate, to move one or more selected microparticles to different selected z-axis positions, or to control movement of the microparticles in a z direction.

In still other embodiments, at least some of the laboratory stations include a chamber for holding a selected liquid, and an chamber opening which defines a gas/liquid interface, when the chamber contains such liquid, the driving structure includes workstation drive elements which are effective, when energized, to move microparticles across the interface into and out of the chamber, and the controller is effective to activate such work-station drive elements to accelerate microparticles crossing the interface in a gas-to-liquid direction, and to accelerate, then brake microparticles crossing the interface in a liquid-to-gas direction.

In other embodiments, the apparatus may be used for synthesizing one or more chemical compounds on one or more of the microparticles, wherein the microparticles having surface-attached chemical groups on which the compounds can be synthesized, and the laboratory stations are adapted to hold chemical-synthesis and wash reagents for accomplishing chemical reactions on the microparticles. In yet other embodiments, the chemical synthesis is combinatorial in nature wherein the encoded microparticles are directed from one reaction chamber to another, while tracking the particular history of each microparticle, such movement optionally being split and pool in nature where the microparticles are collected in a central chamber to create a microparticle pool from which the microparticles are redistributed to each reaction vessel while their codes are tracked and histories recorded.

Still other embodiments may be suitable for use in a method that relies on a binding reaction between first and second compounds or a first compound and a biological cell, wherein at least one of the microparticles has surface attached first compound, and at least one of the laboratory stations contains the second compound or biological cells. And other embodiments may be suitable for transferring material from one laboratory station to another, wherein at least one of the microparticles includes an effector for picking up and carrying such material from one station and for depositing the material at a second station.

In one aspect, the invention provides for an apparatus for use in performing a desired laboratory activity in an automated, microscale format. In a preferred embodiment, the apparatus includes a first substrate having a workplace defining x-y coordinates where one or more microparticles having a magnetic or electrostatic dipole and one or more laboratory effectors levitates adjacent the workplace. Within the workplace, a plurality of laboratory stations adapted to carry out or participate in one or more selected laboratory operations with the microparticle effectors are located at different known workplace x-y coordinates. Adjacent the workplace is a driving structure having a plurality of drive elements selectively energizable to move one or more of the microparticles between selected workplace x-y coordinates is positioned adjacent the workplace, while the microparticles are in a levitated state, through interactions of the drive elements with the microparticles' dipoles. The apparatus may be controlled by a controller operatively linked to the drive elements, for energizing the drive elements to move one or more selected microparticles between or among selected laboratory stations to accomplish one or more desired laboratory-activities.

In other embodiments, the apparatus further includes the substrate having a diamagnetic layer where one or more magnetic microparticles levitate adjacent the workplace by diamagnetic levitation, and/or, where the substrate is adapted to support a layer of fluid in such that the microparticles are buoyant and levitate adjacent the workplace by virtue of their buoyancy, and/or, where the substrate is adapted to support a layer of fluid having a surface displaying surface tension upon which the microparticles are supported or retained underneath by biasing, and/or, where the microparticles have a density greater than that of the liquid, and the surface tension is sufficient to support the microparticles above the surface, or when the microparticles have a density less than the liquid, the surface tension is sufficient to retain the microparticles beneath the surface liquid-gas interface.

In yet other embodiments, the apparatus further includes a second substrate adapted to be placed adjacent the first-mentioned substrate to form a continuous workplace with expanded x-y coordinates, where additional laboratory stations are carried on the second substrate, and positioned adjacent the second workplace is a second driving structure having a plurality of drive elements selectively energizable to move one or more of said microparticles between selected second-substrate workplace x-y coordinates, with said microparticles in a levitated state, through interaction of said drive elements with said microparticles' dipoles, where the controller is operatively linked to the drive elements of the second driving structure for energizing the second-structure drive elements to move one or more selected microparticles between or among selected laboratory stations on the second substrate, and the drive elements of the two drive structures are energizable to move microparticles from one substrate to another.

In still other embodiments, the apparatus includes a second substrate adapted to for placement adjacent the first substrate to augment microparticle levitation within the workplace having x-y coordinates. Positioned adjacent the second substrate is a second driving structure having a plurality of second structure drive elements selectively energizable to move one or more of said microparticles between selected workplace x-y coordinates, with said microparticles in a levitated state, through interaction of said second structure drive elements with said microparticles' dipoles. The controller is further operatively linked to the second structure drive elements for energizing said second-structure drive elements to move one or more selected microparticles between or among selected laboratory stations, and the second structure drive elements of the second drive structure are further energizable to move microparticles between said first substrate and said second substrate.

In other embodiments, the driving structure further includes one or more biasing elements which are effective to impart vertical, z-dimension forces to microparticles levitating on the substrate, to move one or more selected microparticles to different selected z-axis positions, or to control movement of the microparticles in a z direction.

In yet other embodiments, at least some of the laboratory stations include a chamber for holding a selected liquid, and an chamber opening which defines a gas/liquid interface, when the chamber contains such liquid, said driving structure includes workstation drive elements which are effective, when energized, to move microparticles across the interface into and out of the chamber, and said controller is effective to activate such work-station drive elements to accelerate microparticles crossing said interface in a gas-to-liquid direction, and to accelerate microparticles crossing said interface in a liquid-to-gas direction. The drive elements may further decelerate or brake movement of the moving microparticle.

Other embodiments include the microparticles having surface-attached chemical groups on which compounds can be synthesized, and the laboratory stations being adapted to hold chemical-synthesis and wash reagents for accomplishing chemical reactions on the microparticles. Furthermore, the apparatus may be for use in a method that relies on a binding reaction between first and second compounds or a first compound and a biological cell, where at least one of the microparticles has surface attached first compound, and at least one of the laboratory stations contains the second compound or biological cells. The apparatus may also be used for transferring material from one laboratory station to another, where at least one of the microparticles includes an effector for picking up and carrying such material from one station and for depositing said material at a second station.

In another aspect, the invention provides for a magnetic microparticle for use in carrying out micro-scale chemical operations. Such microparticles preferably are formed from a magnetic substrate characterized by (i) a surface, optionally substantially flat, having a maximum dimension in the range 50–500, (ii) a magnetic dipole whose magnetic field lines are substantially normal to the surface, and (iii) an energy density of at least 10 megagauss-oersted, such that the microparticle, when placed surface down on a diamagnetic surface, is able to levitate on the diamagnetic surface, and, (iii) a region on the microparticle having an effector for carrying out or participating in a selected chemical, laboratory, analytical, or manufacturing operation. Preferably, the magnetic substrate may be formed of rare earth metals, may be substantially disc shaped, may have the flat surface have a maximum dimension of between 50–100 microns, may include indicia readable by a code reader, for purposes of identifying the microparticle, may have its effector include surface-attached biopolymer molecules, may have the effector include surface-attached chemical groups which can support bipolymer synthesis, may have its effector be a manipulator effective to interact with other microparticles to transfer chemical material to or from such other microparticle, may have its effector be a sensor adapted to sense a target material or event, may have the microparticle formed of two or more regions with oppositely directed magnetic poles, where such regions may be oppositely directed magnetic poles are interspersed with regions whose magnetic poles are oriented normal to said direction of said first-mentioned poles, and/or may have the microparticle have side walls adjacent the flat surface, and a coating of diamagnetic material covering at least a portion of the side walls.

In another aspect, the invention provides for an apparatus for exposing a magnetic microparticle to a plurality of liquid reagents. In preferred embodiments, the apparatus includes a diamagnetic substrate having a workplace defining x-y coordinates, and on which a microparticle can levitate. Located at different known workplace x-y coordinates are a plurality of laboratory and/or manufacturing stations, where each station has a chamber for holding a selected liquid, and a chamber opening forming a gas/liquid interface when the chamber contains such liquid. Each station is adapted to carry out or participate in one or more selected laboratory operations with effectors carried on the microparticles. Positioned adjacent the workplace, is a driving structure having (i) a plurality of first drive elements selectively energizable to cause an interaction between selected energized drive elements and one or more selected microparticles, to move the microparticles between selected workplace x-y coordinates, with the microparticles in a levitated state, through interaction of said drive element with the microparticles' dipoles, and (ii) second drive elements associated with each station, selectively energizable to cause an interaction between selected energized drive elements and (iii) one or more selected microparticles, to move said microparticles across said gas/liquid interfaces at said stations. A controller is operatively linked to the drive elements for energizing the drive elements to move one or more selected microparticles between or among selected laboratory stations, and in and out of laboratory stations, to accomplish desired laboratory-activities.

In some embodiments, one or more stations are substantially in-plane with the x-y movement of the microparticles on the substrate, and the opening includes a capillary port communicating between the interior of the chamber and the workplace, and, second drive elements may be associated with an in-plane station include an exterior drive element on the external side of the station's port, and an internal drive element on the internal side of the station's port, where the interior and exterior drive elements may each include first and second electromagnetic coils disposed on opposite lateral sides of the port.

In other embodiments, the interior drive element associated with each station is energizable to accelerate microparticles external to said gas/liquid interface through the interface into the station's chamber, and the exterior drive element associated with the station is energizable to initially accelerate microparticles within the station's chamber, as the microparticle passes through the liquid/gas interface, then may brake the movement of the microparticle after it has passed such interface, where such braking may further include de-energizing the drive element, and using the viscosity of the liquid to brake the microparticle. The apparatus may have the braking further include a combination of reverse energizing the drive element to brake the microparticle along with using said fluid to further brake said microparticle, or the braking may be entirely achieved by reverse energizing the drive element, or the braking may be assisted by a nearby conductive surface using eddy current damping.

In still other embodiments, a station has one or more chambers, each separated from the other by a capillary port intended to contain a gas and define a gas/liquid interface between each chamber and the port, when the chambers are filled with a liquid, or may have a central station surrounded by a plurality of peripheral stations, each communicating with the central station through a capillary port intended to contain a gas and define a gas/liquid interface between each chamber and said port, when the stations are filled with a liquid. A station may be defined by a cavity formed in said substrate where an opening is formed by the upper surface of liquid contained in a cavity, and second drive elements are energizable to move the microparticles in a substantially z direction across the gas/liquid interface into and out of the station, and where the second drive elements associated with such cavity-defined laboratory station may include exterior and interior drive elements disposed on exterior and interior sides of the station opening, respectively. The interior drive elements associated with a station may be energizable to accelerate a microparticles external to the gas/liquid interface, downwardly across the gas/liquid interface into the station's chamber, and the exterior drive element associated with the station is energizable to initially accelerate a microparticle within the station's chamber upwardly, as the microparticle passes through the liquid/gas interface, and may then brake the movement of the microparticle after it has passed such interface.

In another aspect, the invention provides for an apparatus for use in performing multi-particle operations.

In preferred embodiments, the apparatus includes a substrate having a workplace defining x-y coordinates, a plurality of microparticles adapted to levitate adjacent the workplace, the microparticles each having a magnetic dipole. Positioned adjacent the workplace is a driving structure having a plurality of drive elements selectively energizable to move a linear train of selected microparticles coordinately between selected workplace x-y coordinates, with said microparticles in a levitated state, through interactions of the drive elements with the microparticles' dipoles. A controller is operatively linked to the drive elements for energizing the drive elements to move the microparticles coordinately between or among selected laboratory stations to accomplish the desired laboratory-activity. In some embodiments, the microparticles in the train are magnetically coupled in said direction of train movement, whereas in others, the microparticles in the train are magnetically uncoupled in said direction of train movement, and/or the controller operatives to add or remove selected microparticles to the train, as the train is moved from one region on the workplace to another.

In another aspect, the invention provides for a controller for controlling the movement of one or more microparticles. In preferred embodiments, the controller includes a controller circuit that is adapted to send signals that energize one or more drive elements adjacent a workplace surface defined by a substrate. The one or more drive elements are in communication with the controller such that signals which are selectively communicated to one or more selected drive elements, energize those selected drive elements to selectively produce an attracting force or a repelling force which acts upon the dipole(s) of one or more adjacent levitating microparticles. The attracting force or the repelling for then causes the microparticle(s) adjacent the selected drive element to move towards the drive element, and the repelling force causes at least one of said one or more microparticles to move away from the energized drive element.

In another aspect, the invention provides for an apparatus and methods for directing movement of microparticles within a micro-laboratory device having therein one or more locations. The apparatus includes a substrate having an upper surface, one or more drive element track loops for moving the microparticles about the substrate surface, the loops each defining a loop path and each loop comprising a plurality of drive elements adapted to cause selective movement of the microparticles along the loop path by electrostatic or magnetic interactions between the microparticles and the drive elements so that a selected microparticle will move along a selected loop path when the drive elements of the loop are selectively activated, one or more biasing elements adjacent one or more of the loop paths for attracting, holding, and/or repelling the microparticles traveling along the loop paths and by the biasing elements, the biasing elements being adapted to attract, hold, and/or repel the microparticles traveling by the biasing elements when activated, a controller device for selectively activating the drive elements of the loops and selectively activating the biasing elements to transiently form one or more routes between two or more desired locations within the device for causing directed movement selected microparticles to the desired locations within the micro-laboratory device.

Some embodiments include a route formed by transiently creating an apparatus state of a first loop having a first biasing element being adapted to hold and release a selected microparticle when activated and deactivated, one or more second biasing elements being adapted to direct movement of the released microparticle from the first loop's path to one or more intermediate loops' paths subsequently adjacent the first loop's path when activated and deactivated, and a third biasing element being adapted to attract and hold the released microparticle traveling along the intermediate loops' paths so that when the microparticle passes the third biasing element, the microparticle is captured and selectively held by the third biasing element.

Some embodiments may include one or more loop detectors adapted for detecting the microparticles when passing by the loop detector, the loop detectors being in communication with the controller for providing feedback information on the movement of microparticles throughout the apparatus.

In still other embodiments, at least one loop detector is adapted to detect an identification code uniquely associated with each microparticle.

These and other objects and features of the present invention will become more fully apparent when the following detailed description of the invention is read in conjunction with the accompanying drawings.

BRIEF DESCRIPTION OF THE FIGURES

FIG. 2A depicts a cross-sectional view of a rectangular sandwich type diamagnetic levitation microparticle.

FIG. 2B depicts a microparticle with its opposite ends having the same outward polarity.

FIG. 3A depicts a top-down view of a magnetic matrix microparticle.

FIG. 3B depicts a top-down view of a concentric co-axial magnetic matrix microparticle.

FIG. 4 depicts a bipolar magnetic sphere microparticle.

FIGS. 13A and 13B depict a simple dipole magnet moving toward a preferred position while levitating above a diamagnetic substrate adjacent a driving substrate having energized drive elements disposed therein.

FIGS. 14A–14C depict the directed movement of two different microparticles across a workplace above a diamagnetic surface.

FIGS. 25A–D depict a different laboratory station used for reacting and incubating microparticles with a reagent which has side port access for which a microparticle may pass through.

FIGS. 27A–27J depict the use of a chemical pick-up effector attached to a microparticle.

DETAILED DESCRIPTION OF THE PREFERRED EMBODIMENTS

The problems discussed above, and other problems, are addressed by the present invention by providing apparatuses, methods, and devices for use in performing a desired laboratory and/or manufacturing activities in an automated, micro-scale format. Unlike the prior art, the invention utilizes, in preferred embodiments of one aspect, methods and devices using a substrate having a workplace defining x-y coordinates; one or more microparticles adapted for controlled movement adjacent the workplace where the microparticles are each adapted for having or inducible to have one or more magnetic or electrostatic dipoles. The dipoles may be physical dipoles such as a magnetic dipole made of permanent magnet material, or they may be apparent dipoles relative the background medium. For example, a non-magnetic sphere in a ferrofluid (a liquid with suspended colloidal magnetic particles) upon which a uniform magnetic field is imposed has an apparent dipole because the ferrofluid medium is magnetized and the non-magnetic sphere is not. The microparticles further include one or more laboratory effectors for performing a function. The microparticles navigate to and between one or more laboratory or manufacturing stations located at different known workplace x-y coordinates where each laboratory station is adapted to carry out or participate in one or more selected laboratory operations with the microparticle effectors. A driving structure, in some embodiments, is positioned adjacent the workplace where the driving structure has a plurality of drive elements selectively energizable to move one or more of the microparticles between selected workplace x-y coordinates, through interactions of the drive elements with the microparticles' dipoles; and, a controller operatively linked to the drive elements for energizing the drive elements to move the one or more selected microparticles between or among selected laboratory stations to accomplish the desired laboratory-activity.

Figure 1A:
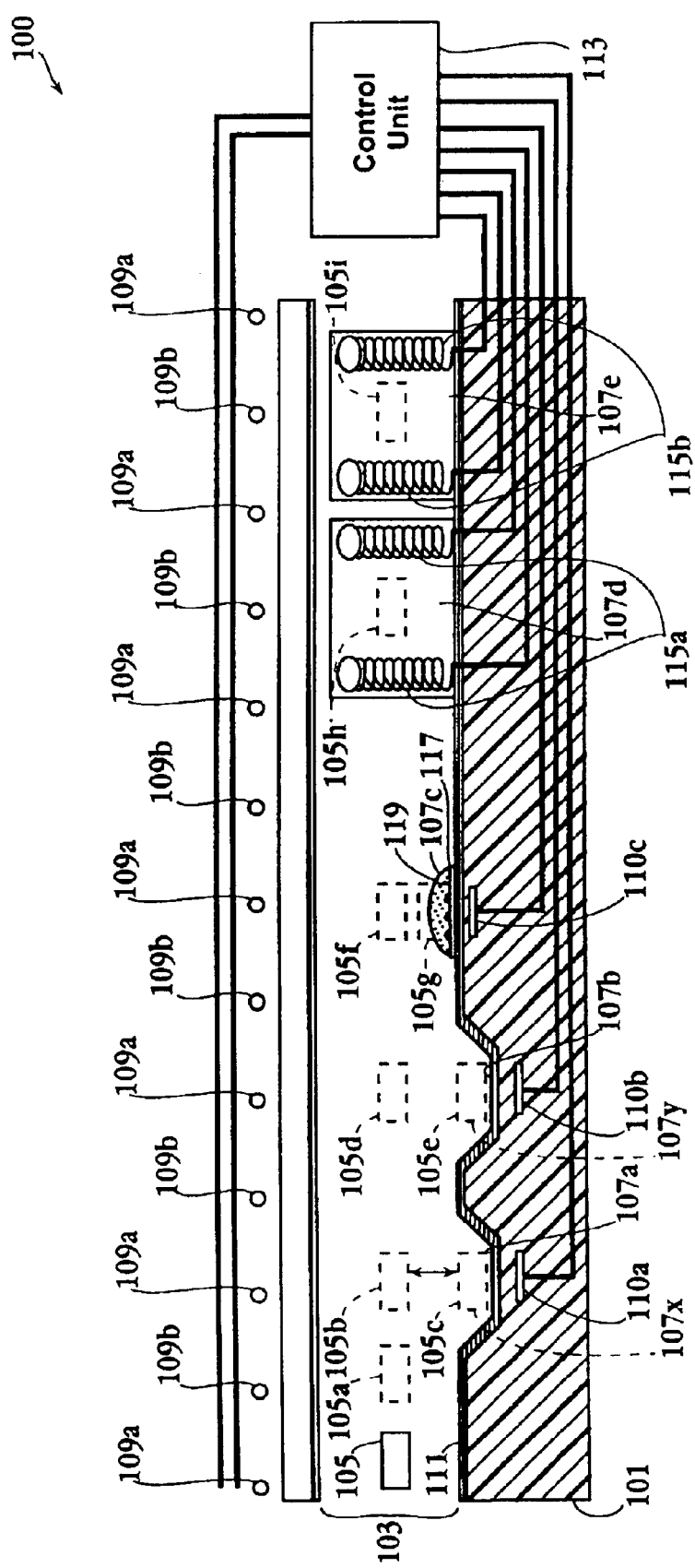
FIG. 1A depicts a cross-sectional view of a diamagnetic levitation micro-laboratory system.

In one aspect of the invention, microparticle movement between laboratory stations is shown in FIG. 1A that depicts a cross-sectional view of a diamagnetic levitation microlaboratory system 100. Substrate 101 defines workplace 103 where microparticle 105 stably levitates while moving between laboratory stations 107*a–e*, as indicated by positions 105*a–i*. Laboratory stations 107*a–e* are adapted to carry out or participate in one or more selected laboratory operations with microparticle 105.

In a preferred embodiment microparticle 105, is formed from a plurality of magnets, where the magnetic dipole between layers of the sandwich alternates in different directions, as shown at 105*a*–105*c* in FIGS. 2A–3B. For example, the present invention adapts the levitating magnet array of Pelrine, U.S. Pat. No. 5,396,136, which is entirely incorporated herein by reference for all purposes, to be used in the micro-laboratory environment of the present invention. FIG. 3B further depicts optional porous material effector 305 attached to microparticle 307, in this case a multi-dipole microparticle, where the porous material is used for adsorbing or attaching compounds and biological moieties to said microparticle. The microparticle depicted in 3B is useful, for example, in microfluidic devices with intersecting channels where the microparticle may be transiently situated within the intersection, and an electrical current is passed through the intersecting channel, passing through the porous material to contact a reagent contained within a liquid within the intersecting channel to cause such reagent to contact the porous material.

In other, particularly preferred embodiments, microparticle 105 is a magnetic or electrostatic ball, sphere, spheroid shape, or other ball-like shape. Microparticle 105 may be rolled along without being levitated if its cross-sectional shape is round or otherwise adapted for rolling or flopping end over end, for example, spheres and cylinders for rolling, rectangular and square bodies. (See dipole 105d in FIG. 4 for example.) The dipole may be a permanent dipole fixed in the ball or other rolling or flopping shape, or it may be an induced dipole whose direction relative to the ball changes. Other embodiments include a layered structure with one or more non-flat surfaces. In still other embodiments, the microparticles may have field lines non-normal to a surface, or a combination of normal and non-normal field lines with respect to the surface.

In some embodiments, the microparticles are made from rare earth magnetic materials, for example, alloys containing one or more of the following elements in selected ratios; neodymium, samarium, iron, cobalt, and boron. In preferred embodiments, the microparticles are made from two or more of the elements selected from the group consisting of neodymium, samarium, iron, cobalt, and boron. In particularly preferred embodiments, the microparticles are made from three or more of the elements selected from the group consisting of neodymium, samarium, iron, cobalt, and boron. Other preferred embodiments use microparticles made from neodymium-iron-boron and/or samarium-cobalt. In still other embodiments, the dipoles or polar regions of the microparticles are induced by an external source. For example, microparticles made from para-magnetic materials may transiently develop one or more magnetic dipoles in response to an external magnetic field. The hysteresis of the magnetic dipole established in the microparticle may further be exploited by rapidly depolarizing the external inducing force to cause either a repulsion or attraction of temporarily polarized microparticle. Other materials having longer, even fixed dipole formation (magnetizable) abilities may be used to form and un-form dipoles at-will. Materials such as dielectrics or dielectric polymers may be used to create microparticles for which electrostatic dipoles may be formed and unformed. Such microparticles are particularly useful when used in conjunction with dielectrophoretic lab on a chip technologies such as described in Batchelder, U.S. Pat. No. 4,390,403, herein incorporated by reference in its entirety for all purposes including methods and devices for conducting dielectrophoresis in microcapillary lab-on-a-chip devices. The present invention contemplates an improvement to Batchelder by placing microparticles in the micron or nanometer scale into the device of Batcheleder, and moving such through such capillary channels by dielectrophoresis, or in combination with drive structures as described herein.

Microparticle 105 differs, however, from Pelrine, above, in that it further comprises one or more laboratory effectors for carrying out laboratory activities with laboratory stations. For example, an effector may be a chemical synthesis bead that acts as a chemical support for conducting chemical synthesis, or the effector may be a region of the microparticle adapted for carrying fluids or other materials between stations. In other embodiments, the effector is a region or appendage of the microparticle for carrying solids, for example, powders or body tissue samples. Other examples of preferred effectors are provided below. In certain embodiments, various components of the apparatus are adapted to hold, carry, sample, react, measure, mix, apportion, cut, hydrate, dehydrate, desiccate, cool, heat, centrifuge, weigh, and/or aspirate biological moieties including cell(s), virus(es), molecules, compounds, tissue (s), solutions, samples, proteins, polynucleotides, including DNA, RNA, cDNA, aptomers, enzymes, receptors, antibodies, body fluids, and analytes.

Diamagnetic surface 111 is formed from a diamagnetic material such as pyrolytic graphite, isotropic graphite, or bismuth. Diamagnetic surface 111 works with microparticle 105's magnetic fields to cause microparticle 105 to levitate above diamagnetic surface 111, as described in Pelrine, above. Diamagnetic surface 111 may be coated, if needed, with a very thin passive material such as a polymer or metal to prevent direct contact between the diamagnetic material and specific reagents.

In preferred embodiments, microparticle movement between laboratory stations may result from the sequential energizing of drive elements 109a and 109b. For example, while microparticle 105 levitates at position 105a in workplace 103 above diamagnetic surface 111 by diamagnetic levitation, drive elements 109a and 109b operate in concert to usher microparticle 105 along surface 111 towards laboratory station 107a which contains a fluid reagent, not shown.

In preferred embodiments, the movement of microparticle 105 caused by the sequential energizing of drive elements 109a and 109b is continuous, although the microparticle may be pulled or pushed away from the effects of such alternating drive elements by an adjacent biasing element. By way of metaphor, this is analogous to the microparticle being moved along on a "conveyor belt" that results from alternating the drive elements acting on the one or more dipoles within microparticle 105. Occasionally, microparticle 105 is plucked from, and replaced onto the "conveyor belt" by an energized or de-energized biasing element, to capture microparticle 105 for conducting laboratory activities with selected laboratory stations, or to replace microparticle 105 back onto the "conveyor belt", respectively. For example, with the "conveyor belt" being in continuous operation, a biasing element used for pulling a microparticle into a well, may be activated prior to the arrival of a microparticle moving on the "conveyor belt". As the microparticle nears the activated biasing element, the microparticle is acted upon by the drive element causing the microparticle to move away from the "conveyor belt", towards the drive element, and into the well. The microparticle reacts for a period of time in the well until it is released or ejected from the well to resume movement on the "conveyor belt" or conveyance system which conveys microparticles from one selected location to another.

Biasing elements may have, preferably, multiple operational states. For example, a biasing element may be activated to capture a passing by microparticle by developing an attractive force effective to capture a passing by microparticle from the conveyance system control. Once captured, the biasing element may then be switched to a hold-state that applies enough attracting force to maintain the once passing by, but now captured microparticle in a captured position adjacent the biasing element. The hold-state of a biasing element does not cause additional passing by microparticles to be captured or held by the biasing element. Thus, the hold-state permits holding of a microparticle without attracting additional microparticles that may pass near the hold-state biasing element. A third state of biasing element operation includes an repelling-state where a once captured and held microparticle is repelled or ejected away from the biasing element and is urged toward the conveyance system. A fourth state of biasing element operation includes an off state where the element is deactivated such that it does not hold, attract, or repel microparticles.

Movement of a single microparticle around a circuit of stations may be conducted by using biasing elements in off, attracting, or repelling states but without the intermediate holding-state. In this example, biasing elements in their capture-state will capture any microparticles passing by. Such activated biasing elements may indeed capture several, if not all of the circulating microparticles that pass by.

Biasing elements may also be used to assist in levitating a microparticle that would otherwise not levitate by alone. This is a particularly useful technique when the microparticle consists of a single, rather than multiple, dipoles.

A particularly preferred embodiment include all four states; attracting, holding, repelling, and off. Here, a biasing element that is in the hold-state, holding a microparticle, would not capture additional passing by microparticles from the conveyance system. In preferred embodiments, all but one of the microparticles are captured by some of the biasing elements, each of such biasing elements retaining their respective microparticles by a holding-state activation of the biasing element. The remaining microparticle continues to circulate and re-circulate about the conveyance system until such microparticle meets a biasing element in a capture-state, thereby capturing the passing microparticle. Such capture may be followed by the selective release of another microparticle held at another biasing element in a holding-state. Release may occur as the result of depolarization, reverse polarization, or polarization of the biasing element such that the once captured microparticle is released, or in some instances, ejected away from the biasing element, and in all cases, no longer held by the biasing element. The released microparticle then is engaged within the conveyance system to be circulated or re-circulated to another selected location or laboratory station within the apparatus. The apparatus may then carry out multiple, simultaneous laboratory activities with microparticles by using the conveyance system to move about or shuffle microparticles between different laboratory stations or locations, as other microparticles remain captured in their selected positions.

In some embodiments, the same component may serve both as a biasing element and as a drive element, depending on how the component is configured and operated.

Biasing elements and drive elements may be positioned within or outside of the substrate. For example, a biasing element may be located outside of a substrate made from a diamagnetic material where such biasing element's effect effectively penetrates the substrate to act upon an adjacent microparticle. Drive elements may be similarly situated and used.

Simplified control of the system, therefore, may be realized, in preferred embodiments, by selectively activating drive elements, in a defined sequence, with the "conveyor belt" moving the microparticles between stations. The sequence of lab stations adjacent the "conveyor belt" may determine the sequence of laboratory events that will occur, as could the sequence for which the biasing elements associated with a laboratory station are activated determine the sequence of steps performed on a microparticle. The amount of time a microparticle may remain in a well, if at all, is determined by the time that a drive element is energized while it acts upon microparticle that has traveled by on the conveyor belt. The above system represents an open system, where the position of a microparticle need not be tracked to operate the system. Each subsequent energized drive element acts to capture and retain a passing microparticle, for a set period of time.

As microparticle 105 moves over laboratory station 107a to achieve position 105b, biasing element 110a is energized to pull microparticle 105 down into laboratory station 107a to achieve position 105c within well 107x which contains a liquid, not shown, which interacts with microparticle 105, or a component of microparticle 105 such as an effector, to change at least one characteristic of microparticle 105 or microparticle 105 changes at least one characteristic of the liquid in well 107x. After microparticle 105 has remained in laboratory station 107a to carry out a selected laboratory activity, microparticle 105 is then urged out of the fluid within laboratory station 107a by removing or reversing the magnetic polarity of biasing element 110a which then causes microparticle 105 to "pop" out of well 107x altogether and resume a levitated state above the well. Popping refers to microparticle 105's emergence from the fluid contained in well 107x, as it breaks free from the surface of such fluid to enter a gas phase away from the fluid.

In some embodiments, biasing elements are positioned within the workplace above the substrate surface. In other embodiments, biasing elements are positioned on the side of the substrate opposite the workplace. In still other embodiments, biasing elements may be positioned or integrated within the substrate. In other embodiments, different biasing elements may be located at different positions with respect to the substrate cross-section. In still other embodiments, the substrate(s) and driving structure(s) are integrated, whereas in other embodiments, the substrate(s) and driving structure(s) are separate.

Upon emergence from laboratory station 107a, microparticle 105 is further ushered along by drive elements 109a and 109b toward laboratory station 107b as it assumes position 105d. Microparticle 105 is then pulled into laboratory station 107b, shown as well 107y, which contains a second reagent, not shown, by energized biasing element 110b, to further react in accordance with a selected laboratory activity such as washing. Microparticle 105 is then popped out of the second reagent contained in well 107y of laboratory station 107b by removing or reversing the polarity of drive element 110b. Upon emergence from the second reagent in well 115, microparticle 105 resumes its levitated state and is ushered to laboratory station 107c to react with a third reagent.

Laboratory station 107c is a "surface well" or region on substrate surface 111 where liquid, in the form of droplet 119, is maintained by hydrophobic ring 117 which forms a circle on the substrate surface for retaining the droplet in proximity with biasing element 110c. Alternatively, in the situation where the liquid contained is hydrophobic, a hydrophilic containment ring may be made upon surface 111. Examples of such "well-less" configurations are described by Kumar, et al., U.S. Pat. No. 5,512,131, herein incorporated by reference in its entirety for all purposes including the purpose of teaching differential surface treatments and micro-stamping techniques. As microparticle 105 moves near laboratory station 107c, biasing element 110c energizes to pull microparticle 105 from its travel path to achieve position 105g within liquid droplet 119 located within ring 117.

In some embodiments, the wells of the device are usually arranged so that they are similar to commercially available plates such as microtiter plates (96 well, 3456 well, etc.). In other embodiments, the device is configured to communicate with the spatial arrangement of a commercially available microtiterplate or similar well plate, so that materials may be either deposited to or acquired from such plates by the device.

In preferred embodiments, laboratory stations may be within the workplace such as with laboratory station 107d which is placed on surface 111 and has a side access port, not shown, for passing microparticle 105 through as microparticle 105 enters laboratory station 107d. Port drive element 115a is also elevated above surface 111 to assist the pulling in of microparticle 105 inside laboratory station 107d. Port drive element 115a is oriented normal to surface 111, although it may be oriented in plane to surface 111, or some other selected angle. Port drive element 115a comprises two or more opposing coils or electromagnets which are energized to attract, hold, or repel microparticle 105, depending on the spatial relation between port drive element 115a and microparticle 105. Port drive element 115a may also be formed from a single, doughnut shaped coil having a central hole for microparticle 105 to pass through as it enters laboratory station 107d.

The ushering of microparticle 105 through workplace 103 results from energizing drive elements controlled by control unit 113 which supplies electrical impulses to each of the drive elements and biasing elements in accordance with a programmed set of instructions. As described above, drive elements 109a and 109b worked in concert to usher microparticle 105a through workplace 103. FIG. 1A shows two drive elements 109a and 109b, but more than two may be used for specific embodiments. Such drive elements work in concert by switching on and off, or by reversing the electrical current polarities in the drive elements, in a manner which hand-off microparticle 105 from a previously energized drive element 109a to a now energized drive element 109b. Such movement is perpetuated by the ongoing switching of consecutive drive elements in conjunction with microparticle 105's inertia. In preferred embodiments, described in detail below, tracks consisting of two or more sets of serpentine traces can be used to motivate or usher a microparticle in a forward or reverse direction, depending on how each trace is energized. With two drive element circuits, a microparticle can be controllably moved through a workplace with minimal control or feedback required. By simply oscillating the energizing of each track element, a microparticle levitating above or resting on such track is motivated to move in a selected direction. A system that does not require or has minimal feedback requirements is called an open loop system, whereas a system requiring a higher degree or complete feedback is a closed loop system or feedback system.

Figure 1B:
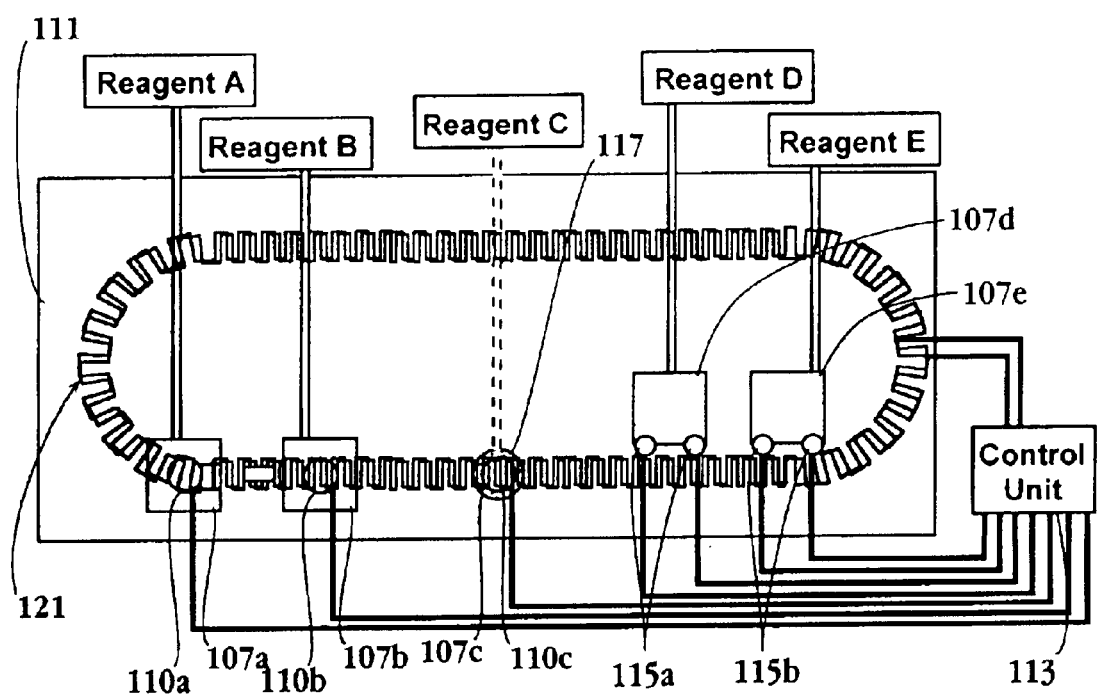
FIG. 1B depicts a top-down view of the diamagnetic levitation micro-laboratory system of FIG. 1A.

FIG. 1B depicts a top-down view of the diamagnetic levitation micro-laboratory system of FIG. 1A, described above. Not shown in FIG. 1A is the circular nature of the layout of drive elements 109a and 109b, which are serpentine tracks offset from one another by about 90 degrees, together forming x, y-movement circuit 121 about surface 111.

Circuit 121, when operated by the alternating energizing of drive elements 109a and 109b, causes microparticle 105 to "orbit" about surface 111, periodically passing laboratory stations 107a–e, under the control of control unit 113, which is in communication with each drive element, biasing element, and port drive element in the system. As microparticle 105 orbits, it may be pulled into a selected one of the plurality of laboratory stations along the orbital path of microparticle 105. For example, if microparticle 105 is to visit laboratory station 107d, then, port drive element 115a is energized to cause microparticle 105 to enter. Upon completion of the laboratory function, port drive element 115a may then "reverse" or depolarize to release or push out microparticle 105 thereby causing microparticle 105 to resume the orbit of circuit 121.

Microparticles suitable for use with the invention include millimeter-scale (milli) in about the 10–1 millimeter range, and the micrometer-scale (micro) in about the 1000–1 micrometer range. Other microparticles are larger than 10 millimeters or smaller than 100 nanometers. The requisite features for a suitable microparticle are that the microparticle must have, or be inducible to have, one or more one dipoles or be able to hold a charge, and must have at least one effector for use in carrying out a selected laboratory function. For example, a polystyrene microparticle capable of maintaining a charge may be used in a system where the drive elements produce electrostatic fields which either attract or repel such a microparticle, and that the microparticle has at least one effector such as a surface coating displaying an antigen, or region for carrying a reagent or compound in bulk form.

In preferred embodiments, a microparticle is a magnetic microparticle which has a magnetic-substrate characterized by (i) a surface having a maximum dimension ranging from about 1 $\mu$m to about 2 mm, more preferably between about 50 $\mu$m to about 500 $\mu$m, still more preferably from about 25 $\mu$lm to about 500 $\mu$m, still more preferably from about 25 $\mu$m to about 250 $\mu$m, (ii) at least one magnetic dipole whose magnetic field lines are normal to the surface, and (iii) an energy density of at least 10 megagauss-oersted and more preferably at least 30 megagauss-oersted, such that the microparticle, when placed flat-surface down on a diamagnetic-surface, is able to levitate on the diamagnetic-surface, and a region on the magnetic-substrate having an effector for carrying out or participating in a selected laboratory operation. In some cases a bias magnetic field from a bias electromagnet or bias permanent magnet element is needed to assist the levitation, especially for lower energy density magnetic materials, larger microparticle sizes, and weaker diamagnetic materials. In preferred embodiments, the surface is a substantially flat surface.

In other embodiments, the system is reversed, where the microparticle is wholly or partly made from diamagnetic material, and the substrate (that portion which in other embodiments was the diamagnetic surface) is now a magnetic or magnetizable surface.

FIGS. 2A and 2B depict microparticles similar to the levitating microparticle of Pelrine, above, in that such microparticles comprise a first member that is defined by an array of magnets or magnetic dipoles which are arranged to provide a high strength, high gradient magnetic field adjacent one surface of the array. More specifically, the magnets are arranged in a side-by-side sequence with each consecutive magnet having opposite magnetic polarity. This arrangement provides closed loop magnetic flux paths for each two consecutive magnets that intercept both magnetic poles of the two magnets. A second member that is formed from a diamagnetic or other material having a relative magnetic permeability that is less than one interacts with the magnetic field to levitate the magnetic first member. This second member defines a base or area over which the levitated magnetic array may be moved by external forces.

The microparticle of FIG. 2A differs from that of FIG. 2B in that 2A has opposing ends having different magnetic poles, and 2B has the same poles (both "N" poles). By having different opposing end magnetic poles, two or more microparticles may be selectively coupled like train cars for moving a train of multiple microparticles in unison or as platoon, and later de-coupling such cars as needed. Assembling microparticles in trains for unified movement provides the advantage of simplifying control for group activities, such as washing, but later breaking up such trains for individual, separate reactions, such as in combinatorial chemical synthesis where splitting and pooling are desired at different stages of combinatorial chemical compound library synthesis.

FIG. 3A depicts a top-down view of a magnetic matrix microparticle, and FIG. 3B depicts a top-down view of a concentric co-axial magnetic matrix microparticle. Both of these types of microparticles are useful in devices where independent x, y movement is desired. Independent x, y movement differs from the track-based movement described above in that each or groups of drive elements operates independently from one another in different x, y directions. For example, an array of point drive elements may be used, where each point drive element is independently energizable, to move about a microparticle in two or more degrees of freedom. Wire like drive elements adjacent and parallel to the workplace may be arranged in a grid or multiple, off-angle grid like fashion, to create intersecting active regions of drive elements to increase the degrees of freedom of movement between x, y coordinates. For example, printed circuit board technology may be used to create multiple layers of electrical traces in a grid-like pattern, with several layers being off-angle to the others to cross such traces at less than or greater than normal angles.

FIG. 4 depicts a bipolar magnetic sphere microparticle 105d that is a simple, and easily produced microparticle. In some microparticle embodiments, the effector may be a coating surrounding the magnetic material, where the coating is suitable for attaching moieties such as a compound, molecule, peptide, protein, polynucleotide, oligonucleotide, DNA, cDNA, mRNA, RNA, or other natural or synthetic polymer to the magnetic microparticle in a way that does not deactivate the attached moiety. When the microparticle is a sphere or is spheroidal in shape, the surface measurement of the microparticle is determined from a cross-sectional diameter.

Figure 5A:
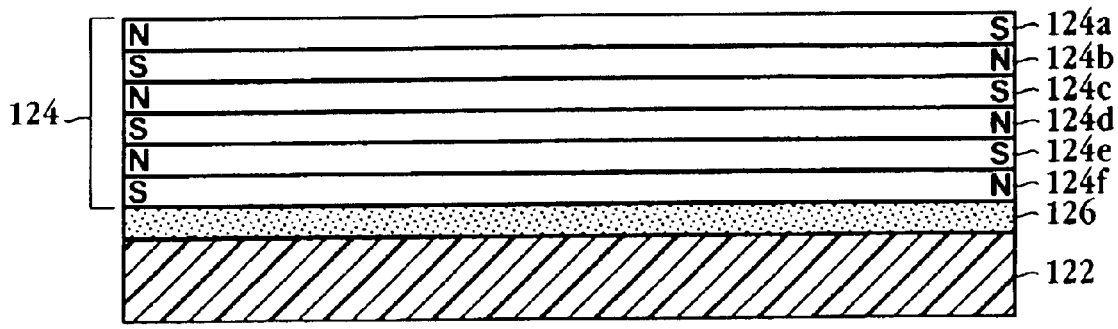
FIGS. 5A–C depict a preferred method of making microparticles.
Figure 5B:
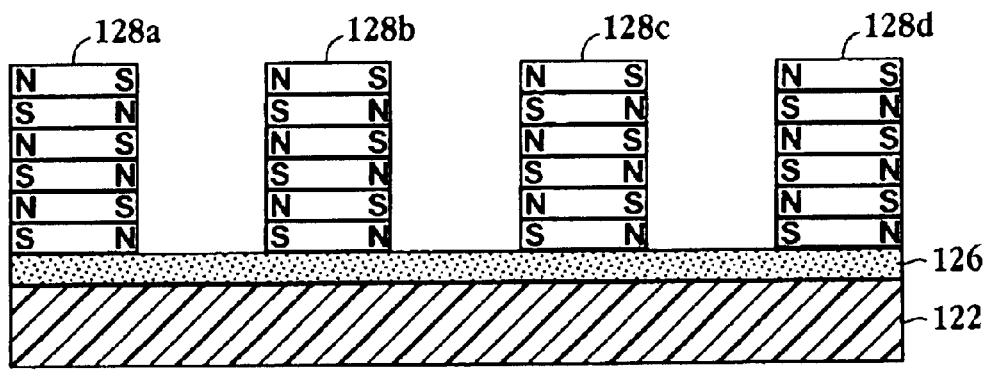
Figure 5C:
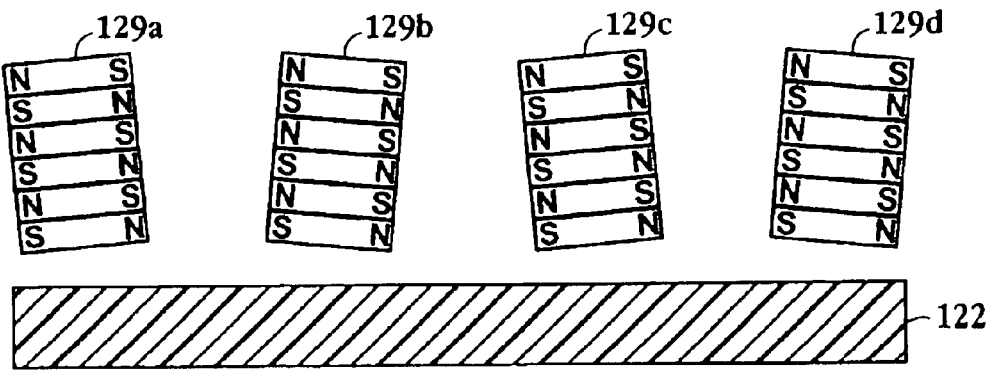

Manufacturing, storage, and placement of magnetic microparticles used in a micro-laboratory may be achieved, for example, in the following ways. FIGS. 5A–5C depict a process where a substrate 124 formed from multiple layers, such as layers 124a, 124b, of different materials, including at least one magnetic or magnetizable material, is selectively etched to produce stacked cylinders of such different materials, as seen in FIG. 5B. The process includes bonding a support layer 122 to the multi-layer substrate 124 with a sacrificial layer 126 interposed there between. To release the stacked cylinders, the sacrificial layer is removed by etching, as shown in FIG. 5C, producing desired particles 129a–d. Other methods include electrochemical build-up in defined compartments of a porous substrate to form stacked-encoded cylinders which may be made by adapting the cylinders or nanorods, for example, of B. R. Martin, et al., Advanced Materials, 1999, 11: 1021–1025 to form stacked cylinders made from different materials. To make microparticle sandwiches having layers with different dipole orientations, the method of Martin, above, may be adapted by layering magnetic materials while exposing such cylinders to a magnetic field sufficient to cause polar orientation of the magnetic material at each layer as it is formed.

Figure 6A:
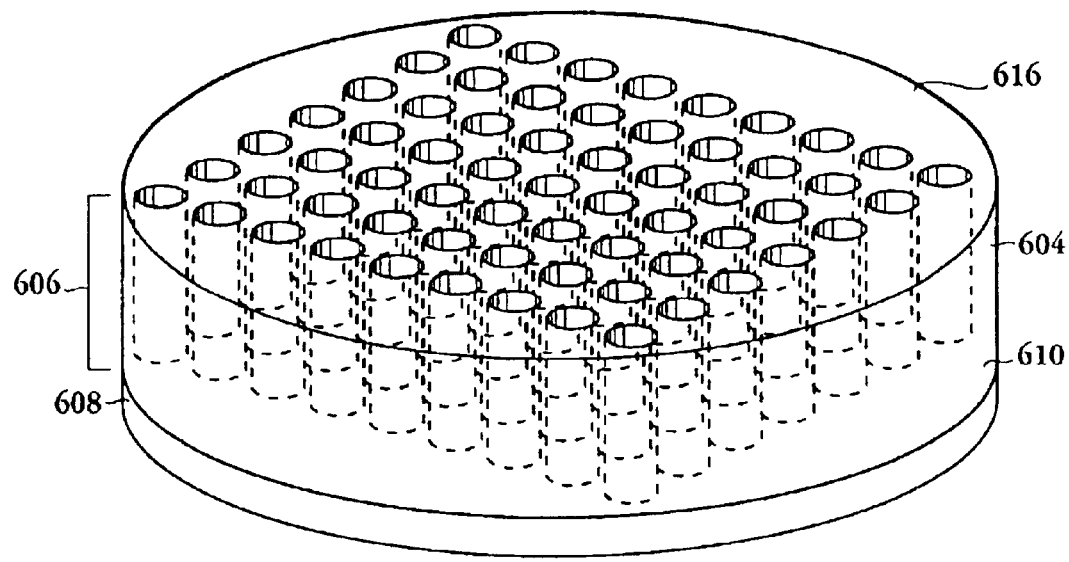
FIGS. 6A–C depict a preferred method of making microparticles.
Figure 6B:
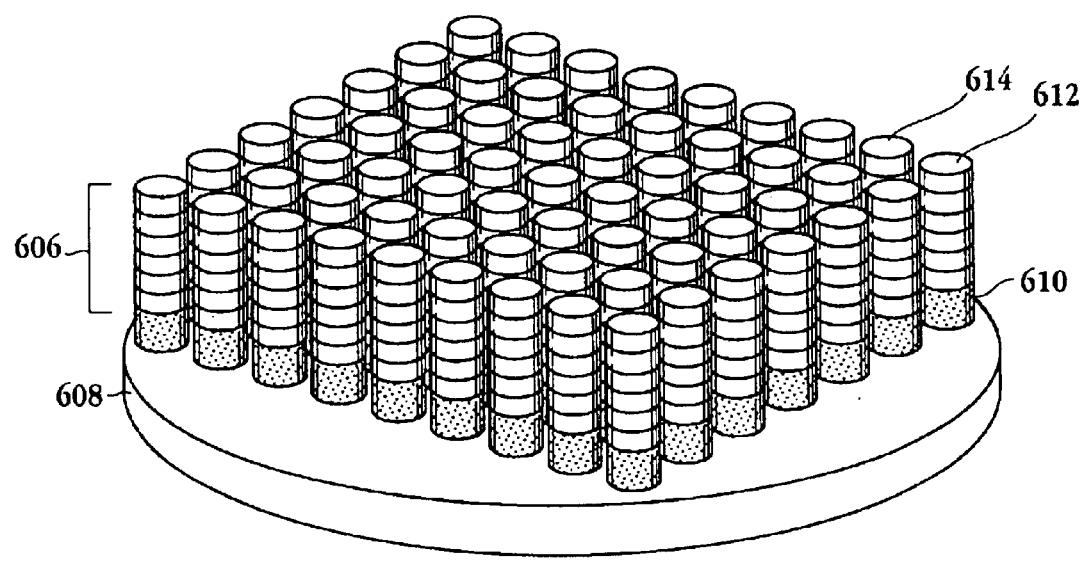
Figure 6C:
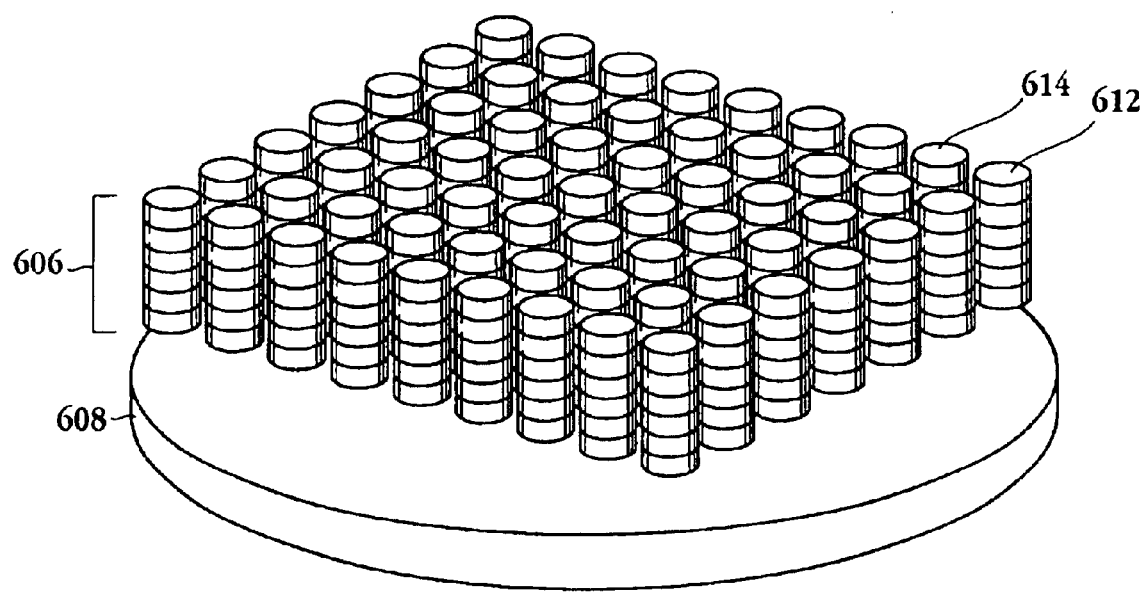

Another method for manufacture of magnetic particles is illustrated in FIGS. 6A–6C. Here, the microparticles may be formed by sandwiching together sheets of magnetic material, such as sheets 602, 604, having different dipole orientations to form a sandwich 606. Sandwich 606 is bonded to a support via a sacrificial layer 610. Microparticles of a desired shape and size are then cut from the sandwich, as depicted in 6B, by means of photolithography or plasma etching type procedures. As seen in FIG. 6B, microparticles 612, 614, which are exemplary, are formed upon removal of material 616. The sacrificial layer 610 is them removed, such as by dissolving the layer is a suitable solvent, to release the microparticles from support 608, as see in FIG. 6C.

Microparticles, upon manufacturing, may be bulk stored, or stored in a spaced-apart manner. For example, microparticles that have been formed in a spaced apart manner may be retained in a spaced apart manner by transferring such microparticles to another substrate that has biasing elements in a spaced apart array or other formation adapted to transfer such microparticles directly into a micro-laboratory device. Once placed in the micro-laboratory device, the transfer substrate may be separated from the microparticles by either removing the biasing elements, or de-energizing such. Alternatively, the micro-laboratory device may be energized to grab the microparticles from the transfer substrate, as the transfer substrate is removed. The micro-laboratory device may further be kept energized or otherwise active with respect to holding each microparticle in its newly deposited position. In other embodiments, a transfer template is used which the microparticles transiently attach to, preferably by biasing elements, which selectively hold each microparticle at a known position until transferred to a micro-lab device or apparatus.

Figure 7:
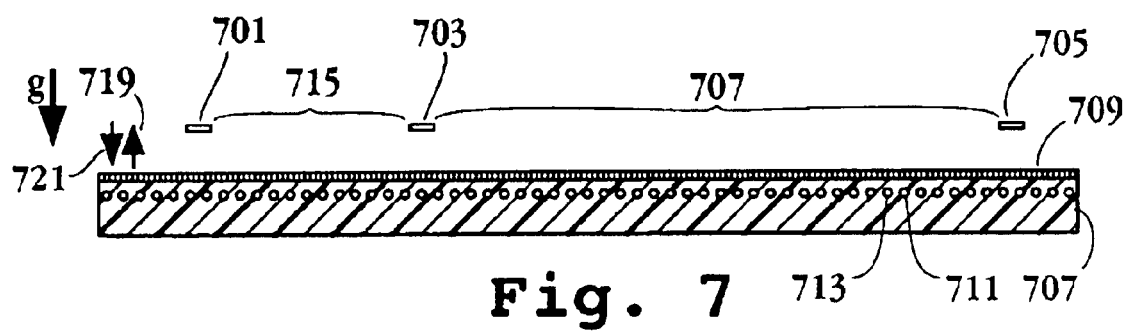
FIG. 7 depicts a cross-sectional view of several magnetic microparticles levitating above a diamagnetic substrate adjacent to a driving structure.

In some preferred embodiments, the nature of the relationship between stably levitating magnetic microparticles and the levitation substrate is similar to that described by Pelrine, above. FIG. 7 depicts a cross-sectional view of several magnetic microparticles (701, 703, 705) levitating above a diamagnetic substrate 709 that is adjacent to a driving structure 707. The microparticles in FIG. 7 are spaced-apart a distance (715, 717) sufficient to prevent each microparticle from affecting the stability of the next adjacent microparticle. Assuming the drive elements shown are not activated, the microparticles will remain in place. By selectively activating drive elements, or biasing elements, such microparticles may be moved in x, y, or z directions with respect to the levitation substrate. Microparticle levitation in FIG. 7 relies, in-part, on the collective forces of gravity acting on the microparticle to pull it toward the levitation substrate, and the repulsive or magnetic reflection of the magnetic field of the microparticle reflecting back upon the microparticle by the diamagnetic surface, thereby causing the microparticle to levitate.

FIG. 7 depicts three microparticles, from left to right as 701, 703, and 705, levitating adjacent levitation substrate 707 defining surface 709. Drive elements 711 and 713 are, in this embodiment, embedded within the substrate. Microparticles 701 and 703 are maintained at a spaced apart distance 715 by activating drive elements adjacent such microparticles. If the drive elements were deactivated, microparticles 701 and 703 would either move towards one another, or repel away from one another depending upon the dipole arrangement of each microparticle. In contrast, microparticles 703 and 705 are maintained passively away from each other because neither can attract or repel the other at distance 717 regardless of each microparticles dipole configuration.

Figure 8:
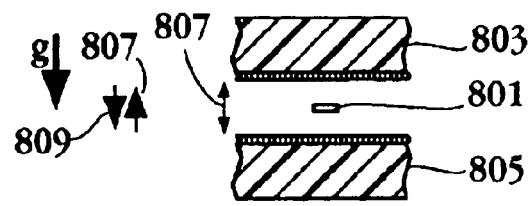
FIG. 8 depicts a cross-sectional view of a magnetic microparticle levitating between two opposing diamagnetic substrates adjacent to a driving structure.

FIG. 8 depicts a particularly preferred embodiment where levitating microparticle 801 levitating between levitation substrates 803 and 805, while being maintained at distance 807 from each substrate. Microparticle 801's position is maintained by a combination of forces including gravity, g, and the diamagnetic repulsions 807 and 809 caused by the relation between the microparticle and each diamagnetic surface. In certain embodiments, the effect of gravity reduced to negligible levels by employing the sandwich configuration of FIG. 8 in conjunction with biasing/drive elements, not shown, that can positionally maintain a microparticle If microparticle 801 is a single magnetic dipole, for example, a bias electromagnetic element located above the levitation substrate 803 can lift most or all of the weight of microparticle 801 using magnetic attraction between the bias element and the microparticle's magnetic dipole. The amount of lift can be adjusted as needed by varying the electrical current in bias electromagnet.

In some embodiments, a microparticle may not itself possess a dipole, but instead, experience a dipole because of surrounding conditions. For example, a ferrofluid, a colloidal solution of magnetizable materials, may fluidically surround a microparticle. One or more magnetic fields are then formed or applied adjacent said fluid and microparticle to induce a uniform dipole orientation of the magnetizable material. Such alignment may be used to entrap the microparticle such that if such now magnetized material is moved in bulk, the microparticle, being entrapped therein, is likewise moved. Thus, a microparticle may achieve a dipole equivalent by the character of its surrounding environment.

Levitating microparticles may vertically oscillate their position in the z-axis above a levitation surface by spring-like action. For example, in FIG. 9A, microparticle 901 levitates above levitation surface 905 defined by substrate 907, where microparticle 901 moves up and down as shown by arrow 903. Such movement may be initiated by kinetic energy being introduced into the system, for example by external vibration to the whole apparatus, or by magnetic or electric fields from drive or bias elements. The movement behaves much like a weight lifted by a spring, where the weight is perturbed in the axis of the spring to cause an oscillating movement to occur. Such movement may continue on for extended periods of time since the microparticles are levitated. In preferred embodiments of the invention, such oscillatory movement energy may be removed by the system by employing dampening measures. For example, FIG. 9B depicts a preferred method of removing energy from microparticle-substrate relationship (z) by interposing between microparticle 901 and substrate 907, dampening layer 909, which in preferred embodiments, is made from a non-magnetic conductor such as aluminum. Conductive layer 909 works to remove energy from moving microparticle 901 by converting the kinetic energy of the moving magnetic microparticle into electrical energy because moving a magnetic field caused by microparticle 901 near a conductor will motivate eddy current flow in such a conductor by swirling such currents around the conductor so the conductor, which may optionally be grounded, or ungrounded such that the conductor's internal resistance damps out the currents thereby dampening the motion of the microparticle.

Figure 9A:
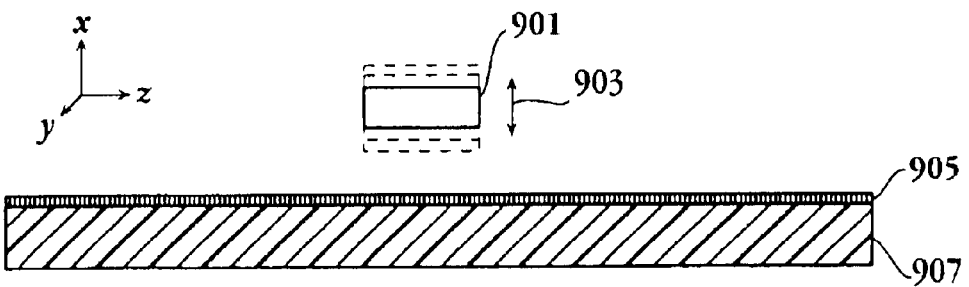
FIGS. 9A and 9B depict the effects dampening effects of a metal layer interposed between a levitating microparticle and a diamagnetic surface.
Figure 9B:
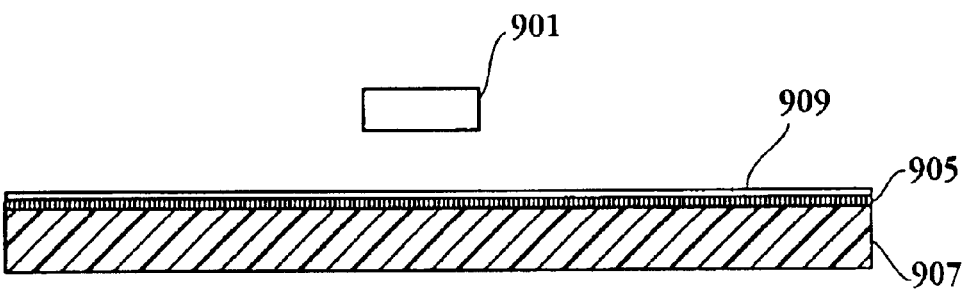
Figure 10A:
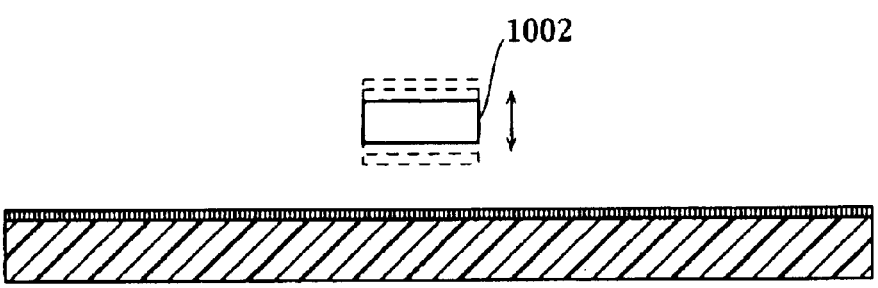
FIGS. 10A and 10B depict the dampening effects of a fluid on a levitating microparticle.
Figure 10B:
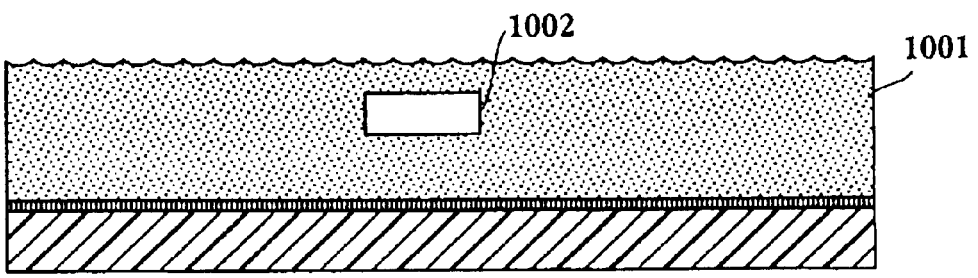

FIG. 10A again depicts an oscillating microparticle 1002 as in FIG. 9A. FIG. 10B, however, dampens the z-axis movement of the microparticle by levitating the microparticle in fluid media 1001, which by its viscosity, removes kinetic energy from the microparticle thus stabilizing the microparticle's movement in at least the z-axis. In some embodiments of the invention, the entire system where the microparticles move is filled with one or more liquids and the microparticles move from one liquid to another. In other embodiments, the microparticles may move through gas media prior to and in between regions of liquid media. In still other embodiments, the microparticles may move through gas media with only the microparticle's effector region being exposed to liquid media. In yet other embodiments, microparticles may move in or on a conveyance liquid medium where the effector is not exposed to the conveyance liquid media, but is exposed to other, different reactant media. Damping means are described with respect to damping vertical motion but can also be employed to damp horizontal motion in the x-y plane, for example to achieve more stable control of the x-y motion at high speeds using the drive elements.

Figures 11A, 11B:
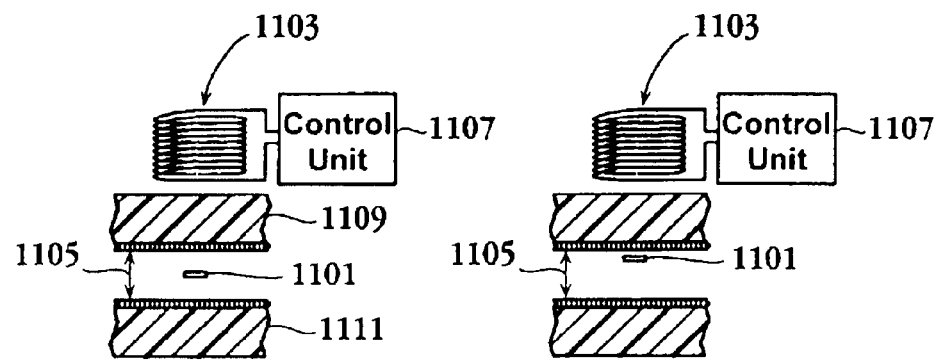
FIGS. 11A and 11B depicts a cross-sectional view of the effect a biasing element has on the Z coordinate position of a magnetic microparticle levitating between two opposing diamagnetic substrates.

Microparticle movement in the Z dimension can occur as the result of attracting or repelling forces caused by drive elements, or may be caused in some embodiments by biasing elements. To achieve active biasing in certain embodiments, a control unit may communicate with particular biasing elements to control the z-axis position of microparticles adjacent such controlled biasing elements. For example, FIGS. 11A and 11B depicts a cross-sectional view of the effect of a biasing element under the control of a control unit. FIG. 11A depicts the z-axis position of microparticle 1101 levitating between two opposing diamagnetic substrates 1109 and 1111, adjacent biasing element 1103 in workplace 1105. Biasing elements 1103 may be circular coils or they may be elongated coils, for example, depending on the desired motions. FIG. 11B depicts the effect of biasing element 1103 activation by control unit 1107 has on the Z coordinate position of microparticle 1101. Some of the biasing elements maintain a fixed bias, whereas others may be varied in their biasing by a control unit.

Figure 12:
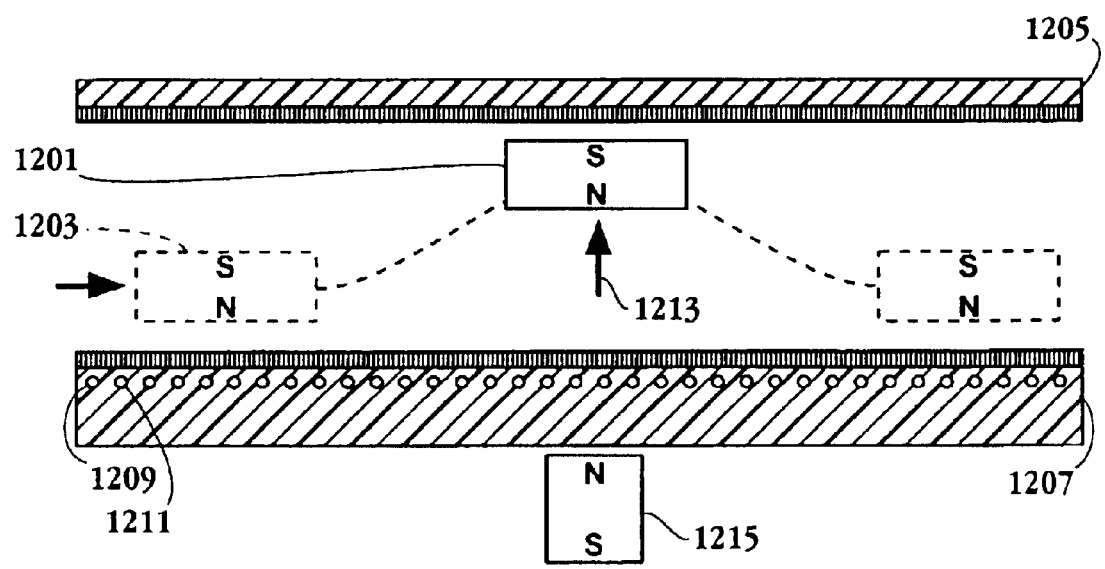
FIG. 12 depicts the effect of a passive biasing element on a passing by microparticle.

Biasing elements may be located adjacent a levitation substrate. In some embodiments, a biasing element may be embedded in a levitation substrate, in other embodiments, the biasing element may be located on the side of the levitation substrate opposite the workplace, or the biasing element may be located in the workplace adjacent a levitation substrate. In yet other embodiments, biasing elements may be employed to cause a traveling microparticle to switch tracks on the same or on different substrates, or to enter or leave a station. FIG. 12 depicts microparticle 1201 moving through workplace 1203, parallel to levitation substrates 1205 and 1207 while being ushered along by drive element circuits 1209 and 1211. At midpoint 1213, microparticle 1201 moves away from substrate 1207 and towards substrate 1205 under the influence of biasing element 1215 because of biasing element 1215 having a dipole orientation in parallel to that of at least a portion of microparticle 1201. Such biasing elements may be fixed, or variable in their output and ability to move an adjacent microparticle. In preferred embodiments, a biasing elements is used as an attracting biasing element to cause a microparticle to move in a direction towards such an attracting biasing element as shown in FIG. 12. In some embodiments, it may be desired to flip a microparticle over by reversing the polarity on biasing element 1215 and placing it below substrate 1205 to make it a repelling bias rather than an attractive bias.

Microparticle biasing may be used to hand off a microparticle from one substrate's drive elements system to another, adjacent substrate drive element system. As described above, biasing may be used for immersing a microparticle into a well, or for removing a microparticle from a well. Biasing elements may be used for introducing a microparticle to a conveyance system formed by drive elements within a substrate, or may be used to remove a microparticle from such system. Biasing elements may also be used to move microparticles in lateral or x, y directions as well as in z directions. A pair of biasing elements may flank the entrance of a well having side port access, where such biasing elements are used to propel a microparticle into or out of the well, such microparticle coming from or returning to a conveyance system, respectively. Biasing may by used to move a microparticle that is traveling in a conveyance system over other retained microparticles being held in laboratory stations adjacent the conveyance system. Biasing may also be used to place microparticles onto shelves within the workplace for storing such microparticles.

In many embodiments, microparticle locomotion results from forces acting upon a resting or moving microparticle to alter the microparticle's velocity and/or direction. FIGS. 13A and 13B depict the relation between a microparticle's dipole orientation and an activated drive element adjacent a levitation substrate. FIG. 13A depicts microparticle 1301 having a dipole parallel to the substrate surface moving towards a position directly above activated drive element 1303 so that the field lines of microparticle 1301 align with the field lines created by activated drive element 1303. In comparison, FIG. 13B depicts microparticle 1305 having a dipole oriented normal to the substrate surface moving towards a position offset from activated drive element 1303 such that the field lines of microparticle 1301 align with the field lines of caused by drive element 1303.

Microparticle movement caused by activation of drive elements may be perpetuated by sequentially activating drive elements along a selected path. As one drive element deactivates, and therefore releases the adjacent microparticle, a near-by or next drive element activates and pulls the microparticle towards the now activated drive element. This process may be repeated to perpetuate movement of the microparticle along the selected path of sequentially activated drive elements. In contrast, a drive system may operate by repelling microparticles from activated drive elements to move towards a position adjacent a non-activated drive element that, consequently, does not repel the microparticle. In yet other embodiments, a combination of attracting and repelling may be used to navigate or usher a microparticle along a selected path through the apparatus.

FIGS. 14A through 14C depict the relationship between particular dipole regions within a multi-layered microparticle, however, a single dipole microparticle will behave similarly. It should also be noted that although N and S are used to generally refer to magnetic north and south, each are interchangeable. Furthermore, in many embodiments, N and S may also be used to describe opposite electrical polarities. FIG. 14A shows microparticle 1401 levitating above substrate 1405 in workplace 1407 positionally maintained by activation of drive element 1409a and maintained at a selected distance from second microparticle 1411 that is positionally maintained by drive element 1415a. Microparticle rotation in the x, y plane is limited by additional dipole regions 1425 and 1427 oriented parallel to the plane of substrate 1405 which are affected by additional activated drive elements 1417a and 1419a. Drive elements 1417 and 1419 have currents going in the opposite direction as 1409a–c and 1415a–c. FIG. 14 denotes currents going into the Fig. With an "x" and denote current coming out of the Fig. With a "dot". FIG. 14B depicts forward movement of microparticles 1401 and 1411 by deactivating drive elements 1409a and 1415a, and activating 1409b and 1415b which, in-turn, cause microparticles 1401 and 1411 to move to the right such that dipole regions 1403 and 1413 center above drive elements 1409b and 1415b, respectively. Movement is further perpetuated by the deactivation of drive elements 1409b and 1415b and the activation of drive elements 1409c and 1415c which move microparticles 1401 and 1411 to position dipoles 1403 and 1413 over drive elements 1409c and 1415c, respectively. Corresponding to the positional shifting of activated drive elements 1409a–c and 1415a–c are the sequential activation and deactivation of flanking drive elements 1419 and 1417. Thus, the shifting of the pattern of activated drive elements separated by two deactivated drive elements along the path of travel causes microparticles to move along the path in an oriented and spaced-apart manner.

Figure 15:
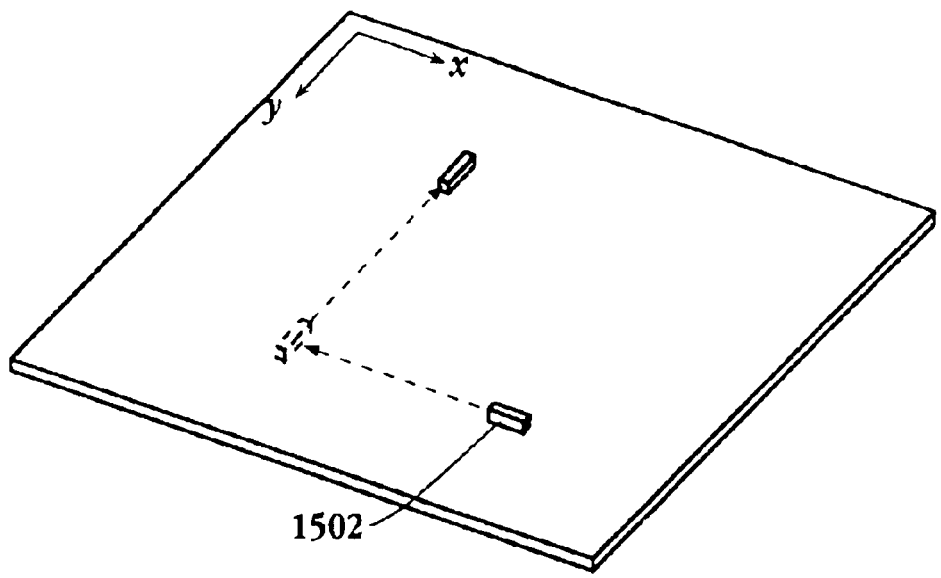
FIG. 15 depicts a perspective view of the movement of a magnetic microparticle across the surface of a diamagnetic substrate in two dimensions.

In some embodiments of the invention, a microparticle may be moved about between x and y coordinates by indirect pathways. For example, FIG. 15 depicts a microparticle 1502 moving first in an x direction, and then moving in a y direction to move the microparticle between x and y coordinates. Such movement may by carrying out by a single-track system, or by a two-track system where at some point, the microparticle is handed from the first track to the second track for further movement between x and y coordinates. In other embodiments of the invention, each x and y coordinate has its own independently addressable drive element and/or biasing element in communication with a controller to move microparticles about an x, y plane in user defined directions and patterns. Details of this embodiment are provided below.

Movement of microparticles may be completely controlled, as described above, or may be partly controlled, and partly ballistic. For example, a microparticle may be accelerated by movement along a path of drive elements, and allowed to continue along the trajectory of the path without the assistance of drive elements. During such "free flight", the microparticle moves in a straight line unless external forces perturb the microparticle's trajectory. For example, the microparticle may, after a period of ballistic travel, be picked up by another set of drive elements defining a pathway that may further accelerate the microparticle, decelerate the microparticle, or may change the direction of travel of the microparticle. In other embodiments, a microparticle may be accelerated by a drive element, or a biasing element to enter into a liquid, where upon entry into the liquid, the drive element or biasing element is deactivated and the microparticle is decelerated by the viscosity of the liquid medium. In this embodiment, the liquid medium serves the same function as a drive element to control the movement of the microparticle by deceleration.

Figure 16:
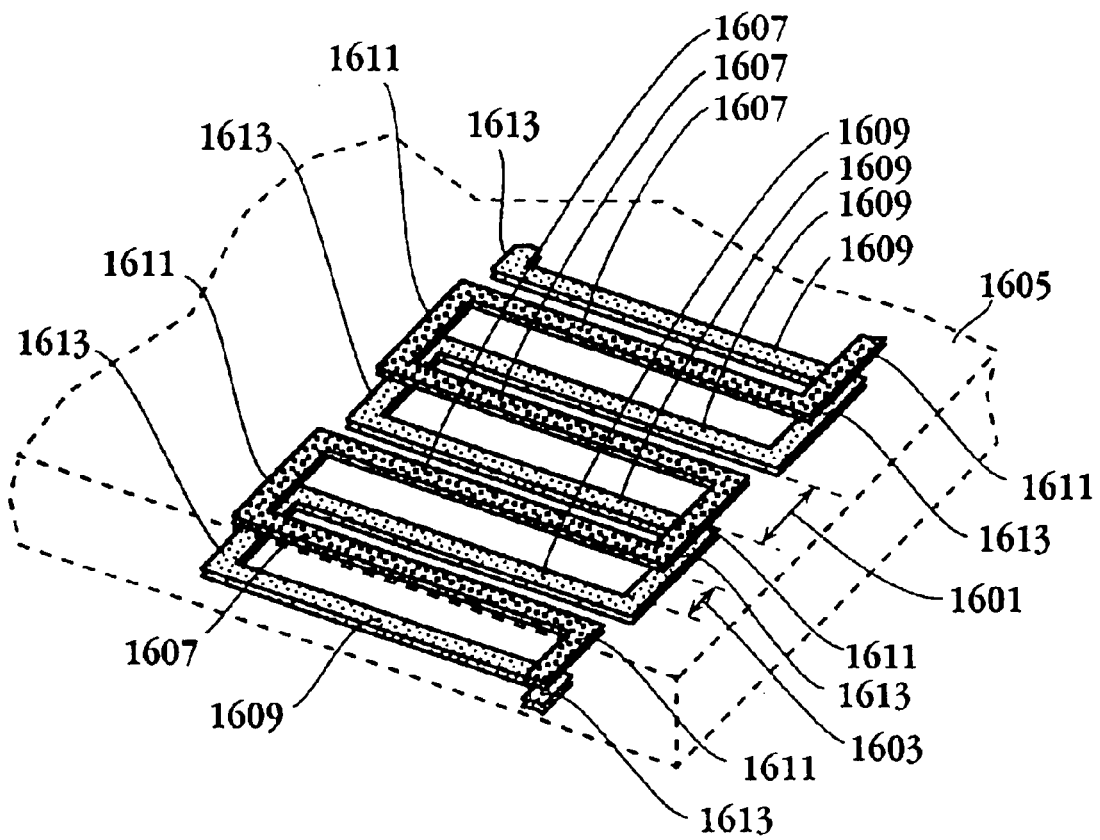
FIG. 16 depicts a perspective view of a drive element embedded in a driving structure.

In preferred embodiments, microparticle movement within the workplace results from the controlled activation and deactivation of drive elements and/or biasing elements. A particularly preferred drive element configuration employs a minimal number of drive element circuits to form a track. FIG. 16 depicts a two-drive element serpentine track formed from printed circuit board traces. A first drive element circuit is formed from circuit elements rungs 1607 and rails 1611 and a second drive element circuit is formed from circuit element rungs 1609 and rails 1613 formed in substrate 1605. Each drive element makes a repeating spatial pattern on the substrate, such as a repeating square wave pattern. Electrical current is selectively applied to each drive element circuit to induce magnetic fields in the traces. When driven by an electrical current, each rung of a drive circuit has a current flow in the opposite spatial direction as the next rung of the same circuit. However, the magnetic fields generated by two consecutive rungs are not opposite at a point between the two consecutive rungs. Each drive element circuit is geographically offset from the other by a selected distance or phase angle.

In some preferred embodiments, the spacing of the rungs of each drive element circuit corresponds to the spacing of dipole regions within the microparticle such that the rungs of a drive element circuit will maximally influence microparticle positioning. Each of the two drive elements, in the preferred embodiment are depicted in FIG. 16 as off-set or out of phase from each other by 90 degrees. That is, the two spatial square wave patterns defined by the two traces are shifted by a spatial phase of 90 degrees. This arrangement allows the secondly activated drive element to attract a microparticle once held by the first activated drive element circuit. In a preferred embodiment, the two driving traces are driven with bipolar electrical currents (the currents reverse direction). If both driving elements are driven initially with a positive current, the spatial square wave the patterns of current on the substrate will create a repeating magnetic field pattern. The microparticle will move to its lowest magnetic energy state relative to the field pattern (assuming no other fields affect the motion along the driving element path). For a single dipole magnetic microparticle, for example, the microparticle will move to the part of the field pattern where the field lines up with the dipole. If now the electrical current in a first driving element is reversed from positive to negative, the field pattern will shift 90 degrees in spatial phase (it will shift a distance equal to half the distance between two consecutive rungs on a single drive element). This causes the lowest magnetic energy position of the microparticle to likewise shift, causing the microparticle to move an amount and direction equal to the shift. If now the electrical current in the second driving element is reversed as well, the magnetic field pattern will shift another spatial 90 degrees in the same direction as the first shift. The microparticle will likewise shift to reach the new magnetic equilibrium point. The microparticle can be shifted again by changing the electrical current back to positive in the first drive element, and still another 90 degrees shift can be obtained by finally switching the second drive element to a positive current. The currents in both drive elements are now positive as they were at the beginning, but now the microparticle has shifted 360 spatial degrees (it has advanced twice the distance between two consecutive rungs on a drive element). If denoting the current polarity for drive element 1 and 2 by the notation {+, +} indicating both polarities are positive, then the control sequence to move the microparticle is {+,+}, {−,+}, {−,−}, {+,−}, {+,+}. The reverse direction of motion is caused by executing {+,+},{+,−},{−,−}, {−,+},{+,+}.The microparticle so controlled can be moved along the path defined by the driving elements, or it can be stopped anywhere along that path by simply holding the current configuration when it has reached its desired location.

In some embodiments, the offset in the phase angle motivates a microparticle movement in one direction rather that simply oscillate back and forth between positions, the second drive element circuit is pulsed to accelerate the microparticle towards it, the deactivated to allow the microparticle to pass by ballistically towards the next rung in the first drive element circuit. Accordingly, the first drive element circuit is used to hold microparticles in position, and the intervening rungs of the second drive element circuit are used to accelerate microparticles between first drive element circuit rungs. By offsetting the second drive element circuit rungs away from the subsequent first drive element circuit rungs, and toward the initial first drive element circuit rungs, the second drive element circuit rungs act to move the microparticles from the initial first drive element circuit rungs towards the subsequent first drive element circuit rungs, thereby moving the microparticle in the direction of the subsequent first drive element circuit rungs. In other embodiments, the phase angle of the drive elements may vary along a track length, or different tracks may have different phase angles, or all of the tracks may have a different phase angle than 90 degrees or 180 degrees. In yet other embodiments, more than two drive element circuits may comprise a drive track. In some embodiments, the rate of oscillation between drive element circuits is fixed, yet in other embodiments it may be selectively variable. In some embodiments, the amplitude of the voltage or current supplied to the drive circuits may be fixed, square wave, sinusoidal, or some other waveform, may be ac, dc, with or without bias.

Figure 17:
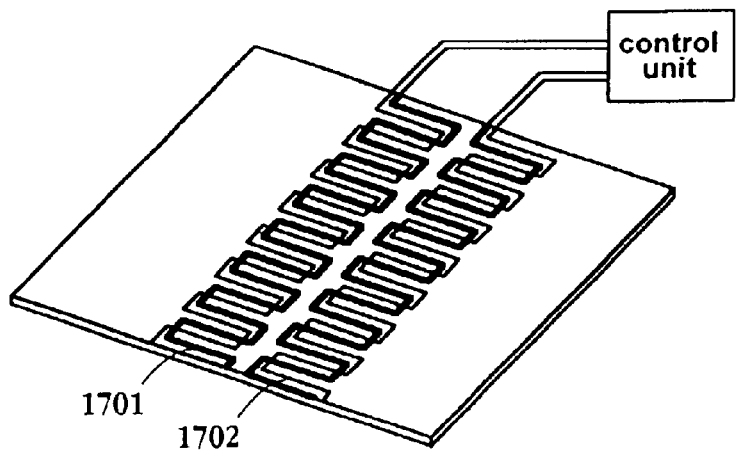
FIG. 17 depicts a square wave serpentine track.
Figure 18:
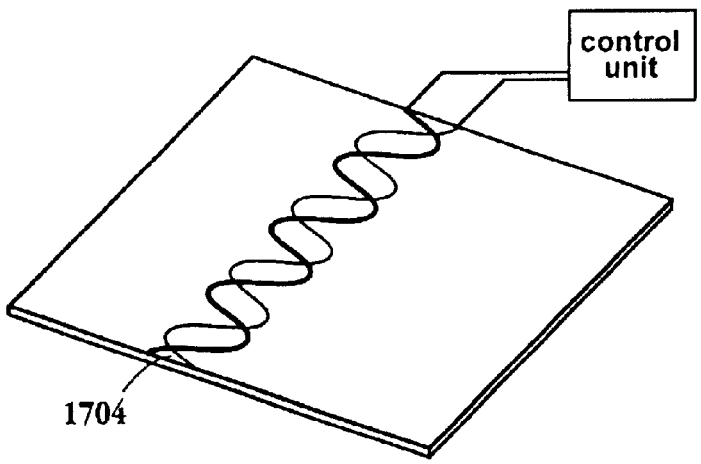
FIG. 18 depicts a sine wave serpentine track.

Different drive element circuit configurations may be used. Particularly preferred embodiments employ offset-square wave-like patterns such as patterns 1701, 1702 depicted in FIG. 17, where multiple tracks run along side one another. FIG. 18 depicts a sinusoidal type track pattern 1704. Different track layouts may be combined to achieve different objectives.

Tracks may be open or closed. Open tracks have a beginning portion and an end portion, with a track distance there between. Closed tracks form a closed circuit capable of circulating and re-circulating a microparticle along the track path.

A drive system may include more than two sets of drive element circuits. Drive systems may further comprise overlaying circuits where each circuit is formed from one of several circuit trace layers in a printed circuit board. Different tracks up to N tracks may overlap at selected angles to each other to provide N degrees of freedom of microparticle movement. The control of the electrical currents for the drive system may use dual polarity square wave current switching, dual polarity sine or other shaped wave currents, or single polarity currents with various embodiments.

Figure 19A:
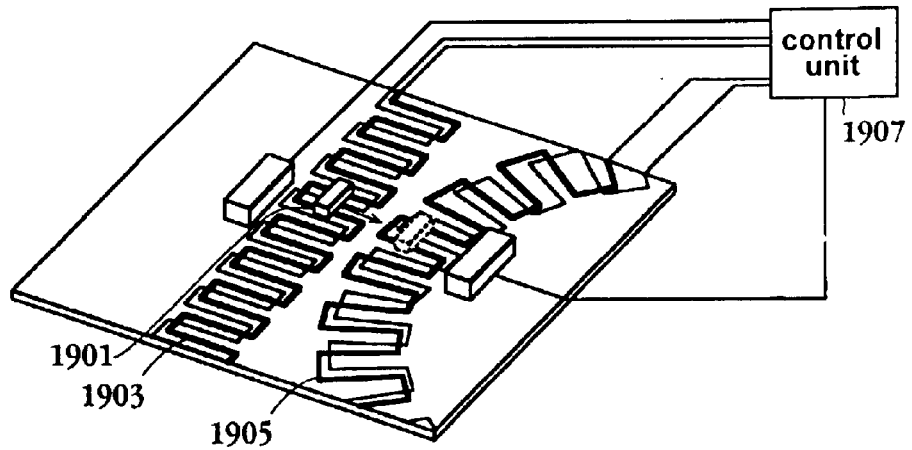
FIGS. 19A–C depict two adjacent tracks with a microparticle switching tracks.

A microparticle may, for example as in FIG. 19A, switch from a straight track 1903 running near an arc of a second curved track 1905, to that second track. Microparticle 1901 is shown in FIG. 19A as switching from the linear track 1903 to the curved track 1905 under control by the controller unit 1907. Track or conveyance circuit switching may occur by passing a microparticle on a first track having a first lower degree of attraction for the microparticle by a second track which has a greater attraction for the microparticle, to cause the microparticle to leave directional control of the first track and become directionally controlled by the second track. After switching tracks, the microparticle then proceeds along the path of the second track. In other embodiments, a microparticle may be accelerated such that it develops achieves an escape velocity and tangentially leaves one track to ballistically continue onto a second track which then decelerates the microparticle to maintain control over the microparticle. In other embodiments, track switching may be caused by the activation of a biasing element adjacent a junction of two tracks to cause a microparticle traveling along the first track to be attracted onto the second track, or repelled off of the first track onto the second track, or a combination of both if two or more biasing elements are employed.

The speed at which a microparticle may move along the path of a track is dictated, in part, by the geographical layout of the track, and the speed at which the drive elements are switched. By varying the spacing of the track rungs along a track path, a microparticle may be accelerated or decelerated based on its position along such path even though the drive elements are switched at a constant rate. For example, a track path may have a first region having a first rung spacing which achieves a first microparticle movement speed when activated, and a second region having a second rung spacing which achieves a second microparticle movement speed. In other embodiments, different drive element track layers may be superimposed on top of one another such that different microparticle speeds may be realized within the same region of the workplace by activating different superimposed tracks. Printed circuit board technology for making tracks, for example, can contain up to 30 layers, allowing a wide range of system configurations.

Figure 19B:
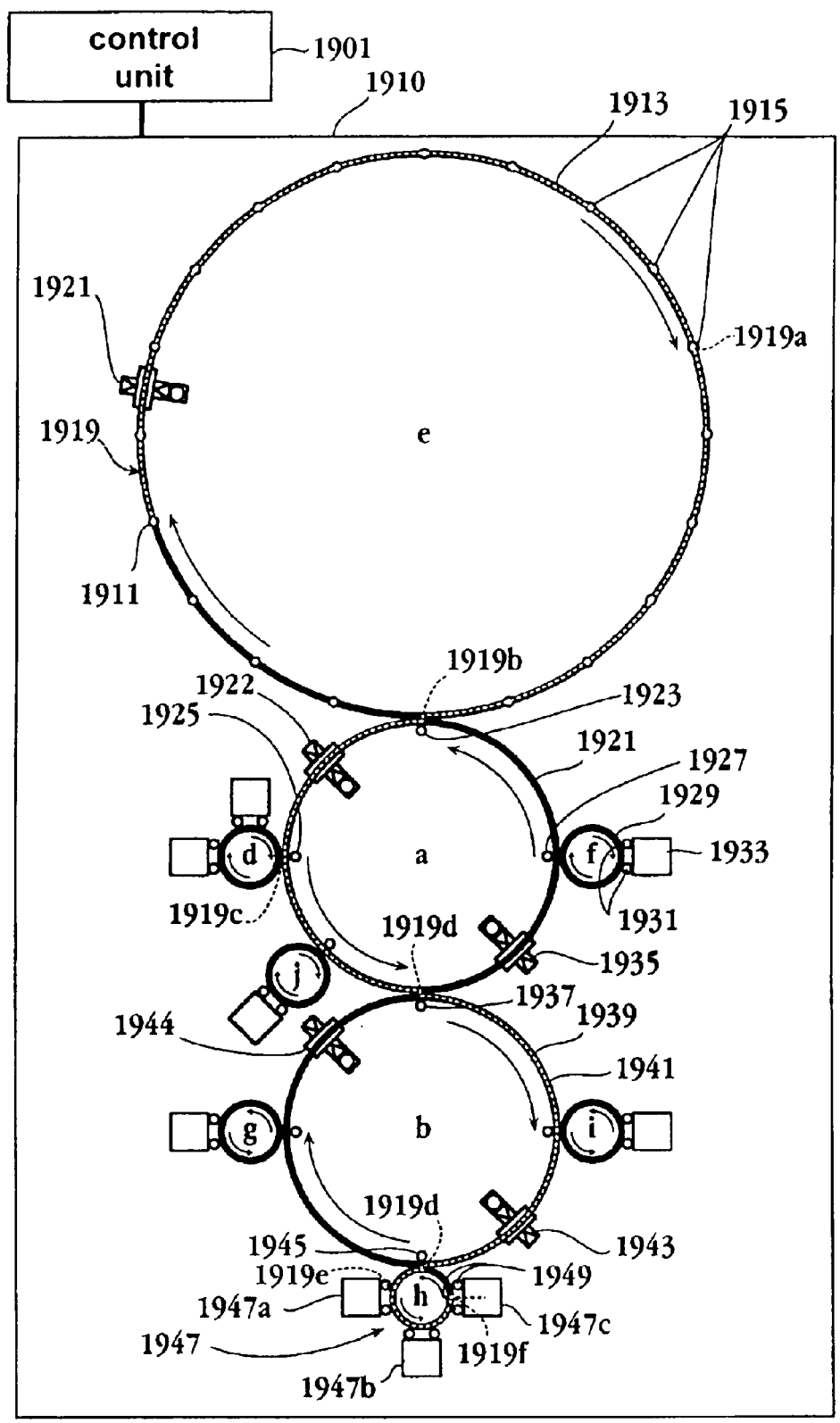

Controlling the movement of microparticles between different points, coordinates, or laboratory stations may be carried out in various ways. A particularly preferred method reduces the demands placed on the system controller by minimizing the need for microparticle location feedback to the controller by relying upon the programmed, sequential movement of a selected microparticle through the apparatus. For example, the conveyance system of the device may comprise a plurality of conveyance circuits that individually form closed loops with at least one portion of each closed loop being adjacent another closed loop such that a microparticle may be switched from one loop to the other as described above for track switching. A loop, in this instance, is a closed track. A central loop may be used to interconnect distal arm loops to one another where each distal arm loop connects another central loop, a distal loop, or a laboratory station. In FIG. 19B substrate 1910 having a plurality of drive element circuit loops 1913*a–i* where loops 1913*a* and 1913*b* are central loops connected by distal arm loop 1913*c*. Distal arm loops d, f, g, h, and i are all connected to laboratory stations. Distal arm loop e has along its track a plurality of biasing elements adapted to selectively remove passing by microparticles and hold such microparticles until selectively released into the system of loops and other activities. Loop 1913*e* can hold a plurality of microparticles simultaneously by using holding biasing elements 1915 to hold microparticles when selectively activated while permitting other microparticles to pass by each held microparticle along the loop 1913*e*, releasing selected microparticle (s) into the system of loops to distribute and/or deliver such microparticle(s) to a selected location away from the microparticle's holding position within loop 1913*e*. In some preferred embodiments, a held microparticle's holding position is located away from the track so that the field from the held microparticle to reduce interference with a different passing microparticle, where a hold-off distance is at least 5–10 microparticle diameters away from the passing microparticle, and more preferably 20 diameters. The microparticles are held a sufficient distance away from the passing microparticles so that the dipole fields of the held and passing microparticles do not interfere with the motion. The required hold-off distance depends on the specific microparticle geometry and dipole configuration (in the case of microparticle dipole arrays), but typically is 5–25 times the diameter of the micro microparticle, and more preferably is 10–20 times the diameter. Microparticles made of dipole arrays can generally be held closer to passing microparticles because the fields from the different dipoles in the held microparticle's array can cancel to a significant degree (e.g. up polarities tend to cancel down polarities and the field therefore does not project as much with distance as if they were all the same polarity). Likewise, each station may be able to retain a microparticle after it has been delivered to such station while permitting other microparticles to pass by along the same loop adjacent such laboratory station. In short, loop e is used to inject a microparticle into the system. The other loops are used to convey such microparticle to a selected destination within the apparatus along a selected pathway of loops.

A microparticle's location, in some embodiments, is traceable by several different devices within the system. For example, an optical sensor may detect a passing by microparticle by such microparticle interrupting the optical path of a light source to a detector. More sophisticated systems may read or detect codes embedded in or on the microparticle so that both the identity and position of a microparticle may be determined. Other embodiments may use inductive devices, including biasing elements or drive elements, configured at least transiently to detect the movement of a magnetic microparticle by placing a conductor adjacent such moving magnetic microparticle's path of travel, and detecting the induction of current flow in such conductor. Inductive detection does not rely on optical detection. Similarly, magnetoresistive materials, such as use in disk drive heads, or Hall effect sensors, may be used to detect the magnetic field of a passing magnetic microparticle.

FIG. 19B depicts an exemplary embodiment of a multi-microparticle system integrating loop conveyance with minimal microparticle tracking or feedback requirement. In FIG. 19B, detector 1917 is adapted to detect the passing by of a microparticle. In operation, all of the microparticles in the system are initially each individually held in position by biasing elements 1915 such that any circulating microparticle circulating along loop 1913*e* may pass by the held microparticles without interfering with each other. Thus, loop 1913*e* in conjunction with its biasing elements 1915 act as a "parking garage" for each microparticle until it is summoned by controller 1901 for use in carrying out a laboratory activity. Controller 1901 is in communication with each loop, biasing element, laboratory station, and detectors 1921, 1922, 1935, 1943, and 1944. To begin processing microparticles, controller 1901, while operating simultaneously operating each of the loop's conveyance systems, deactivates one of biasing elements 1915 to release into the loop 1913*e* conveyance system a microparticle, not shown, once held at 1911 biasing element's position. At the same time, biasing elements 1923, 1937, and 1945 are activated to create laboratory route 1919 for the now circulating first microparticle to arrive at loop 1913*h* of lab station cluster 1947 and one of its laboratory stations, 1947*c*. The first microparticle first circulates about loop 1913*e* along route segment 1919*a* until it encounters biasing element 1919*b* that directs the microparticle onto loop 1913*a* where the microparticle again encounters another biasing element 1919*d* that directs the microparticle onto loop 1913*b*. From loop 1913*b*, biasing element 1945 directs the microparticle onto loop 1913*h* from which the microparticle is further directed by biasing element pair 1949 into laboratory station 1947*c* and held for processing. In this embodiment, each laboratory station can provide feedback as to whether a microparticle is housed within it. Consequently, the completion of the first microparticle's journey from its original held position in loop 1913*e* to its current position in loop 1913*h*'s laboratory station 1947*c* is signaled to controller 1901 which may then direct the travel of a second microparticle to a different destination.

Upon completion of the selected laboratory activity in laboratory station 1947c, the first microparticle may be transferred to another laboratory station for further processing by using a similar scheme of loops and biasing elements with detection of arrival at the second selected laboratory station being relayed to the controller. Return of a microparticle back to its original position in loop e may be carried out by again routing the microparticle's travel by loops with biasing elements as shown in FIG. 19B by the darkened loop lines by reversing the action of the activated biasing elements used for setting up the route. In preferred embodiments, loop travel directions are in opposition to one another for each abutting loop. In this regard, each of the biasing elements behave in a manner similar to track-switches in a railroad train-track system to direct microparticles to different legs or loops of the system.

Embodiments, such as the one depicted in FIG. 19B, are ideally suited for minimal or non-feedback control loop systems. Because movement of microparticles is dictated by the establishment of a route caused by the selective activation of certain biasing elements, microparticle travel is predetermined to travel such a route without any monitoring. Since travel characteristics are known and predictable, system timing dictates microparticle activity.

In some embodiments, microparticle code readers are used to scan each microparticle to verify its particular identity. Such identification may be important to insure system fidelity, as well as identify particular microparticle without regard to their position within the system. Such identification is useful, for example, when microparticles may be separated from the apparatus for further external processing.

Figure 19C:
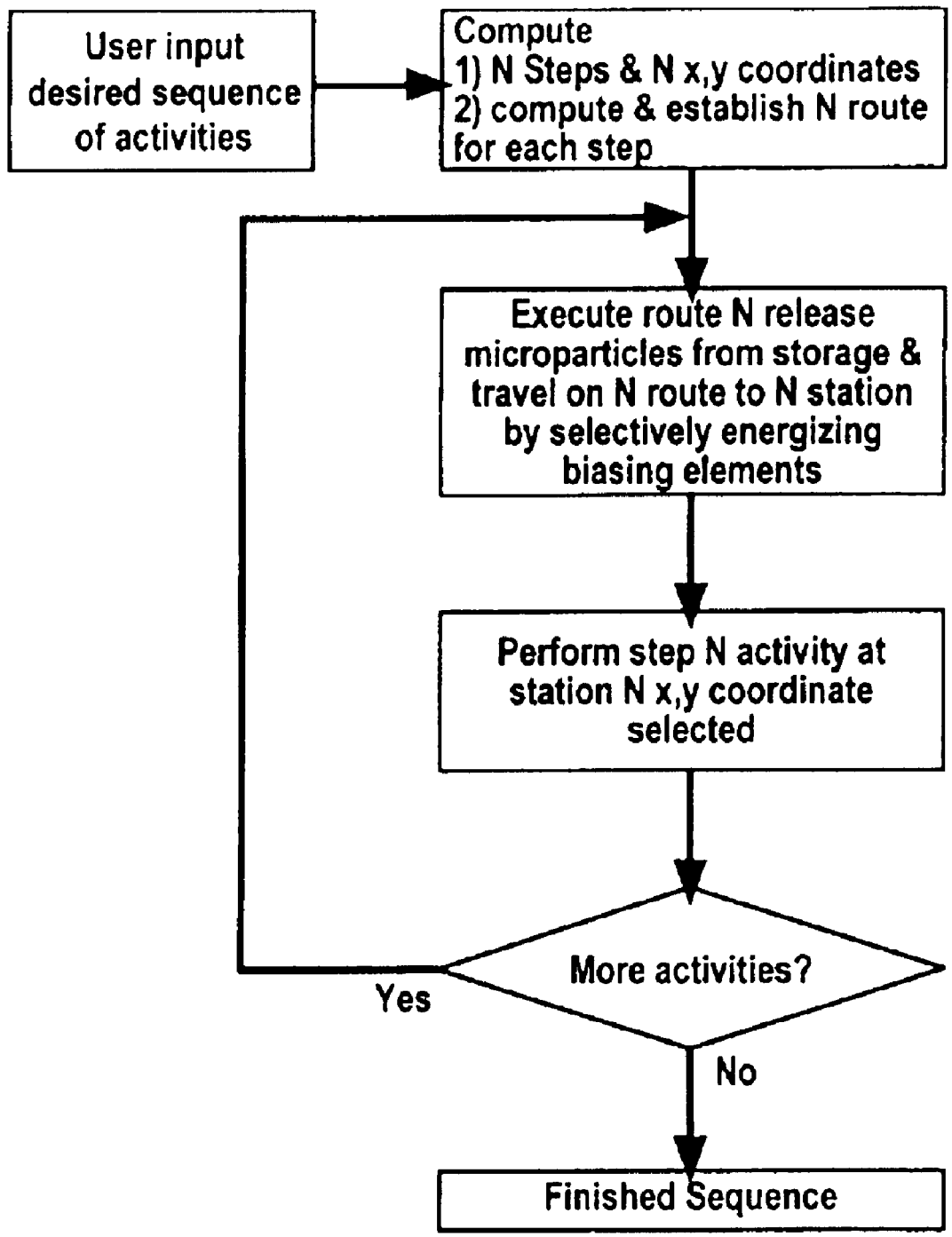

FIG. 19C depicts a flowchart for operating certain embodiments of route forming apparatuses for carrying out a desired sequence of activities using such apparatus.

In another aspect, the invention provides for methods and devices for selectively assembling a plurality of microparticles in trains or platoons for bulk movement of such microparticles through the apparatus. For example, there may be inter-connections between a "locomotive" microparticle and "rolling stock" microparticles such that only the locomotive need be navigated through the device while the "rolling stock" follows behind. Trains may be moved in a forward, head to tail, direction, or they may be moved as a platoon in a direction perpendicular or at some other angle to the head-to-tail arrangement of the train. In other embodiments, some or all of the microparticles in the train are moved by the biasing or drive elements to cause the microparticles to move in a "train-like" fashion. In other embodiments, microparticles may move in a spaced-apart arrangement or in-contact with one another by the parallel control of drive elements and/or biasing elements. Microparticles may, in some embodiments, simultaneously travel along a series of tracks where the microparticles are either spaced apart from each other, or linked together transiently as discussed above.

In some embodiments, microparticles may be loaded into the apparatus sequentially where each microparticle is individually introduced into a port of the device, and then conveyed to a holding location where the microparticle is held in place, for example, by a biasing element. In other embodiments, microparticles may be loaded in parallel where such microparticles are held in a spaced apart manner by a holding device, and then brought into proximity with the apparatus where they are then transferred to a transient holding region, for example, a loop having a plurality of biasing elements for holding microparticles. Once microparticles are placed within an apparatus, their position may be maintained passively by a passive biasing system such as a permanent magnetic plate that is detachable for liberating the microparticles once the apparatus is powered. In other embodiments, the apparatus is capable of retaining the microparticles in position by employing a back-up battery or powering system to supply a continuous source of power, and therefore attracting force, to the drive elements and biasing elements of the apparatus.

Figure 22A:
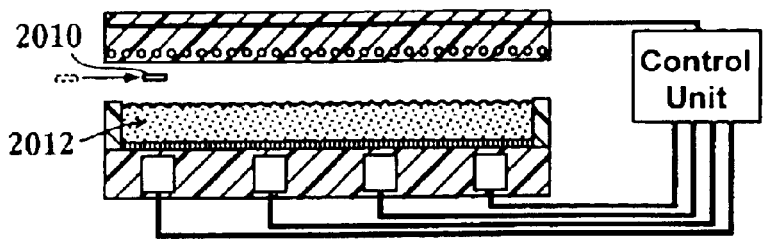
FIGS. 22A–E depict the movement of a microparticle through a workplace where the microparticle descends onto the surface of fluid contained within a reservoir, moves along the surface, and then rises above the fluid surface to continue movement through the workplace.
Figure 22B:
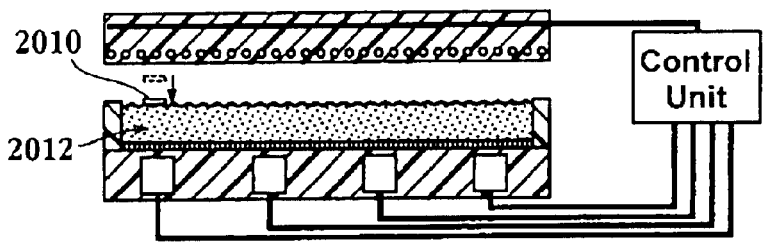
Figure 22C:
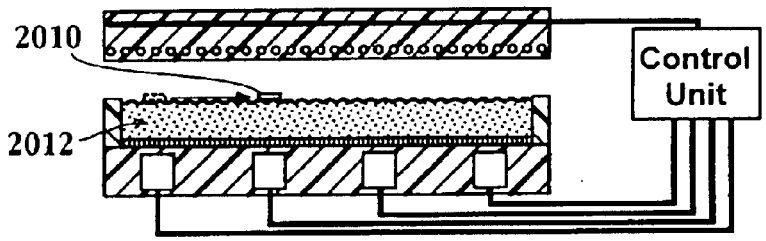
Figure 22D:
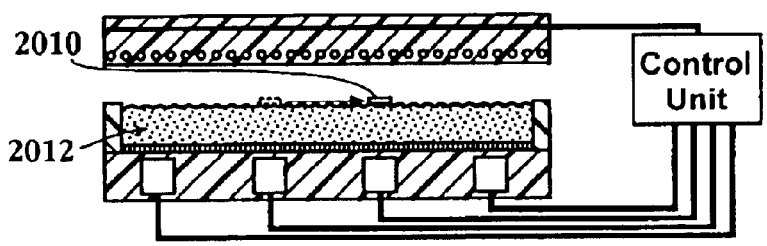
Figure 22E:
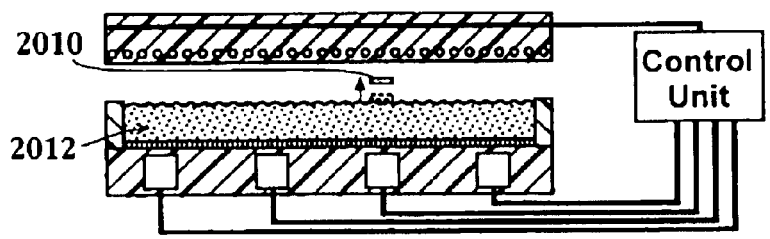

FIGS. 20A through 20E depict the movement of a magnetic microparticle 2000 across, into, and through a fluid reservoir 2002 in the lower diamagnetic substrate 2004. A microparticle may move between locations within the apparatus in a similar manner where all or some of the conveyance paths are through channels filled with liquid. In other embodiments, microparticles may move through some or all of the apparatus by floating on the surface of one or more liquid mediums contained within the device. FIGS. 21A through 21E depict a microparticle 2006 moving through a gas filled space above a liquid medium 2008. In some preferred embodiments, microparticles are moved between laboratory stations through a gas medium contained within some or all of the workplace. In yet other embodiments microparticles rest adjacent, just above or just below, the surface of a liquid medium by not breaking the surface tension of the liquid medium. For example, FIGS. 22A–E depict surface-tension levitation where a microparticle 2010 is held against the surface of a liquid medium 2012 without the microparticle contacting solid surfaces in the device by moving along the surface created by the surface tension or gas/liquid interface created by the workplace containing both a gas and a liquid, and being further ushered along the surface without crossing or moving away from the surface until such crossing or moving away is desired (FIG. 22E). Although FIG. 22E depicts the microparticle moving along the gas side of the interface, other embodiments of the invention provide for moving the microparticle along the liquid side of the interface, preferably by biasing the microparticle up against the liquid side of the interface to position the microparticle in the z axis of the device. In other embodiments, either or both gravity or a biasing element may be used to positionally maintain the microparticle in the z axis when the microparticle is moved along the gas side of the interface. In certain embodiments, the microparticle is constructed in a shape size and density, and of materials that prevent the microparticle from penetrating the interface of a liquid unless forced through the interface by the activation of biasing elements or the increased attraction or repulsion of drive elements responsible for causing the movement of the microparticle to such liquid regions.

Microparticles may be suspended by a biasing element or elements to cause such microparticle to rest against the liquid side of a liquid-gas interface, where the microparticle does not penetrate the interface, but is urged against the interface by the biasing element(s). In one embodiment, a microparticle having a single magnetic dipole is biased towards the liquid side of a liquid-gas interface by a biasing element's biasing magnetic field. The biasing element is selectively energized to lift and hold the microparticle against the surface during lateral motion along the liquid's surface, but not so strongly as to pull the microparticle free of the surface. In this embodiment, the biasing element may reduce the magnetic bias force to then allow the microparticle to sink, hold a constant bias force to hold the microparticle against the liquid-gas interface for movement along the interface using drive elements, or rapidly pulse a relatively large bias force to pop or pull the microparticle out of the liquid. In another embodiment, the microparticle may be buoyant, yet cannot escape the liquid side of the liquid-gas interface. These embodiments exploit surface tension to positionally maintain a microparticle at a given location or "altitude" within the workplace of the apparatus or device.

Figure 20A:
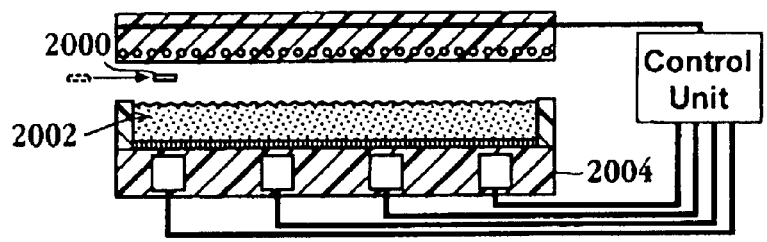
FIGS. 20A–E depict the movement of a microparticle through a workplace where it immerses into a liquid contained within a reservoir, travels through the liquid and then emerges from the liquid to continue movement through the workplace.
Figure 20B:
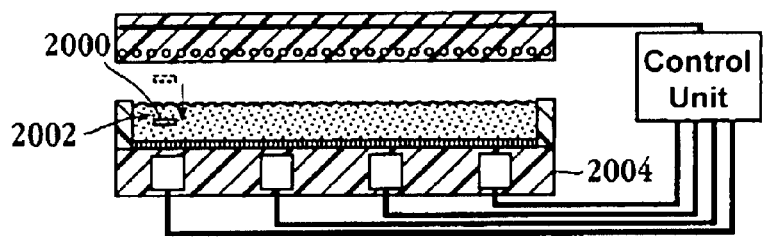
Figure 20C:
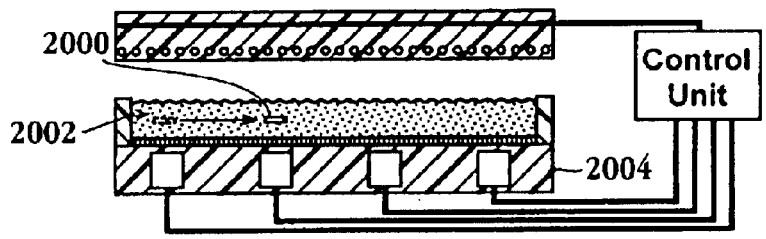
Figure 20D:
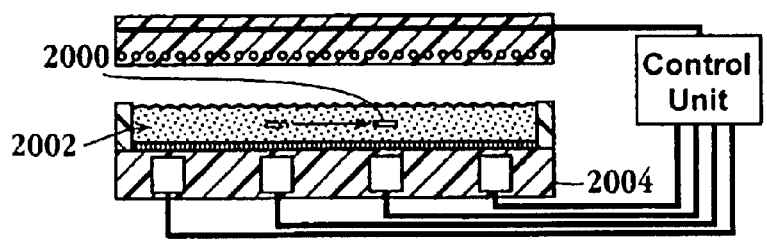
Figure 20E:
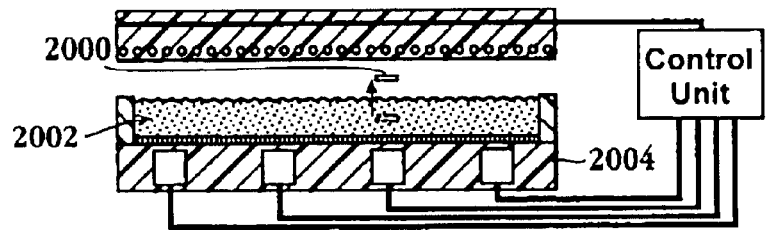
Figure 21A:
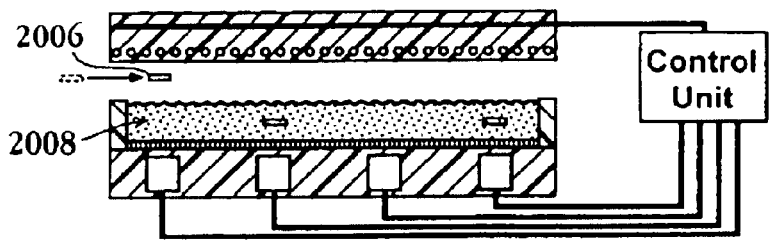
FIGS. 21A–E depict the movement of a microparticle through a workplace above a liquid contained within a reservoir.
Figure 21B:
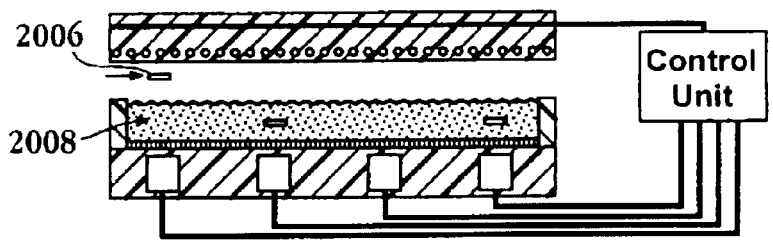
Figure 21C:
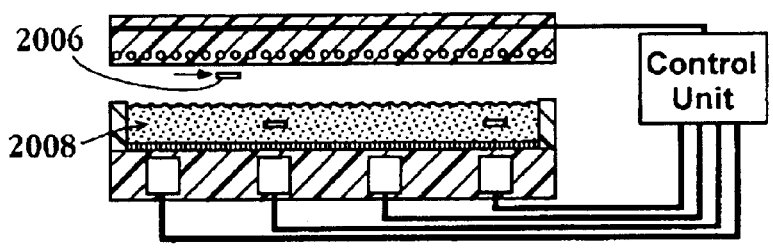
Figure 21D:
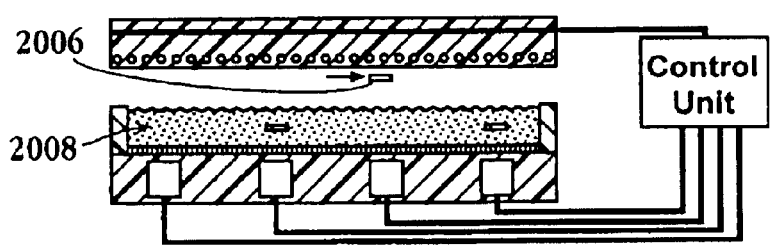
Figure 21E:
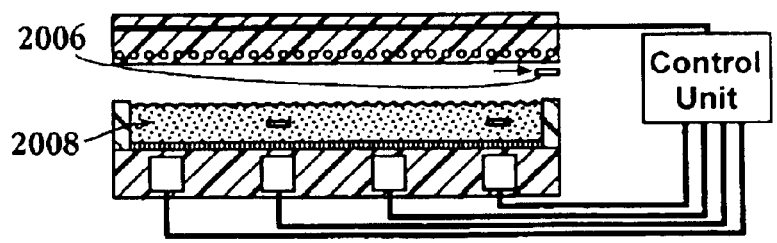
Figure 23:
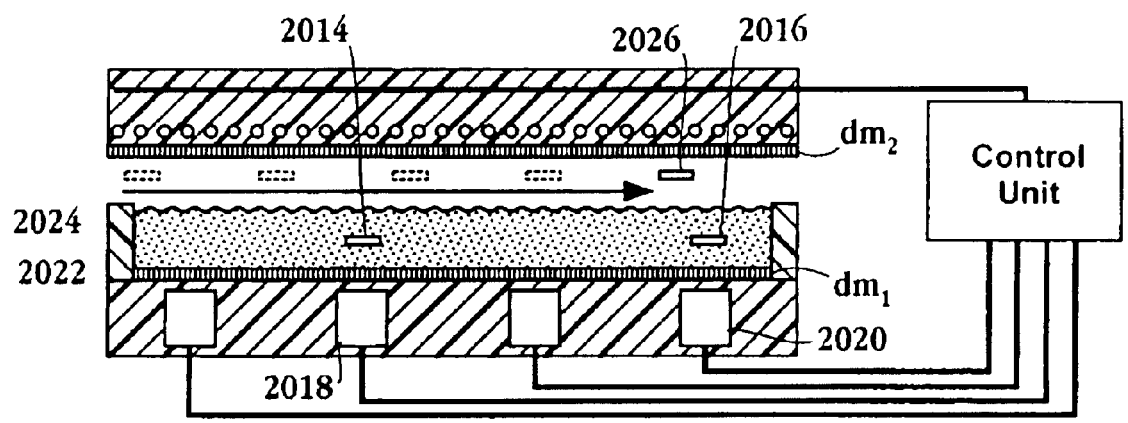
FIG. 23 depicts the movement of a microparticle through a workplace above a liquid contained within a reservoir having held therein two microparticles.
Figure 24:
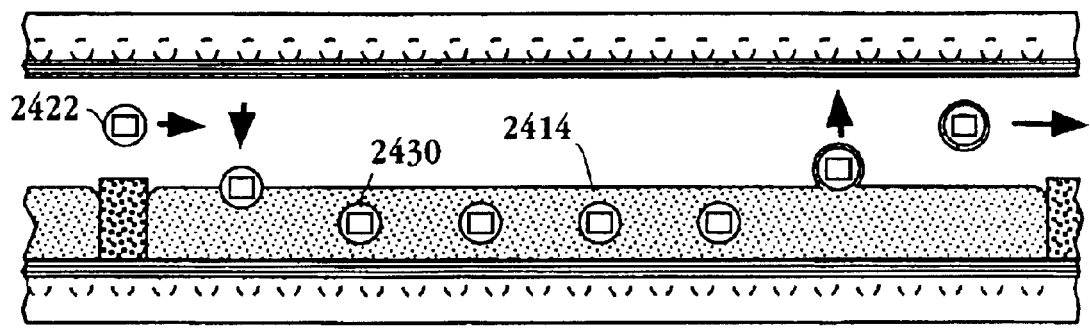
FIG. 24 depicts the placement of a plurality of microparticles at different positions within a fluid held within a reservoir within the substrate.

As discussed above, biasing elements may operate at several different modes. For example, a biasing element may energize at a first higher level to attract a microparticle away from a conveyance path as shown in FIGS. 20A and 20B. Once a microparticle is captured, the capturing biasing element is reduced in its power to attract the microparticle such that the microparticle is positionally retained, but without further attracting passing by microparticles. FIG. 23 depicts such a scenario where two microparticles 2014, 2016 are already held above two biasing elements 2018, 2020 while bathing in a liquid 2022 held in a reservoir 2024 as a third microparticle 2026 moves along the conveyance pathway above such microparticles without being attracted to such biasing elements (dm 1 and dm 2 are optional diamagnetic surfaces used when diamagnetic levitation is employed). In some embodiments, the microparticles are situated or held away from the track so that passing microparticles may pass without being significantly influenced by the held microparticles. FIG. 24 further exemplifies how multiple microparticles may be stored while reacting in a reservoir having multiple biasing elements. Microparticle 2422 is entering liquid 2414 to attain position 2430. Meanwhile, microparticles 2424 retains its position by the retaining effects of an adjacent biasing element. The process of immersing and removing microparticles from liquid media is described further below.

Figure 25A:
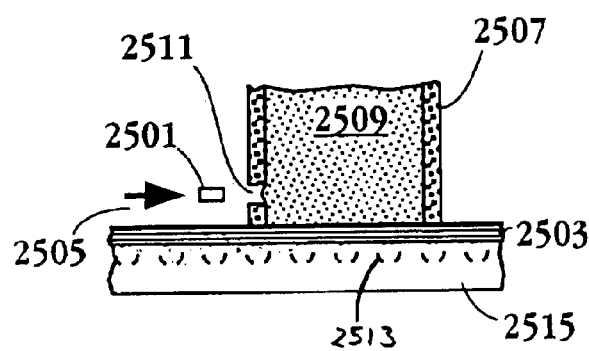
Figure 25B:
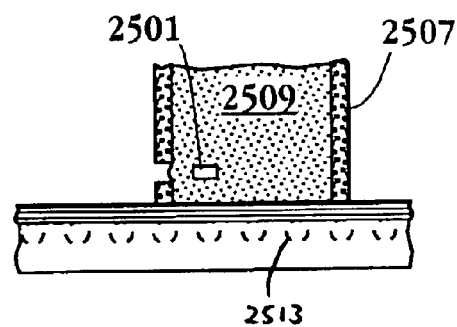
Figure 25C:
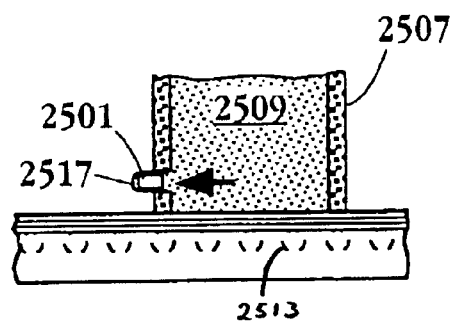
Figure 25D:
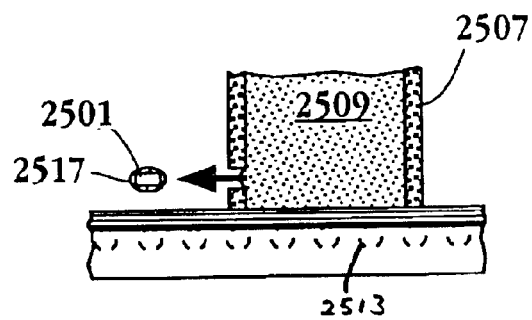

Microparticles may pass from a gaseous phase to a liquid phase by descending into a liquid, as described above, or by entering a chamber containing a liquid through a side port such as is depicted in FIGS. 25A through 25D. In FIG. 25A, microparticle 2501 levitating above surface 2503 in workplace 2505 is moved into well 2507 containing liquid 2509 through port 2511 by activated drive elements 2513 in substrate 2515, or by biasing elements at the outer opening of port 2511, not shown, and/or just inside the opening of port 2511, not shown. FIG. 25B depicts microparticle 2501 inside reservoir 2507 in contact with liquid 2509. FIG. 25C depicts microparticle 2501 leaving well 2507, taking with it a thin-film of fluid shown as 2517. FIG. 25D depicts microparticle 2501 separated from liquid 2509, but retaining the thin-film of liquid 2517. Liquid is maintained inside well 2507 despite the existence of port 2511 because of port 2511 size, shape, and material properties, especially the liquid's surface tension and wetting properties For example, it is well-know in the prior art of inkjet printing that a sufficiently small open orifice can retain a liquid using the liquid's surface tension provided the liquid does not wet the outer surface of the liquid (for example, if the liquid is water the outer surface of the orifice should be hydrophobic).

Figure 26:
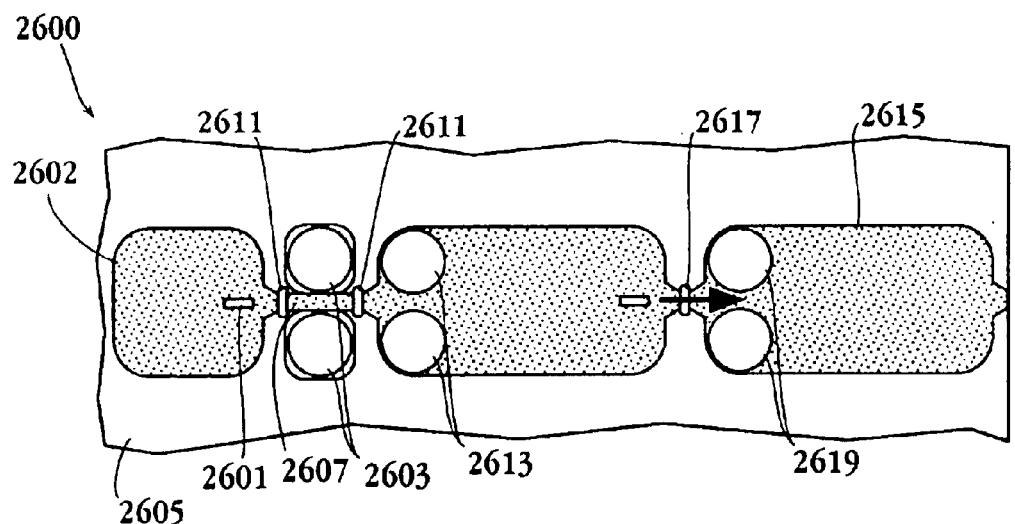
FIG. 26 depicts a top down view of a multi-chamber microlaboratory station used for reacting and incubating microparticles with a reagent that has multiple side ports interconnecting each chamber and utilizes side port access channels.

A particularly preferred embodiment of the invention does not rely on loops for moving microparticles about the workplace, but rather relies solely on in-plane biasing elements. For example, FIG. 26 depicts a top view of a multi-chamber laboratory station used for reacting and incubating microparticles with a reagent that has multiple side ports interconnecting each chamber. Microparticles are moved from chamber to chamber by activating different opposing pairs of biasing element, coils in this embodiment, in a pulsatile manner to build momentum and exert a force on a microparticle so that the moving microparticle may pass through a channel-port leading to an adjacent chamber.

In FIG. 26, microparticle 2601 in liquid 2600 contained in chamber 2602 formed in substrate 2605 is accelerated by biasing element pair 2603 towards channel-port 2607 that is in fluid communication with chamber 2609, and which is flanked by retained bubbles or air gaps 2611 that act to isolate the fluids in each chamber from one another. In a preferred embodiment, biasing element pair 2603 is a pair of coils that produces a magnetic force on a magnetic dipole microparticle 2601. Biasing elements 2613 represent auxiliary biasing elements that may be used to further usher a microparticle through channel-port 2607. Biasing elements may be located inside a chamber, as shown, or they may be located adjacent a chamber or channel-port without contacting the liquid medium. Once microparticle 2601 has remained in chamber 2609 for a selected period of time, microparticle 2601 may then be propelled into chamber 2615 through channel-port 2617 that also has a bubble for separating liquid phases. Again, microparticle 2601 is propelled by the pulsatile activation of biasing element pair 2619.

Figure 27A:
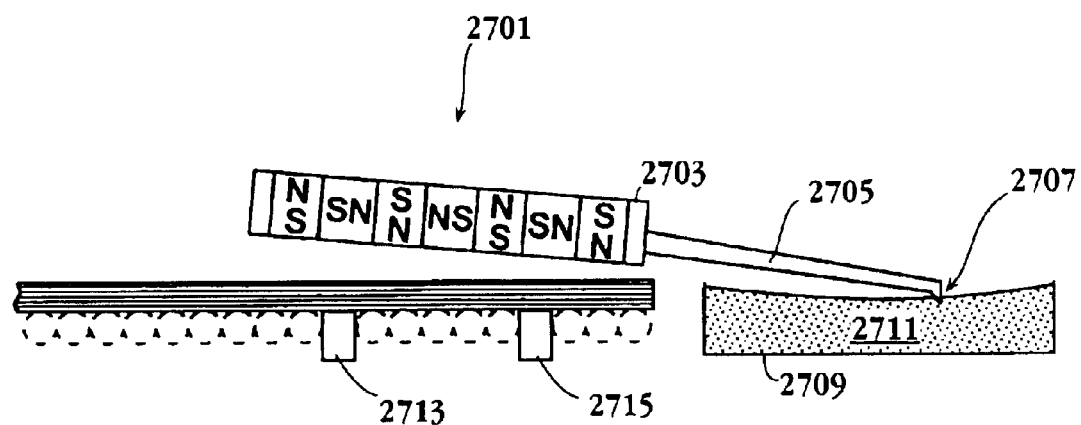

In another aspect of the invention, microparticles may be constructed having a protruding stalk with a chemical effector attached at the distal end of the stalk away from the microparticle body. FIG. 27A depicts microparticle 2701 having body 2703 having stalk 2705 attached thereto. Stalk 2705 further includes on the end away from body 2703 chemical reaction substrate 2707. In use, microparticle 2701 is ushered towards laboratory station 2709 which is a well in the embodiment shown, such that stalk 2703 extends over the well's open region. Microparticle 2901 is then tilted by activation a first biasing element 2713 and a second biasing element 2715 such that biasing element 2713 repels the region of microparticle 2701 distal from the chemical substrate 2707 to lift such region away from the biasing element, and biasing element 2715 is activated to attract a second region of microparticle 2701 to pull down such region thus causing chemical substrate 2707 to dip into the liquid 2711 contained in the well. Laboratory station 2709 contains reagent 2711.

Figure 27B:
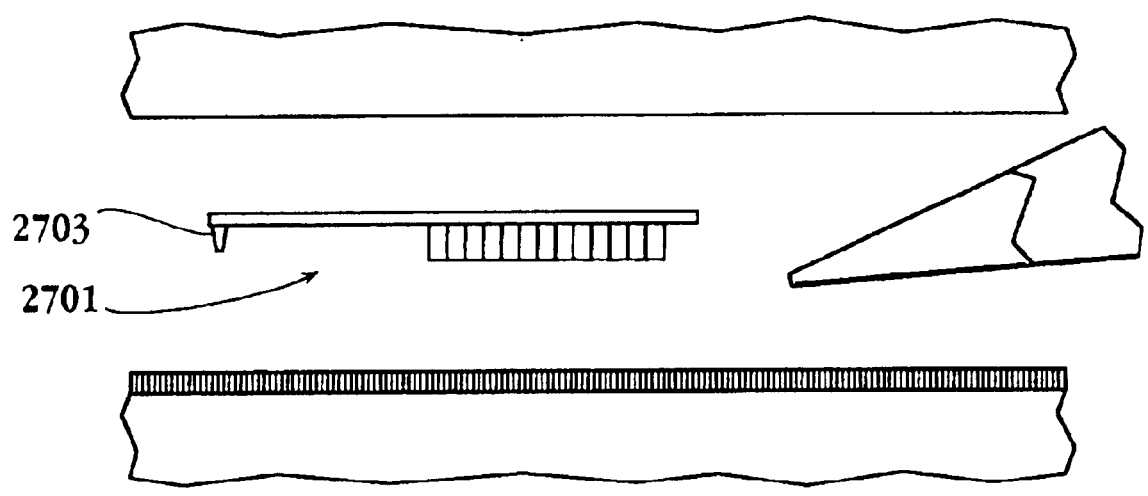

FIG. 27B is a photograph depicting microparticle with an elongated effector for picking up and depositing reagents and samples.

Figure 27C:
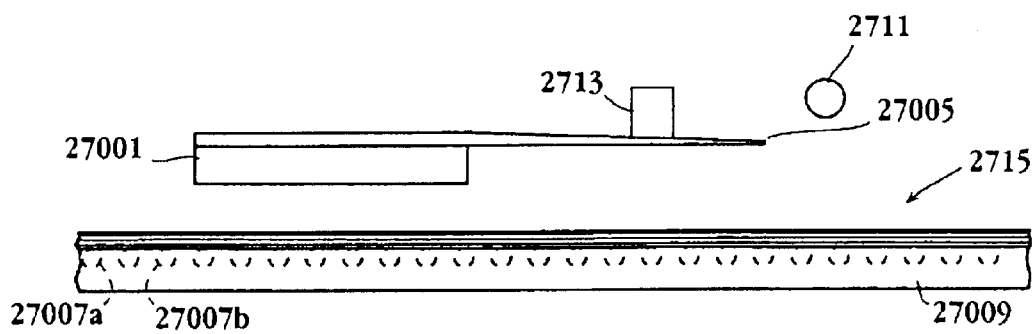
Figure 27D:
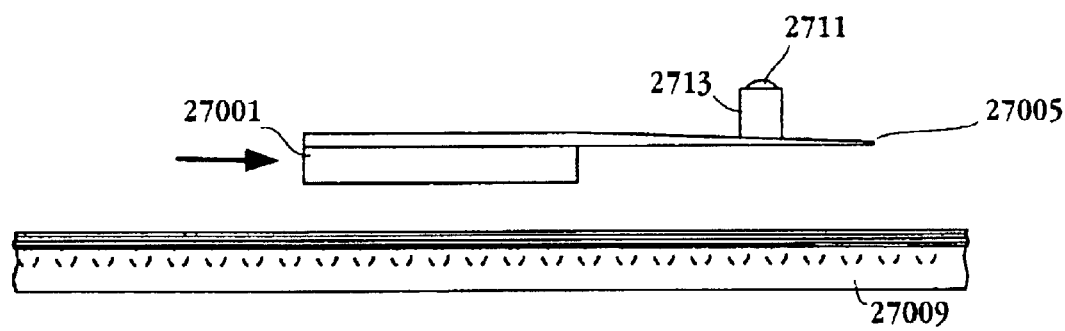
Figure 27E:
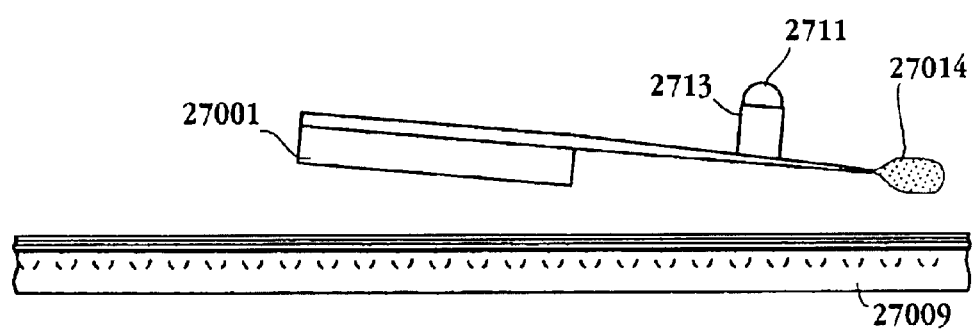
Figure 27H:
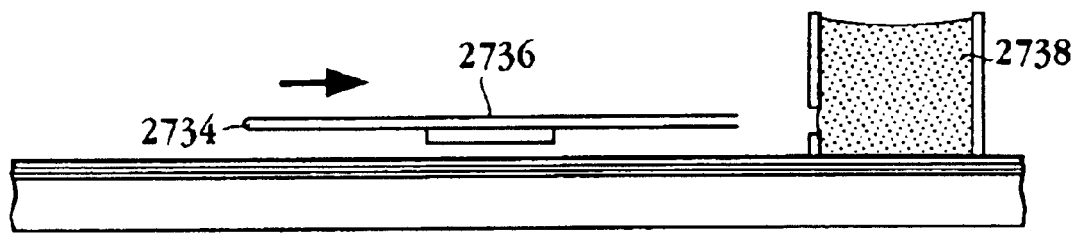
Figure 27I:
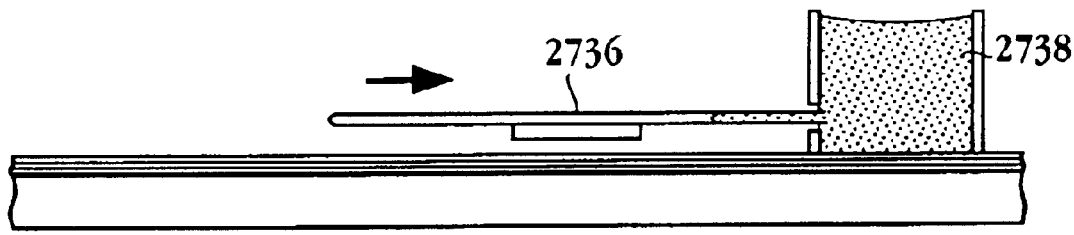
Figure 27J:
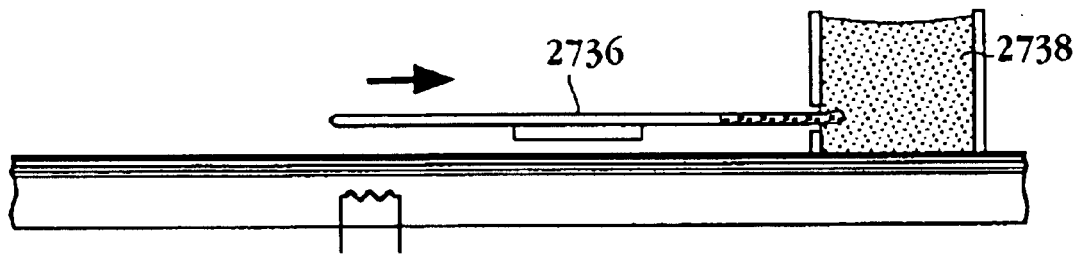
Figure 28A:
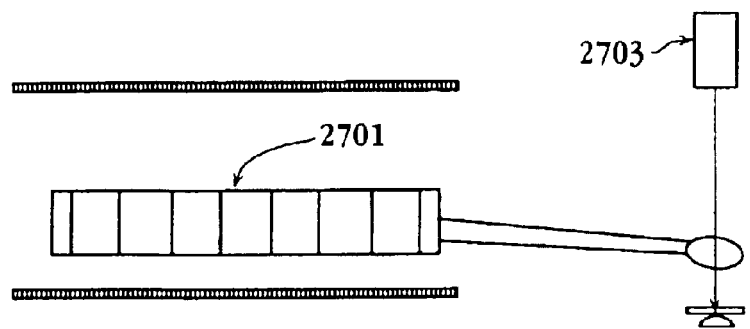
FIGS. 28A and 28B depict trans illuminating and epi-illuminating detectors for interrogating microparticles.
Figure 28B:
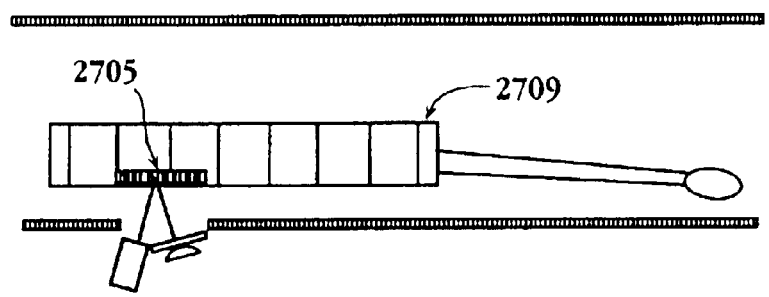
Figure 29A:
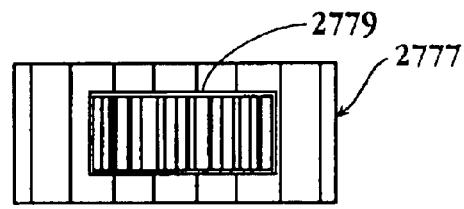
FIGS. 29A and 29B depict optically encoded and radio encoded microparticles
Figure 29B:
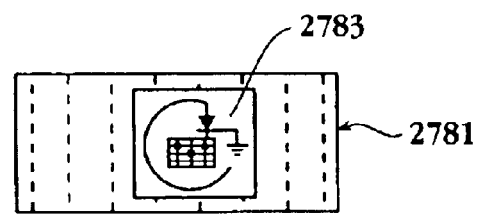

FIG. 28A depicts an effector 2701, such as the effector associated with the microparticle depicted in FIG. 27, being placed in the line of interrogation of an optical detector 2701 adapted to detect selected properties potentially associated with the effector of a microparticle. FIG. 28B depicts a micro-scale bar code 2705 imprinted upon a coding surface of a microparticle 2709. In some embodiments, the bar code is optical, and is detectable by an code reading detector such as a laser-diode/photo-detector arrangement where the bar code is read as the microparticle is moved or scanned across the observation window of the detector.

Effectors may be used to manipulate materials and compounds, for example end effectors may be used for chemical pick-up, electromagnetic weighing of the chemicals, and micro centrifuging. One preferred approach is to use controlled wetting of a small rod-shaped end effector (a stamp) to pick and place liquids, and a simple micro scoop or micro container to pick and place solids. Solids can also be handled by first exposing an end effector to a sticky but chemically inert liquid, then touching the sticky end effector onto the solid microparticles.

In certain embodiments, microweighing is achievable because diamagnetic levitation eliminates the friction, hysteresis, and nonlinearities present in other approaches.

There are options for microweighing with the invention. One option is to position the manipulator on a slight incline in the diamagnetic surface. The minimum driver trace current needed to balance the manipulator on the incline against gravity is detected via feedback from an optical sensor. The balancing trace current is directly proportional to that of the manipulator plus chemical. mass. Trace currents can be controlled very precisely, and accuracies of 1 part in 1,000 or better are not difficult to achieve. Another method of microweighing on a flat surface is to measure the acceleration or velocity produced by a given trace current, starting from an initial position. Still another technique is to measure the terminal velocity the manipulator reaches on an incline in the presence of eddy current damping. Yet another embodiment includes measuring the change in frequency of a vibrating microparticle vibrated by an oscillating biasing element or drive element.

In another aspect of the invention, microparticles may be combined with system components that together can be used to weigh very small amounts of chemicals. FIG. 27C depicts an embodiment where microparticle 27001 is configured as positionable micro manipulator 27003 with elongated end effector 27005. Driving traces 27007*a* and 27007*b* in substrate 27009 are used to position micro manipulator 27003 in the plane of substrate 27009. End effector 27003 is designed to pick up chemicals. In FIG. 27C, end effector 27005 is a simple tip which can be inserted and withdrawn from a chemical reagent well to withdraw reagent by surface tension effects (for example, the end of the tip can be hydrophilic with a water-based reagent). Many other types of end effectors may be employed such as micro scoops for picking up solid powders, micro cups, capillaries, and so forth.

In FIG. 27C, no chemical is on the tip. Note that optical beam device 2711, shown in cross section in FIG. 27C, passes through workspace 2713. An optical or infrared beam is emitted from optical beam device 2711, supplied from a source, such as a laser, infrared diode, light emitting diode, or other beam generation source, which may not be integral to optical beam device 2711, but in optical communication therewith. The source should maintain a substantially constant optical power in the beam. The beam is detected using an optical detector (not shown) such as a phototransistor, photodiode, or other optical sensing device. The optical detector detects the transmitted light power to the detector. Micro-manipulator 2727005 is positioned using the driving traces in the substrate to the desired location. In FIG. 27C, there is no added chemicals on the end effector tip. The manipulator is moved to a micro weighing position shown in FIG. 27D so that its passive sensing element 2713 blocks a portion of the light beam. That is, the passive sensing element moves between the optical beam source and the optical detector. The amount of optical power received by the optical detector is recorded.

In certain embodiments, weighing of chemicals picked up by the tip is a separate operation, the micro manipulator is again moved to the micro weighing position as shown in FIG. 27E. The added weight of the reagent 27014 causes the tip to sag downward against the magnetic forces which hold the manipulator in place. The amount of sagging is measured as an increase in optical power received by the optical detector since the passive sensing element on the manipulator now blocks less of the beam. The change in optical power is thus a measure of the weight of the chemical on the tip.

Various means can be used to calibrate the optical power received with the weight of the chemical. For example, one could place a known weight on the tip and record the change in the optically transmitted power. Alternately, for simpler but less accurate calibration, one could record the rough size of the chemical on the tip and estimate its weight, then measure the change in optical power. The change in optical power and estimated calibration weight can then be used to estimate the weight of other chemicals and other changes in optical power.

Many variations in the FIGS. 27C–E embodiment are possible. One can use magnetic or capacitive sensing, for example, rather than optical sensing to measure changes in the micromanipulator position due to added chemical weight. Other means for measuring the weight with a given sensor, such as an optical sensor, can also be employed. For example, rather than use the amount of sagging as a direct measure of weight, one can employ a force-balance method. In the force-balance method, a control circuit adjusts the driving element electrical currents (for a magnetic manipulator) to bring the blocked optical power back to the zero weight blocked optical power. The electrical currents in the driving elements is then a measure of the weight. The direct method of measuring the sagging is simpler than the force-balance method, but the force-balance method can sometimes be used to measure weights more accurately or to measure larger weights. For example the direct sagging method may be non-linear with the chemical weight for larger weights because the transmitted optical power may be non-linear with larger weights. By contrast, the electrical currents in the driving elements needed to bring the passive sensing element back to the zero-weight location may be more linear in the weight, especially with a permanent magnet micro manipulator.

FIG. 27F depicts a closed-end capillary tube 2795 being used for an end effector for a microparticle where the tube is sealed at one end, and open on the other end. FIG. 27F depicts 2791 microparticle approaching chemical reservoir 2793 with side port 2795. Other geometries are possible. For example, the chemical reservoir could be a recessed well with the top open. The micro particle could rotate the tube downward to access the well.

In FIG. 27F, panel 27F1, driving elements, not shown, are used to move microparticle 2791 such that open end of the capillary effector 2795 enters chemical reservoir 2793 to contact with a liquid contained therein. In FIG. 27F, panel 27F2, capillary effects pull an aliquot of the chemical into the capillary tube, but since the opposite end of the tube is closed, the entrapped gas pressure rises until it balances the capillary effects. Thus, the capillary tube pulls in a fixed amount of liquid chemical, but gas is entrapped at the closed end.

FIG. 27F, panel 27F3 illustrates ejection or deposition of the chemical in the capillary. The micro particle has moved to another part of the system to deposit the chemical into a reaction chamber. Although in FIG. 27G, the reaction chamber is illustrated similar to the reservoir in FIG. 27F, other geometries can be used. In FIG. 27G, the liquid acquired by microparticle's 2791 capillary effector 2795 in FIG. 27F is urged or forced into from capillary effector 2795 into side port 2792, which is capillary side port, by heating gas previously entrapped within capillary effector 2795 when it was loaded with liquid and trapped at the closed end of the capillary effector, using an adjacent heat source (not shown in FIG. panel 27Ga). Other methods of heating the entrapped gas may be used, such as heating by laser, inductive heating, dielectric heating, conductive heating by contact with the microparticle, and others. As the gas is heated its pressure rises, forcing the chemical liquid out of the open end of the tube and into the reaction chamber. The temperature rise determines the expelling gas pressure. Typically, if the liquid chemical occupies a relatively small amount of the total tube volume, then each degree centigrade rise in temperature will raise the gas pressure by roughly 3000 dynes/cm$^2$ (300 Pa). This estimate can be made from the well known ideal gas law used to describe the pressure-volume-temperature relation of most gases. The pressure rise needed to expel the liquid can be estimated by capillary formulas such as, Pc=2 s/r, where Pc is the capillary pressure from the liquid, r is the inner radius of the tube, and s is the surface tension of the liquid. For example, if the liquid has a surface tension of 50 dynes/cm, and the capillary has an inner radius of r=0.002 cm (20 microns), then Pc=50000 dynes/cm$^2$. The desired temperature rise of the gas is then estimated as roughly (50000/3000) C. or about 17 degrees centigrade. The temperature rise can be reduced by increasing the tube radius if desired. It should also be noted that the temperature rise at the liquid end can be less than the average temperature rise of the gas if heating is concentrated at the opposite closed end. This consideration would be important, for example, using chemicals that are sensitive to temperature. In some embodiments, the microparticle with its capillary effector is eventually cycled back to repeat the process. In most configurations, each individual manipulator can spend only a portion of its time actively engaged in the deposition cycle, because the system's massive parallelism and high device speed allow high throughput, even without the use of all the manipulators for deposition at the same time. The manipulators' "free" time may, for example, be used for quality control tasks such as inspection, replacement, or testing the microparticles' deposition properties off line. In certain instances, excess reagent may be removed, for example to prevent the contamination of other deposition sites. A preferred process includes aspirating excess solution and washing individual spots repeatedly with wash solutions. This embodiment of a microparticle-levitating device is used for depositing liquid or solid quanta of chemical at selected locations on a substrate. In this system, the manipulators (effectors) are mobile, so material supply and handling is fully automated. The reagent reservoirs are simply placed in proximity to the system, and the manipulators pick up and deposit the chemicals as needed. The end effectors for chemical deposition are easy to inspect at one or a few inspection locations (e.g., using optical techniques), and their performance can even be tested off line with negligible effects on production, again because the manipulators are mobile.

FIGS. 27H–J depict a microparticle 2734 having a capillary effector 2736 being used to acquire a liquid sample (FIG. 27H) insert into a receiving station 2738 (FIG. 27I) and deposit the acquired liquid sample, in this case by heated gas expulsion, as depicted in FIG. 27J.

FIGS. 29A–B depict a particle 2777 having a bar code 2779 (FIG. 29A) and a particle 2781 having a microtransmitter 2783 (FIG. 29B).

In certain embodiments, a microparticle having a microstamp effector may be microfabricated with an elevated hydrophilic platform, preferably where the remaining portions of the microparticle is hydrophobic. The microstamp effector need not be limited to one platform deposition per material acquisition step. Several reagents could be picked up and deposited per operation. An effector may comprise a platform made by micromachining silicon. The silicon dioxide on top of the platform is hydrophilic, while the surrounding silicon nitride is hydrophobic. Alternative designs with greater contrast between hydrophilic and hydrophobic regions can use thio (sulfur-containing) compounds with hydrophilic or hydrophobic end groups. The thio compounds attach themselves readily to gold, a material easily patterned by photolithography. Hydrophilic patterns of 100 μm spots may then be patterned on the deposition substrate, with hydrophobic regions surrounding the spots to confine the deposited liquid. Hydrophobic/hydrophilic patterns have been fabricated on substrates by coating glass (hydrophilic) with a hydrophobic material (e.g., organosilanes). Photoresist may then be spin coated on the hydrophobic layer, followed by conventional photolithography and plasma etching, which removes the hydrophobic material according to the lithographic pattern. The remaining photoresist may then be removed with organic solvents. The stamping process is as follows. The stamp is dipped into a reagent reservoir transported to the substrate and touches the surface. The system is maintained at a humidity level sufficient to prevent evaporation during transit. When a hydrophilic surface is touched by a stamp's reagent's meniscus, reagent is pulled onto the substrate. No solid-to-solid contact is necessary. The stamp is then moved to a wash area and dipped into slow-flowing distilled water for cleaning.

The system could also use microstamps to aspirate excess reagent. The aspiration stamp would be similar to the deposition stamp, but would have a larger hydrophilic region to draw up more liquid. After use, the aspiration stamp would be rinsed and dried. Spots are then washed wash liquid deposited by another stamp/microparticle.

The system can also be easily extended as follows: The spot size could be reduced to roughly 10 μm in diameter without violating any known limits on accuracy, fabrication, or chemistry. Thus, considerable potential exists for shrinking the deposition spots further.

Another aspect of system that can be extended in the same application domain is chemical handling before the deposition process. The system can be employed for the synthesis, storage, retrieval, and transport of large numbers of different chemicals.

In another aspect, the invention provides for methods and devices for weighing material picked up or deposited by the microparticles. For example, a microparticle may contact a dry powder and then move away from such powder while retaining a portion of that powder. The microparticle may then migrate towards a deposition region and deposit such powder by accelerating and then rapidly decelerating, for example, by impacting a stopping block where the microparticle stops abruptly, but the material carried by the microparticle continues to move forward by inertial force thereby dissociating from the microparticle. Other embodiments further utilized a scoop or capillary segment to collect a material, then again use inertial, or centripetal force to dissociate such material from the microparticle.

In another aspect of the invention, certain drive elements may be arranged in a radial manner to form a radial drive track loop that may be used to rapidly rotate microparticles to exposed radially extending portions of such microparticles to centrifugal forces. Microparticle centrifuging may be performed, in some embodiments, by spinning a levitated microparticle to high speeds, then extracting the centrifuged material. In some embodiments the effector subject to centrifugal forces is a long thin pipette-type end effector that can remove components anywhere along the centrifuge tube by precision positioning.

In another aspect, drive elements may be used not only to cause movement of microparticles, but also to detect movement of microparticles, and the nature of such movement, to glean information about the microparticle such as the overall or gross mass of the microparticle, the velocity, acceleration and deceleration of a moving microparticle, the position of a moving microparticle, the position of a non-moving microparticle. For example, in some embodiments, a drive element or other conductive sensor may be used to sense a passing-by microparticles which has associated with it one or more magnetic dipoles by using such dipoles to induce an electrical current through such drive elements or sensors. Microparticles having one dipole, for example, will cause a pulse of electrical current to be experienced by the element or sensor and its associated circuitry. If several elements or sensors are used as sensors, and if such elements or sensors are in electrical communication with a load source along with circuitry to monitor current flow, the elements and sensors may act to decelerate a moving microparticle. Information about a microparticle may be gleaned from the electrical pulses caused by its deceleration, assuming that some of the properties of the microparticle, for example, the initial mass (prior to chemical loading) and the magnetic flux or strength of the one or more dipoles.

Figure 30A:
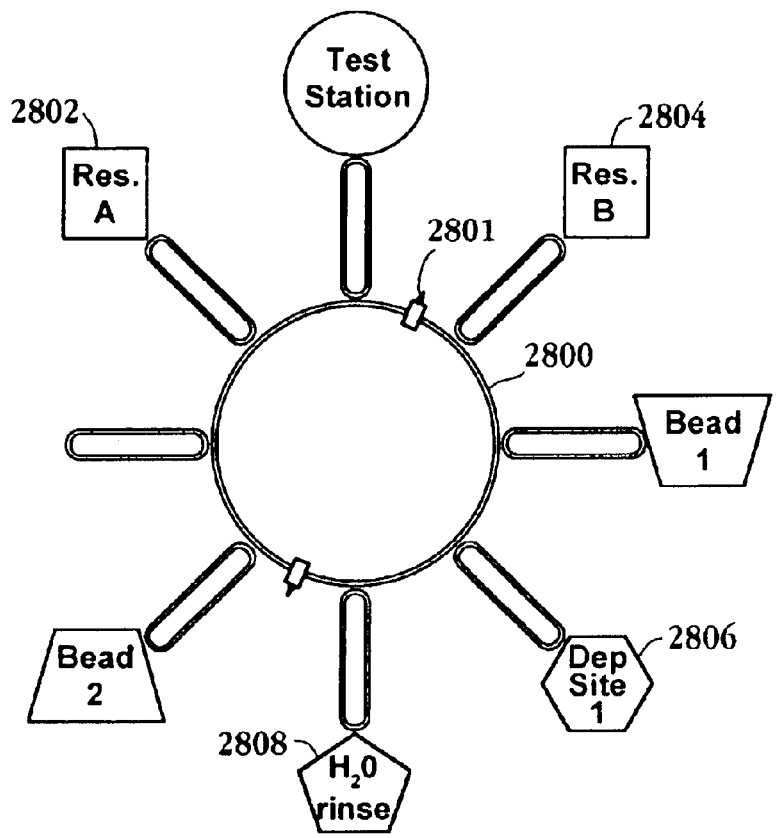
FIGS. 30A and 30B depict a top-down view of different layouts for multi-station micro-laboratories.
Figure 30B:
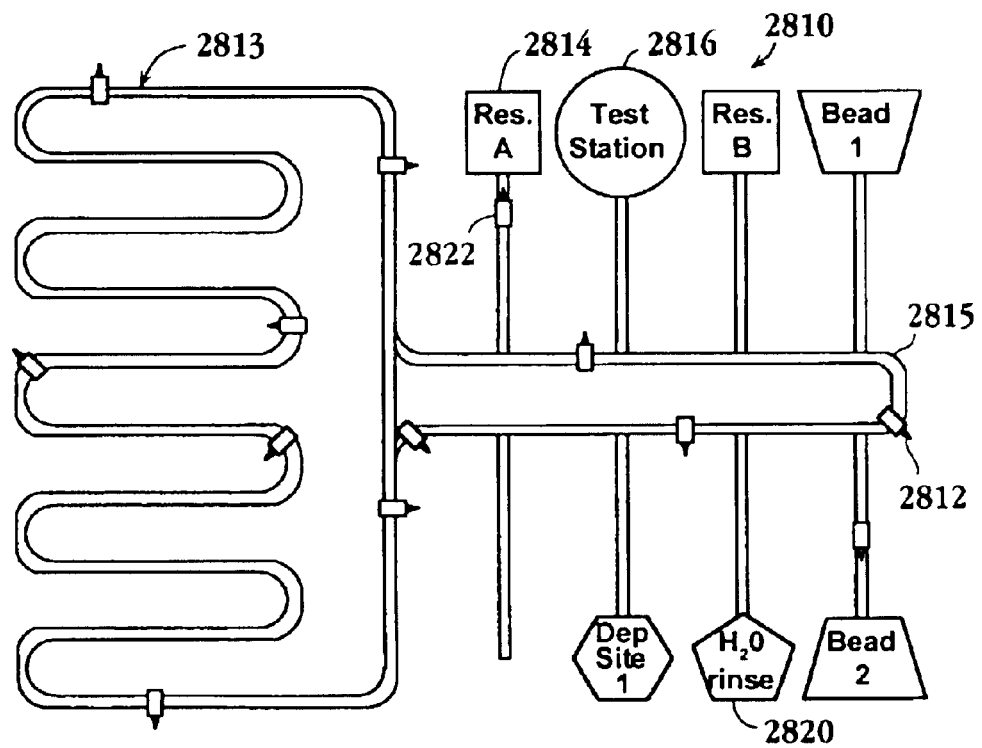

In another aspect, the invention provides for different micro-laboratory configurations. For example, FIGS. 30A and 30B depict a top-down view of different layouts for multi-station micro-laboratories. In FIG. 30A, a microparticle, such as microparticle 2801, is guided around a circular path 2800 and at various positions around the path, moved into various stations, such as indicated at 2802, 2804, 2806, 2808. The control of the particle, as it moves around the track and enters and exits specified stations, is as described above.

In the layout shown in FIG. 30B, a microparticle such as microparticle 2812, moves either along the serpentine path 2814 or the side track 2816, which services a variety of stations, such as those indicated at 2816, 2818 and 2820. The FIG. show movement, for example, of one microparticle 2822 to station 2814 for picking up a reagent or undergoing a desired microparticle treatment.

Figure 31A:
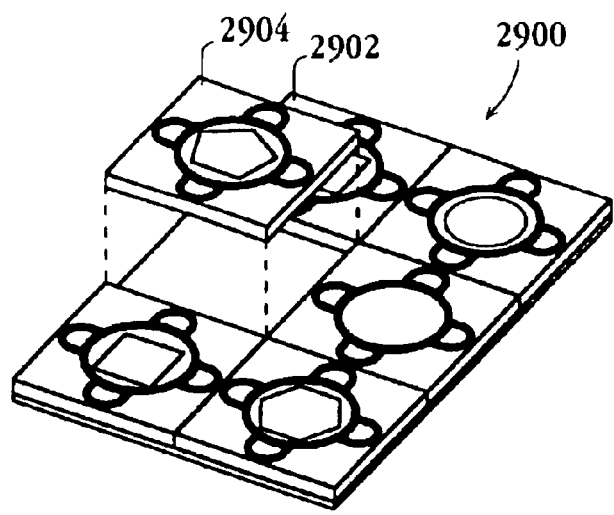
FIGS. 31A and 31B depict a multi-module micro-laboratory system where micro-lab subsystems are combined on a single support to create customized microlaboratory system.
Figure 31B:
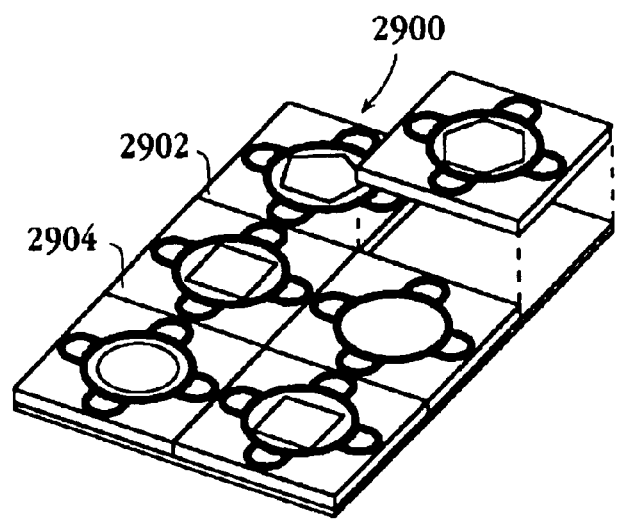

FIGS. 31A and 31B depict a multi-module micro-laboratory system 2900 where micro-lab systems of the type described above, such as indicated at 2902, 2904, are ganged together as modules for expanded functionality. For example, one module, such as module 2902, might be designed to carry out initial synthesis of library compounds one a group of beads, a second module, such as module 2904, which is physically joined to the first module, could then move the library beads to various stations containing, for example, cells, or solid supports with attached receptors molecules, to effect interaction of the bead surface compounds with the cells or receptors. After examining the interactions and identifying reactive microparticles in the second module, the first module could be replaced with yet another "library" module containing microparticles with a second chemical library. Similarly, microparticles identified as having "interesting interactions" with cells or receptors in the second module could be sequestered on either module, which would now be joined to a third module for investigating the interaction of the pre-selected beads with another target, e.g., another cell type in the third module. In some embodiments, each module will carry its own liquid reservoirs, and its own conductor traces for moving microparticles within that module. The modules will have additional surface traces adapted to mate with corresponding traces on adjacent module, for moving microparticles and/or effectors from one module to another. Overall control of microparticle and effector movement within and between modules is by a single control device that addresses the interconnected drive-element and biasing elements of the two or modules as a unified system.

Figure 32A:
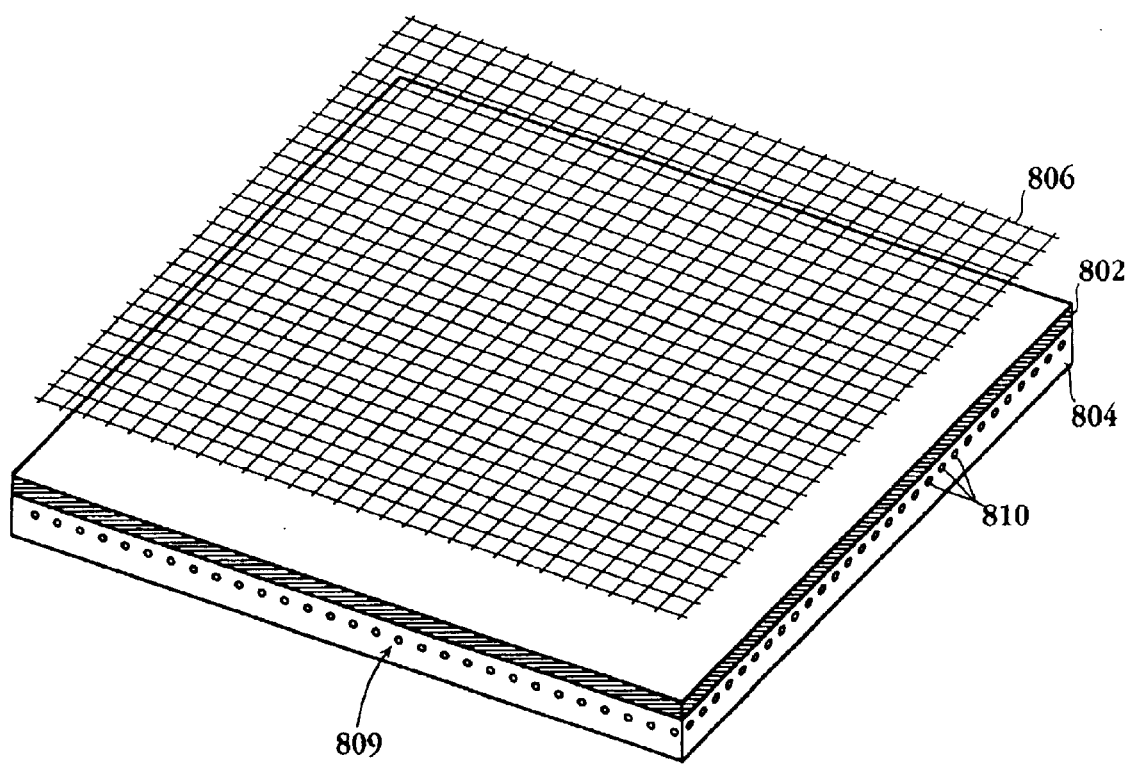
FIGS. 32A–D depict a micro-lab system having dynamic architecture.
Figure 32B:
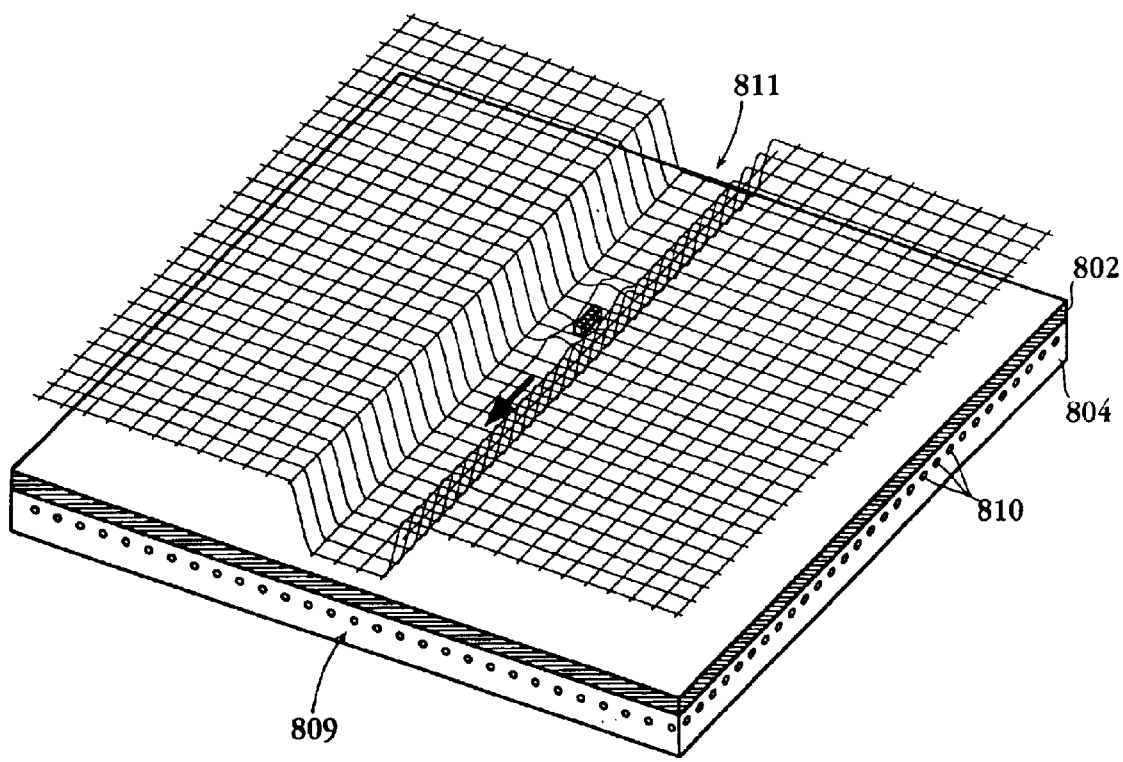
Figure 32C:
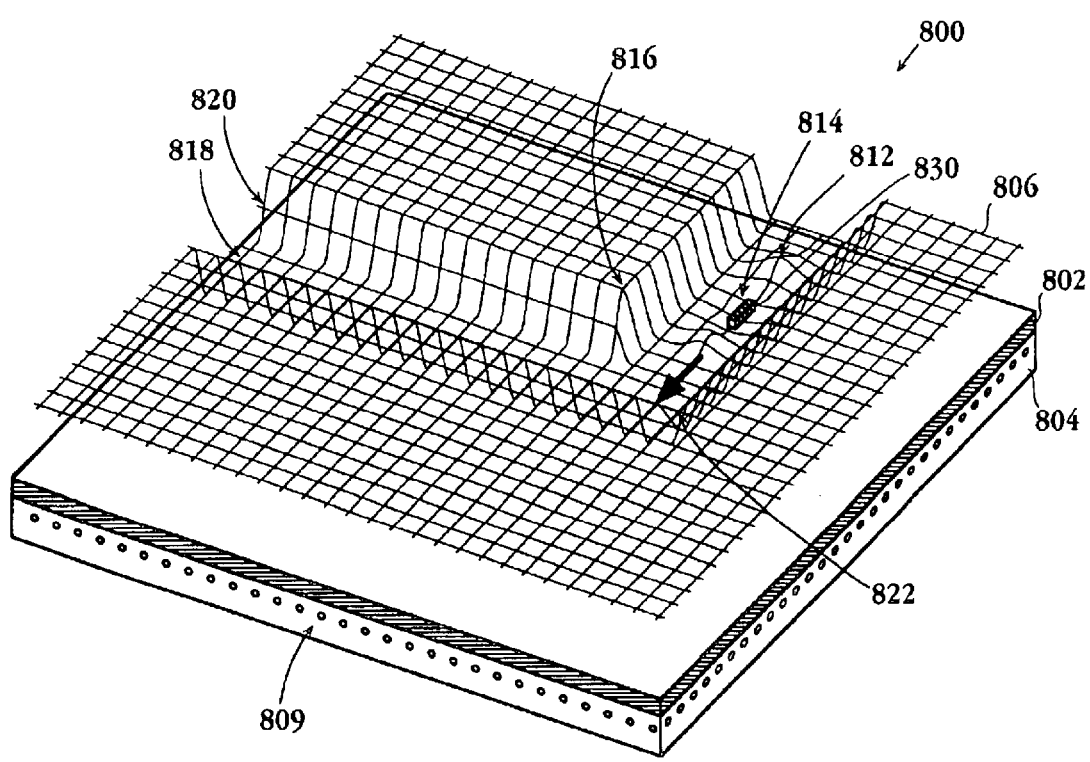
Figure 32D:
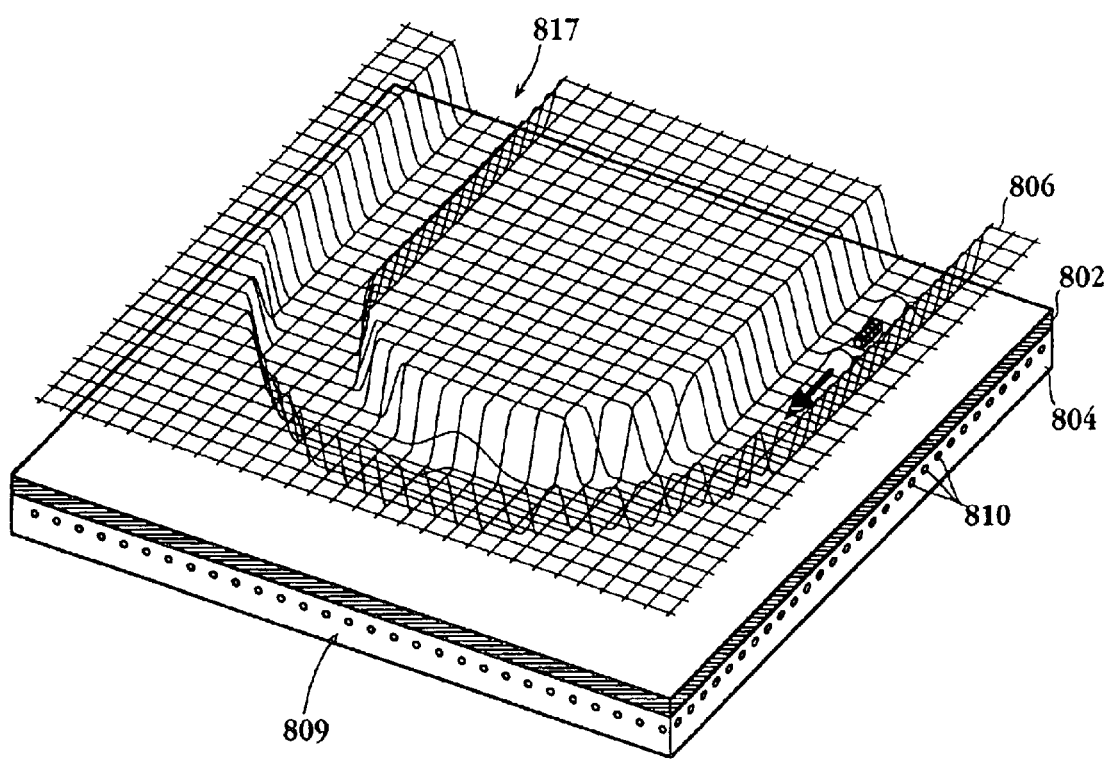

FIGS. 32A through 32D depict a system 809 having dynamic architecture. FIG. 32A depicts a substrate 804 having a drive element structure forming an independently addressable grid of drive/biasing elements 810 defining point positions operating at a nominal state, as indicated by the grid 806. When all of the points are at grid elements are at a common state, the grid is flat and particle movement is not effected. In FIG. 32B, the drive elements are biased in a manner that generates a linear potential trough 811 which serves to guide the particle along the path of the trough. Similarly, the drive elements in FIG. 32C are activated to produce an L-shaped trough 818, with sides 820, and surface potential irregularities 812, 814 for producing a desired change in particle acceleration/deceleration as well as particle direction. In FIG. 32D, the drive elements are activated to produce a U-shaped trough 817 for confining particle movement within the trough.

Figure 33:
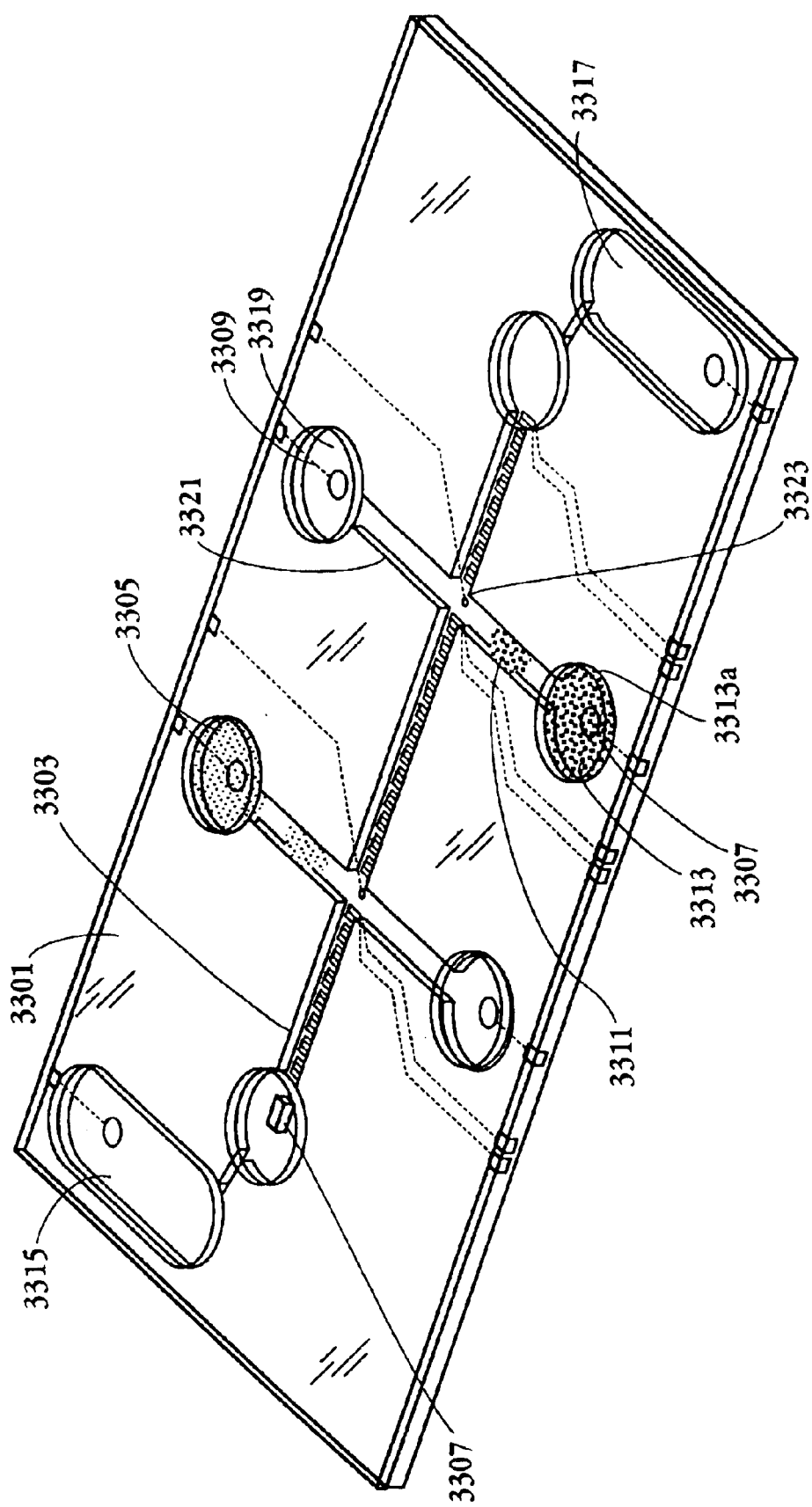
FIGS. 33 and 34 depict different channel or trench based systems.

FIG. 33 depicts another aspect of the invention which provides for an apparatus for use in performing one or more desired laboratory activities in an automated, microscale format. In certain embodiments, substrate 3301 forming a workplace expanse having an upper surface, one or more laboratory stations formed within the substrate, one or more trenches 3303 formed within the substrate, the trenches interconnecting laboratory stations 3305 in a selected format, the trenches being capable of holding one or more liquids, one or more microparticles 3307 adapted to movably fit within the trenches, the microparticles each having one or more magnetic or electrostatic dipoles and one or more laboratory effectors, a driving structure positioned adjacent the workplace, the driving structure having a plurality of drive elements selectively energizable to move one or more of the microparticles through the trenches, through interactions of the drive elements with the microparticles' dipoles, and a controller operatively linked to the drive elements for energizing the drive elements to move the one or more selected microparticles between or among selected laboratory stations interconnected by the trenches to accomplish the desired laboratory-activity.

Various embodiments may include, one or more cover structures adapted to fit against the substrate's upper surface to form therein one or more channels from the trenches, two or more electrodes for selectively passing one or more electrical currents through the trenches when such are filled with one or more conductive media, wherein the electrical currents are capable of electrokinetically causing or controlling movement of one or more reagents 3313 or analytes within the trenches and between the laboratory stations so that one or more selected reagents 3311 or analytes can selectively contact selected microparticles, a wash reservoir 3315 connected by a first trench to a first drain reservoir 3317, a reagent reservoir 3313a connected by a second trench to a second drain reservoir, wherein the first and second trenches intersect to form an intersection 3321 for transiently exposing a microparticle to a reagent, the reservoirs each having disposed therein an electrode adapted to electrically communicate with a liquid contained within the reservoirs so that when a first electrical current is passed between the reagent reservoir electrode and the second drain reservoir electrode, reagent is electrokinetically introduced into the intersection for contacting with a selected microparticle passing along the first trench through the intersection. Holding biasing element 3323 may be included to hold or situate microparticle 3307 in intersection 3323 while selected reagent 3311 is contacting microparticle 3307. The intersection may form an offset double-tee intersection. Other embodiments may include one or more biasing elements positioned adjacent the intersection(s) for selectively holding the selected microparticles within the intersections. The microparticle may be adapted for moving within the device in a levitated state. Other embodiments may include one or more diamagnetic layers defining a levitation surface wherein the microparticles are adapted to stably levitate by diamagnetic levitation. In other embodiments, the levitated state results wholly or in-part from electrostatic levitation, and/or the levitated state results wholly or in-part from buoyant levitation, and or, the levitated state results wholly or in-part from surface tension levitation, and./or the levitated state occurs transiently.

Figure 34:
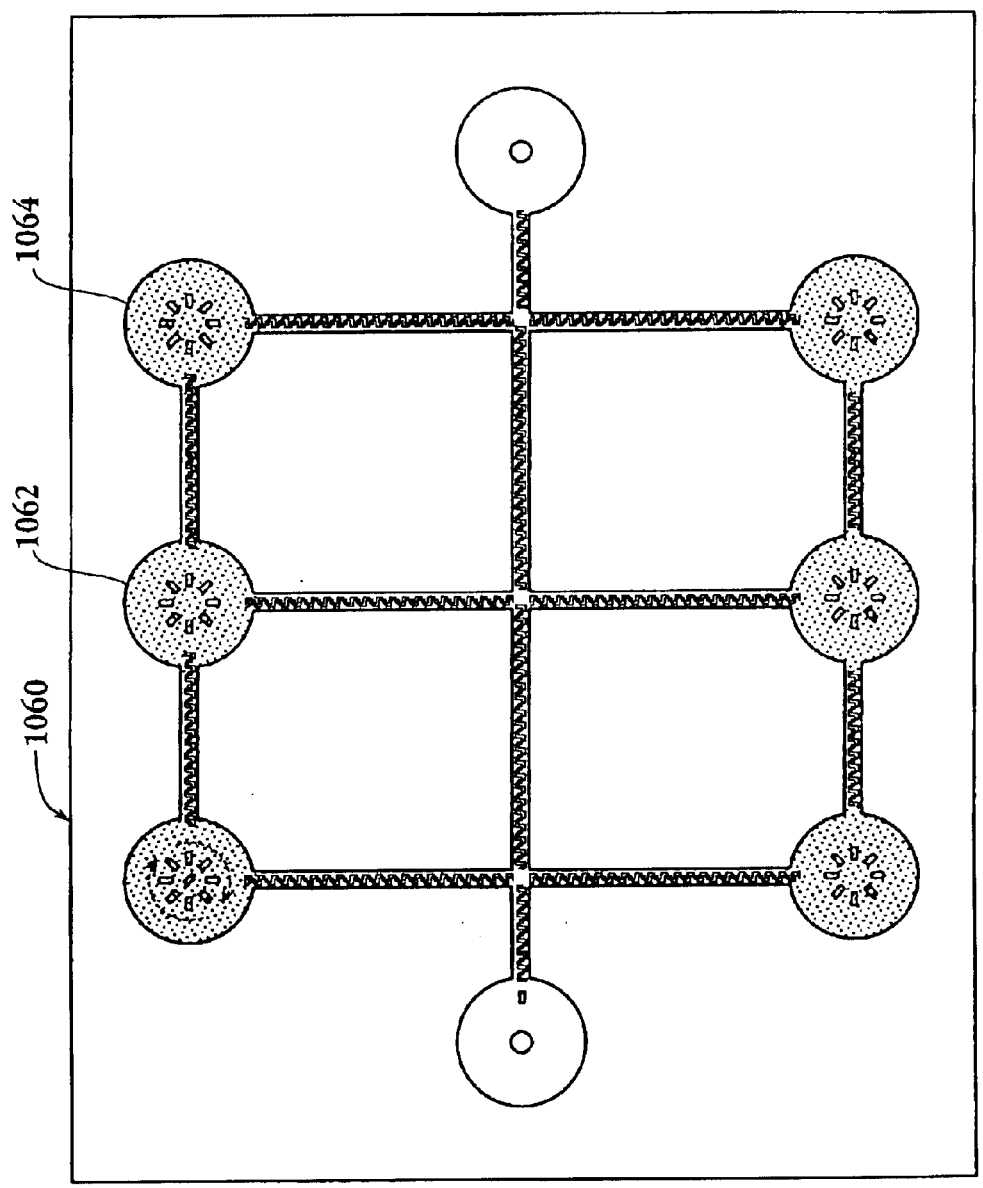

FIG. 34 depicts a multi-channel or trench device 106 with multiple reservoirs, such as reservoirs 1062, 1064, optionally having an electrode in communication with a controller, where the channels are interconnected such that each chamber may be visited after visiting another chamber without having to pass through intermediate chambers. The configuration in FIG. 34 may optionally by used such that a microparticle is moved along the long, center channel, and the intersecting channels with their reservoirs may be used to selectively expose a moving microparticle passing through an intersection.

Although particular aspects and examples have been described, it will be appreciated that various changes and modifications may be made without departing from the scope of the invention.

EXAMPLES

Example 1

Functional PCR Test of DNA Attached to a Microparticle

Figure 35:
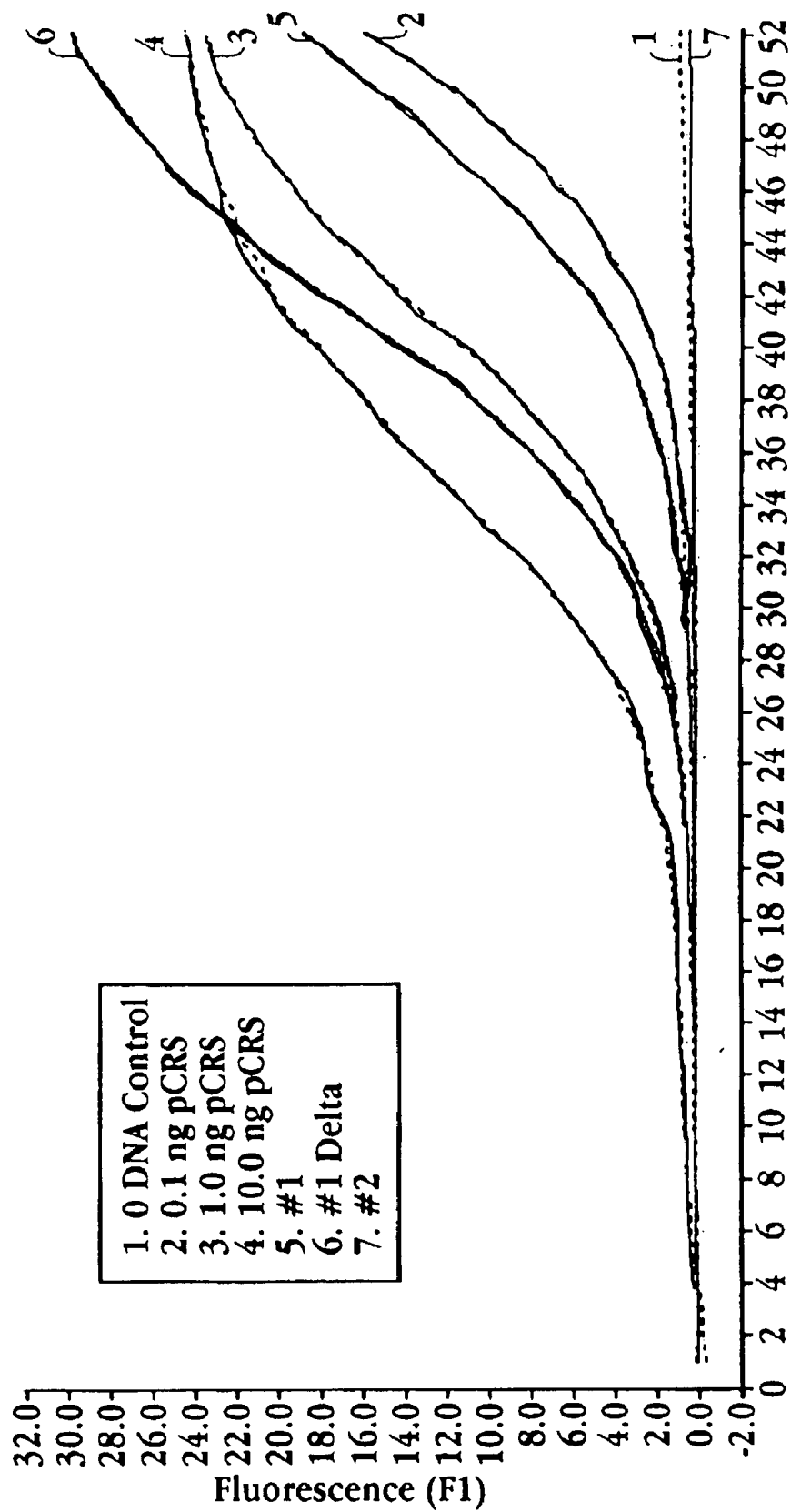
FIG. 35 depicts data corresponding to the results discussed in example 1.

Plasmid DNA at different concentrations was adsorbed to different, approximately 250 µm, rectangular silanized neodymium-iron-boron magnetizable microparticles in PCR buffer conditions. The microparticles were then independently washed, and then subjected to elution conditions using a high salt elution buffer. Aliquots of the liquid samples containing eluted DNA, if any, were transferred to independent PCR tubes. A cocktail of PCR primers, dNTPs and other PCR reagents were added to the tubes and PCR was performed. FIG. 35 depicts the results of the experiment demonstrating that DNA may be selectively acquired and released by a microparticle suitable for use in certain embodiments of the present invention.

Example 2

Flow Chart for Use in Tuning Certain Embodiments

Figure 36:
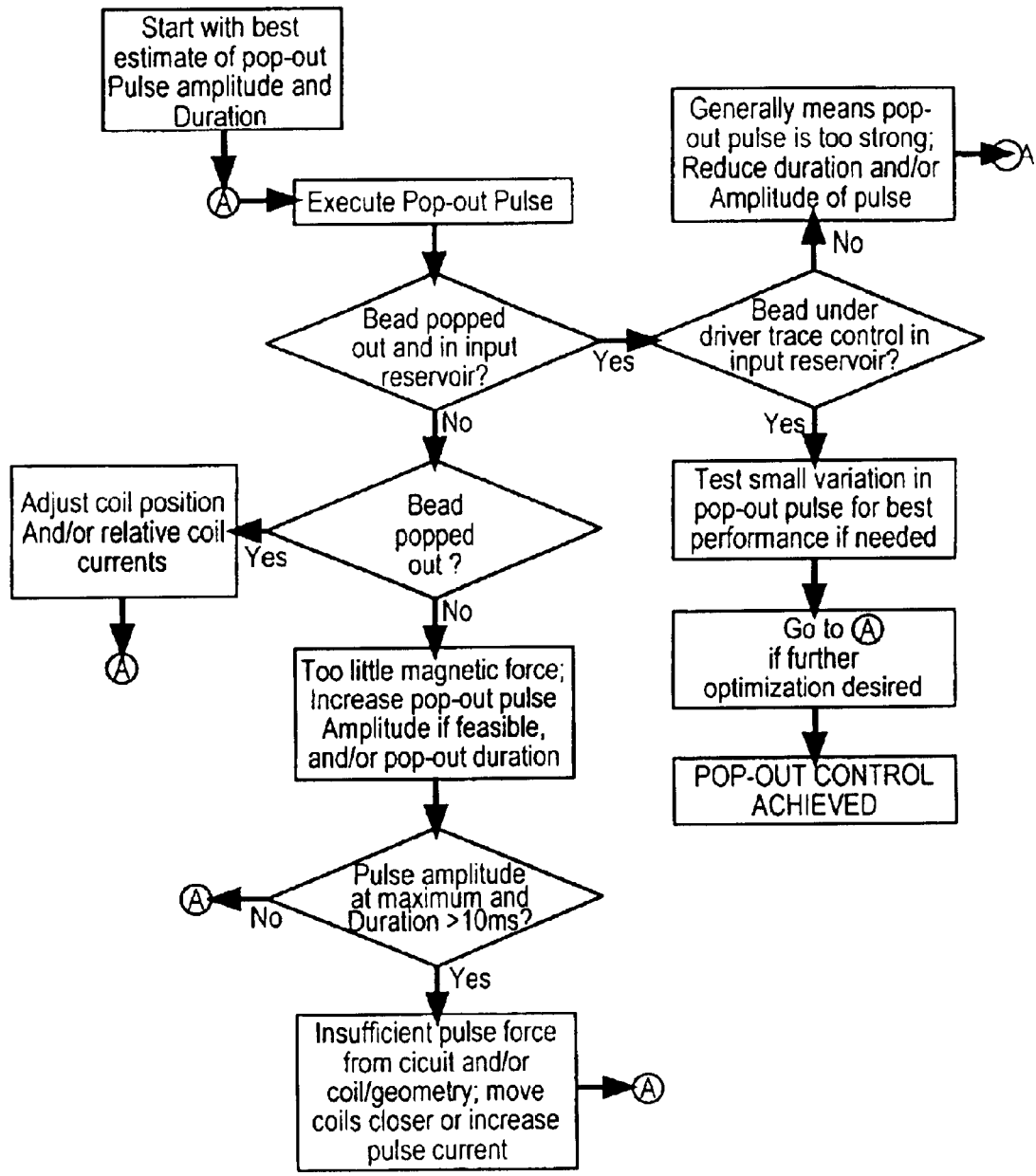
FIG. 36 depicts a flowchart used for calibrating certain embodiments of the invention.

FIG. 36 depicts a flow chart useful in tuning system parameters for certain embodiments.

Example 3

Size Specifications for an Embodiment Such as Depicted in FIG. 26

Driving Traces:
40 micron magnet wire
8 mm wavelength, square wave pattern
2 traces, offset 90 degrees spatially
Bias Traces:
100 micron magnet wire
2 mm inner diameter, 3.5 mm outer diameter, 6 turns (circuit with poppers)
2.5 mm inner diameter, 4 mm outer diameter, 6 turns (linear track)
2.8 mm (0.11") above driving traces
Pop-Out Coils
100 micron magnet wire
7 mm outer diameter, 1 mm inner diameter, 1.5 mm thick free standing coils; typical packing factor 70%
See drawing for placement relative to pop-out reservoirs It is claimed:

1. An apparatus for exposing a magnetic microparticle to a plurality of liquids, comprising:
    a) a diamagnetic substrate having a workplace defining x-y coordinates, and for levitation of said microparticle;
    b) a plurality of stations located at different known workplace x-y coordinates, each station having a chamber for holding a selected liquid, and a chamber opening forming a gas/liquid interface when said chamber contains such liquid, each station being adapted to carry out or participate in one or more selected operations;
    c) a driving structure positioned adjacent said workplace, said driving structure having drive elements selectively energizable (i) to cause an interaction between selected energized drive elements and one or more selected microparticles, to move said microparticles between selected workplace x-y coordinates, with said microparticles in a levitated state, through interaction of said drive element with said microparticles' dipoles, and (ii) to cause an interaction between selected energized drive elements and one or more selected microparticles, to move said microparticles across said gas/liquid interfaces at said stations; and
    d) a controller operatively linked to said of drive elements for energizing said drive elements to move said one or more selected microparticles between or among selected stations, and in and out of stations, to accomplish a desired laboratory-activity.

2. The apparatus of claim 3, wherein said stations are substantially in-plane with said x-y movement of said microparticles on said substrate, and said chamber opening includes a capillary port communicating between interior of said chamber and said workplace.

3. The apparatus of claim 1, wherein said second drive elements include a first set of drive elements for moving microparticles between selected x-y coordinates and a second set of drive elements to move microparticles across said gas/liquid interfaces, said second set of drive elements including, for each station, an exterior drive element on said external side of said station's port, and an internal drive element on said internal side of said station's port.

4. The apparatus of claim 2, wherein said interior and exterior drive elements each includes first and second electromagnetic coils disposed on opposite lateral sides of said capillary port.

5. The apparatus of claim 3, wherein said interior drive element associated with each station is energizable to move said microparticles into said chamber, and said exterior drive element associated with each station is energizable to move said microparticles out of said chamber.

6. The apparatus of claim 1, wherein one of more said stations has one or more chambers, each chamber separated from other chambers by a capillary port designed or configured to contain a gas and defines a gas/liquid interface between each chamber and said capillary port, when said chambers are filled in liquid.

7. The apparatus of claim 6, wherein a plurality of laboratory stations are arranged in a hub-and-spoke arrangement comprising a central station having a chamber with one or more central station connecting ports, and radial-spoke stations, one or more of said spoke stations having a chamber and one or more connecting ports, at least one of said spoke station connecting ports, and said central station connecting ports having a capillary segment intended to contain a gas and define a gas/liquid interface between each chamber and said capillary port, when said chambers are filled with a liquid.

8. The apparatus of claim 3, wherein said chamber is defined by a cavity formed in said substrate, said chamber opening is formed by an upper surface of liquid contained in said cavity, and said second set of drive elements are energizable to move said microparticles in a substantially z direction across said gas/liquid interface into and out of said chamber.

9. The apparatus of claim 8, wherein said second set of drive elements associated with such cavity-defined chamber include, exterior and interior drive elements disposed on exterior and interior sides of said chamber opening, respectively.

10. An apparatus for use in performing multi-particle operations, comprising:

a) a diamagnetic substrate having a workplace defining x-y coordinates, and a plurality of workstations;

b) a plurality of magnetic microparticles adapted to move over the surface of said workplace between and among said workstations;

c) a driving structure positioned adjacent said workplace, said driving structure having a plurality of drive elements selectively energizable to move a linear train of selected microparticles coordinately between selected workplace x-y coordinates with said microparticles in a levitated state, through interactions of said drive elements with said microparticles' dipoles; and d) a controller operatively linked to said drive elements for energizing said drive elements to move said microparticles between or among selected x,y coordinates to accomplish said multi-particle operation.

11. The apparatus of claim 10, wherein said microparticles, each of said microparticles having a magnetic dipole, in said train are magnetically coupled in a direction of train movement.

12. The apparatus of claim 10 wherein said microparticles, each of said microparticles having a magnetic dipole, in said train are magnetically uncoupled in a direction of train movement.

* * * * *